(12) United States Patent
Holloway et al.

(10) Patent No.: US 7,879,797 B2
(45) Date of Patent: Feb. 1, 2011

(54) HCV NS3 PROTEASE INHIBITORS

(75) Inventors: M. Katharine Holloway, Lansdale, PA (US); Nigel J. Liverton, Harleysville, PA (US); Steven W. Ludmerer, North Wales, PA (US); John A. McCauley, Maple Glen, PA (US); David Olsen, Lansdale, PA (US); Michael T. Rudd, Collegeville, PA (US); Joseph P. Vacca, Telford, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 490 days.

(21) Appl. No.: 11/919,783

(22) PCT Filed: Apr. 28, 2006

(86) PCT No.: PCT/US2006/016343

§ 371 (c)(1),
(2), (4) Date: Nov. 1, 2007

(87) PCT Pub. No.: WO2006/119061

PCT Pub. Date: Nov. 9, 2006

(65) Prior Publication Data

US 2009/0075869 A1    Mar. 19, 2009

Related U.S. Application Data

(60) Provisional application No. 60/676,806, filed on May 2, 2005.

(51) Int. Cl.
*A61K 38/00* (2006.01)
(52) U.S. Cl. .......................................... 514/2
(58) Field of Classification Search ............... None
See application file for complete search history.

(56) References Cited

U.S. PATENT DOCUMENTS

| | | | |
|---|---|---|---|
| 3,480,613 | A | 11/1969 | Walton |
| 6,323,180 | B1 | 11/2001 | Llinas-Brunet et al. |
| 6,608,027 | B1 | 8/2003 | Tsantrizos et al. |
| 6,777,395 | B2 | 8/2004 | Bhat et al. |
| 6,955,184 | B2 | 10/2005 | Friedrichs et al. |
| 7,470,664 | B2 | 12/2008 | Holloway et al. |
| 2002/0019363 | A1 | 2/2002 | Ismaili et al. |
| 2002/0107138 | A1 | 8/2002 | Hoveyda et al. |
| 2003/0236216 | A1 | 12/2003 | Devos et al. |
| 2004/0006007 | A1 | 1/2004 | Gosselin et al. |
| 2004/0063658 | A1 | 4/2004 | Roberts et al. |
| 2004/0067901 | A1 | 4/2004 | Bhat et al. |
| 2004/0229776 | A1 | 11/2004 | Chen et al. |
| 2004/0229818 | A1 | 11/2004 | Llinas-Brunet et al. |
| 2004/0254159 | A1 | 12/2004 | Hasvold et al. |
| 2004/0266668 | A1 | 12/2004 | Nakajima et al. |
| 2005/0020503 | A1 | 1/2005 | Llinas-Brunet et al. |
| 2005/0038240 | A1 | 2/2005 | Connolly et al. |
| 2006/0257980 | A1 | 11/2006 | Li |
| 2007/0027071 | A1 | 2/2007 | Holloway et al. |

FOREIGN PATENT DOCUMENTS

| | | |
|---|---|---|
| EP | 1719773 A1 | 11/2006 |
| GB | 2337262 A | 11/1999 |
| GB | 2430621 A | 4/2007 |
| WO | 97/41211 A1 | 11/1997 |
| WO | 98/22496 A2 | 5/1998 |
| WO | 98/46630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |

(Continued)

OTHER PUBLICATIONS

Christian Steinkuhler et al., Hepatitis C Virus Protease Inhibitors: Current Progress and Future Challenges, 8 Current Medicinal Chemistry 919-32 (2001).

Nathalie Goudreau & Montse Llinas-Brunet, The Therapeutic Potential of NS3 Protease Inhibitors in HCV Infection, 14(9) Expert Opin. Investig. Drugs 1129-44 (2005).

Ronald C. Griffith et al., HCV Anti-viral Agents, 39 Annual Reports in Med. Chem. 223-37 (2004).

Youla S. Tsantrizol, The Design of a Potent Inhibitor of Hepatitis C Virus NS3 Protease: BILN 2061—From the NMR Tube to the Clinic, 76 Biopolymers (Peptide Science) 309-23 (2004).

Brian W. Dymock et al., "Novel Approaches to the Treatment of Hepatitis C Virus Infection," 11 Antiviral Chemistry & Chemotherapy 79-96 (2000).

Hugo R. Rosen & David R. Gretch, "Hepatitis C virus: current understanding and prospects for future therapies," 5 Molec. Med. Today 393-99 (1999).

(Continued)

*Primary Examiner*—Christina Bradley
(74) *Attorney, Agent, or Firm*—Sheldon O. Heber; Julie M. Lake

(57) ABSTRACT

The present invention relates to macrocyclic compounds of formula (I) that are useful as inhibitors of the hepatitis C virus (HCV) NS3 protease, their synthesis, and their use for treating or preventing HCV infections.

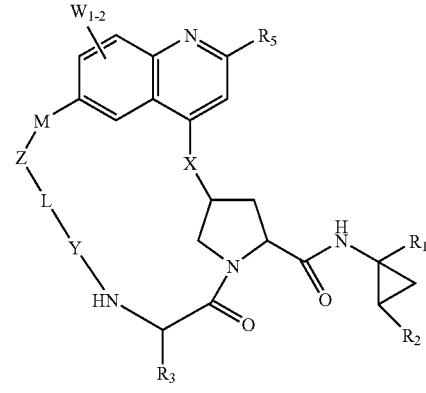

16 Claims, No Drawings

FOREIGN PATENT DOCUMENTS

| WO | 00/09543 A2 | 2/2000 |
|---|---|---|
| WO | 00/09546 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | WO 01/77113 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | WO 03/053349 A2 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 04/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A1 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Darius Moradpour & Hubert E. Blum, "Current and evolving therapies for hepatitis C," 11 Euro. J. Gastroenterol. Hepatol. 1189-1202 (1999).

Ralf Bartenschlager, "Candidate Targets for Hepatitis C Virus-Specific Antiviral Therapy," 40(5-6) Intervirology 378-93 (1997).

Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).

Brain W. Dymock, "Emerging therapies for hepatitis C virus infection," 6 Emerging Drugs 13-42 (2001).

Charlene Crabb, Infectious Diseases. "Hard-Won Advances Spark Excitement about Hepatitis C," Science 506-507 (2001).

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

Alois Furstner et al., "Total Synthesis and Structural Refinement of the Cyclic Tripyrrole Pigment Nonylprodigiosin," 64 J. Org. Chem. 8275-80 (1999).

Tina M. Trnka & Robert H. Grubbs, "The Development of L2X2R-CHR Olefin Metathesis Catalysts: An Organometallic Success Story," 34 Acc. Chem. Res. 18-29 (2001).

A. Srikrishna et al., "Enantiospecific Construction of the BC-ring System of Taxanes," 45 Tetrahedron Letters 2939-42 (2004).

Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).

Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).

Paola Conti et al., "Chemoenzymatic Synthesis of the Enantiomers of Desoxymuscarine," 9 Tetrahedron: Asymmetry 657-65 (1998).

Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).

D. Becker & N. Haddad, "Steric Effects in Intramolecular [2+2] Photocycloaddition of C=C Double Bonds to Cyclohexenones," 49(4) Tetrahedron 947-64 (1993).

Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).

Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Herbert O. House et al., "Cyclization of Unsaturated Hydroxylamine Derivatives," 41(5) J. Org. Chem. 855-63 (1976).

Theophil Eicher et al., "Bryophyte Constituents; 7: New Synthesis of (+)-Rosmarinic Acid and Related Compounds," Synthesis 755-62 (Jun. 1996).

Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexan-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

Youwei Yan et al., Complex of NS3 protease and NS4A peptide of BK strain hepatitis C virus: A 2.2 Angstrom resolution structure in a hexagonal crystal form, 7 Protein Science 837 (1998).

HCV NS3 PROTEASE INHIBITORS

CROSS-REFERENCE TO RELATED APPLICATIONS

This application is a National Stage application of International Application No. PCT/US2006/016343, filed Apr. 28, 2006. This application also claims priority to U.S. Provisional Patent Application No. 60/676,806, filed May 2, 2005.

FIELD OF THE INVENTION

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The current state of the art in the treatment of HCV infection has been discussed in the following references: B. Dymock et al., "Novel approaches to the treatment of hepatitis C virus infection," 11 *Antiviral Chem. & Chemotherapy* 79-96 (2000); H. Rosen et al., "Hepatitis C virus: current understanding and prospects for future therapies," 5 *Molec. Med. Today* 393-399 (1999); D. Moradpour et al., "Current and evolving therapies for hepatitis C," 11 *Euro. J. Gastroenterol. Hepatol.* 1189-1202 (1999); R. Bartenschlager, "Candidate Targets for Hepatitis C Virus-Specific Antiviral Therapy," 40(5-6) *Intervirology* 378-393 (1997); G. M. Lauer & B. D. Walker, "Hepatitis C Virus Infection," 345 *N. Engl. J. Med.* 41-52 (2001); B. W. Dymock, "Emerging therapies for hepatitis C virus infection," 6 *Emerging Drugs* 13-42 (2001); and C. Crabb, "Hard-Won Advances Spark Excitement about Hepatitis C," *Science:* 506-507 (2001).

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions. Previous research has identified classes of peptides, such as hexapeptides as well as tripeptides discussed in U.S. Patent Application Publications US 2005/0020503, US 2004/0229818, and US 2004/00229776, showing degrees of activity in inhibiting the NS3 protease. The aim of the present invention is to provide further compounds which exhibit activity against the HCV NS3 protease.

SUMMARY OF THE INVENTION

The present invention relates to novel macrocyclic compounds of formula (I) or pharmaceutically acceptable salts or hydrates thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts or hydrates (when appropriate), or as pharmaceutical composition ingredients, whether or not in combination with other HCV antivirals, anti-infectives, immunomodulators, antibiotics or vaccines. More particularly, the present invention relates to a compound of formula (I) or a pharmaceutically acceptable salt or hydrate thereof:

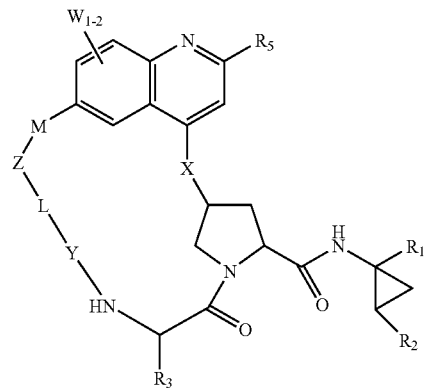

I wherein:
- $R_1$ is $CO_2R_{10}$, $CONHSO_2R_6$, tetrazole, $CONHR_6$, $CONHSO_2NR_8R_9$, $CONHP(O)R_{11}R_{12}$, or $P(O)R_{11}R_{12}$;
- $R_2$ is $C_1$-$C_4$ alkyl or $C_2$-$C_4$ alkenyl, wherein said alkyl or alkenyl is optionally substituted with 1 to 3 halo;
- $R_3$ is $C_1$-$C_8$ alkyl, $C_3$-$C_8$ cycloalkyl($C_1$-$C_8$)alkyl, aryl($C_1$-$C_8$) alkyl, Het, or $C_3$-$C_8$ cycloalkyl, wherein aryl is phenyl or naphthyl and each alkyl, cycloalkyl, or aryl is optionally substituted with 1 to 3 substituents selected from the group consisting of halo, $OR_{10}$, $SR_{10}$, $N(R_{10})_2$, $C_1$-$C_6$ alkyl, $C_1$-$C_6$ haloalkyl, $NO_2$, $CN$, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;
- Het is a 5- to 6-membered saturated cyclic ring having 1 or 2 heteroatoms selected from N, O and S, wherein said ring is optionally substituted with 1 to 3 substituents selected from halo, $OR_{10}$, $SR_{10}$, $N(R_{10})_2$, $C_1$-$C_6$ alkyl, $C_1$-$C_6$ haloalkyl, $NO_2$, $CN$, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;
- $R_4$ is H, $C_1$-$C_8$ alkyl, $C_3$-$C_8$ cycloalkyl($C_1$-$C_8$)alkyl, or aryl ($C_1$-$C_8$)alkyl; wherein aryl is phenyl or naphthyl and said alkyl, cycloalkyl, or aryl is optionally substituted with 1 to 3 substituents selected from the group consisting of halo, $OR_{10}$, $SR_{10}$, $N(R_{10})_2$, $C_1$-$C_6$ alkyl, $C_1$-$C_6$ haloalkyl, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

$R_5$ is aryl, heteroaryl, heterocyclyl, $R_{10}$, halo, $C_1$-$C_6$ alkoxy, $C_3$-$C_8$ cycloalkyl, $C_3$-$C_8$ cycloalkoxy, $C_1$-$C_6$ haloalkyl, $C_1$-$C_6$ thioalkyl, $C_2$-$C_7$ alkoxyalkyl, or $CO_2R_4$; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $OR_{10}$, $SR_{10}$, $N(R_7)_2$, $C_1$-$C_6$ alkyl, $C_1$-$C_6$ haloalkyl, $C_3$-$C_6$ cycloalkyl, cycloalkoxy, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

each $R_6$ is independently $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents or $P(O)R_{11}R_{12}$, and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

W is H, halo, $OR_{10}$, $C_1$-$C_6$ alkyl, CN, $CF_3$, $SR_{10}$, $SO_2(C_1$-$C_6$ alkyl), $C_3$-$C_8$ cycloalkyl, $C_3$-$C_8$ cycloalkoxy, $C_1$-$C_6$ haloalkyl, or $N(R_7)_2$;

X is O, NH, $N(C_1$-$C_4$ alkyl), or $CH_2$;

Y is C(=O), $SO_2$, or C(=N—CN);

Z is $CH_2$, O, or $N(R_4)$;

M is a direct bond, $C_1$-$C_8$ alkylene or $C_2$-$C_8$ alkenylene, wherein said alkylene or alkenylene is optionally substituted with 1 or 2 substituents selected from the group consisting of $C_1$-$C_8$ alkyl, $C_3$-$C_8$ cycloalkyl($C_1$-$C_8$ alkyl), aryl($C_1$-$C_8$ alkyl), and $N(R_4)_2$; and the 2 adjacent substituents of M are optionally taken together to form a 3-6 membered cyclic ring;

L is a direct bond, $C_1$-$C_5$ alkylene or $C_2$-$C_5$ alkenylene, wherein said alkylene or alkenylene is optionally substituted with 1 or 2 substituents selected from the group consisting of $C_1$-$C_8$ alkyl, $C_3$-$C_8$ cycloalkyl($C_1$-$C_8$ alkyl), and aryl($C_1$-$C_8$ alkyl);

each $R_7$ is independently H, $C_1$-$C_6$ alkyl or $C_3$-$C_6$ cycloalkyl;

$R_8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR_{10}$, $SR_{10}$, $N(R_{10})_2$, $N(C_1$-$C_6$ alkyl)O($C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0-3 heteroatoms selected from N, O and S;

$R_9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, alkoxy, cycloalkoxy, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR_{10}$, $SR_{10}$, $N(R_{10})_2$, $N(C_1$-$C_6$ alkyl)O($C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

or $R_8$ and $R_9$ are optionally taken together, with the nitrogen atom to which they are attached, to form a 4- to 8-membered monocyclic ring containing 0 to 2 additional heteroatoms selected from N, O and S;

each $R_{10}$ is independently H or $C_1$-$C_6$ alkyl;

each $R_{11}$ is independently $OR_{13}$, $N(R_{10})$—V—$CO_2R_{10}$, O—V—$CO_2R_{10}$, S—V—$CO_2R_{10}$, $N(R_{10})(R_{13})$, $R_{14}$, or $N(R_{10})SO_2R_6$;

each $R_{12}$ is independently $OR_{13}$, $N(R_{10})$—V—$CO_2R_{10}$, O—V—$CO_2R_{10}$, S—V—$CO_2R_{10}$, or $N(R_{10})(R_{13})$;

or $R_{11}$ and $R_{12}$ are optionally taken together, with the phosphorus atom to which they are attached, to form a 5- to 7-membered monocyclic ring;

each V is independently $CH(R_{15})$ or $C_1$-$C_4$ alkylene-CH($R_{15}$);

each $R_{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of aryl, aryl($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, OC(O)$OR_6$, OC(O)$R_6$, $OR_{10}$, $SR_{10}$, $N(R_{10})_2$, $C(O)R_{10}$, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R_{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is optionally substituted with 1 to 2 substituents selected from the group consisting of $C_1$-$C_6$ alkyl, halo, OC(O)OR$_6$, OC(O)R$_6$, OR$_{10}$, SR$_{10}$, N(R$_{10}$)$_2$, C(O)R$_{10}$, NO$_2$, CN, CF$_3$, SO$_2$($C_1$-$C_6$ alkyl), S(O)($C_1$-$C_6$ alkyl), NR$_{10}$SO$_2$R$_6$, SO$_2$N(R$_6$)$_2$, NHCOOR$_6$, NHCOR$_6$, NHCONHR$_6$, CO$_2$R$_{10}$, and C(O)N(R$_{10}$)$_2$; and each $R_{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of $C_1$-$C_6$ alkyl, halo, OC(O)OR$_6$, OC(O)R$_6$, OR$_{10}$, SR$_{10}$, N(R$_{10}$)$_2$, C(O)R$_{10}$, NO$_2$, CN, CF$_3$, SO$_2$($C_1$-$C_6$ alkyl), S(O)($C_1$-$C_6$ alkyl), NR$_{10}$SO$_2$R$_6$, SO$_2$N(R$_6$)$_2$, NHCOOR$_6$, NHCOR$_6$, NHCONHR$_6$, CO$_2$R$_{10}$, and C(O)N(R$_{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

The present invention also includes pharmaceutical compositions containing a compound of the present invention and methods of preparing such pharmaceutical compositions. The present invention further includes methods of treating or preventing one or more symptoms of HCV infection.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts or hydrates thereof. These compounds and their pharmaceutically acceptable salts or hydrates are HCV protease inhibitors (e.g., HCV NS3 protease inhibitors). The present invention also includes compounds of formula II or III wherein all variables are as defined for formula I.

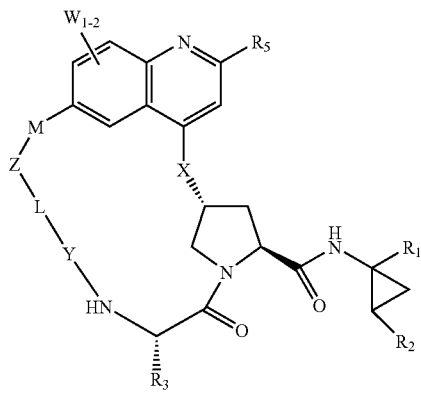

II

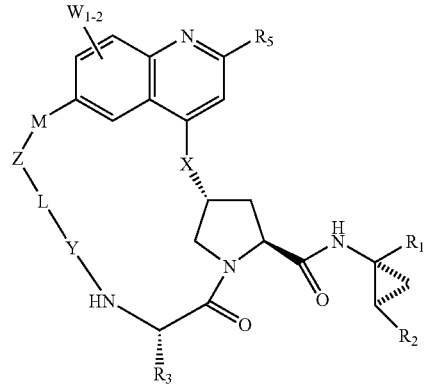

III

A first embodiment of the present invention is a compound of formula I, II or III, or a pharmaceutically acceptable salt or hydrate thereof, wherein $R_1$ is CO$_2$R$_{10}$ or CONHSO$_2$R$_6$; and all other variables are as originally defined (i.e., as defined in the Summary of the Invention). In one aspect of the first embodiment, $R_1$ is CO$_2$R$_{10}$; and all other variables are as defined in the first embodiment. In a second aspect of the first embodiment, $R_1$ is CO$_2$R$_{10}$ wherein $R_{10}$ is H; and all other variables are as defined in the first embodiment. In a third aspect of the first embodiment, $R_1$ is CONHSO$_2$R$_6$; and all other variables are as defined in the first embodiment. In a fourth aspect of the first embodiment, $R_1$ is CONHSO$_2$R$_6$ wherein $R_6$ is $C_3$-$C_6$ cycloalkyl wherein said cycloalkyl is optionally substituted with 1 to 2 W substituents; and all other variables are as defined in the first embodiment. In a fifth aspect of the first embodiment, $R_1$ is CONHSO$_2$R$_6$ wherein $R_6$ is $C_3$ cycloalkyl; and all other variables are as defined in the first embodiment.

A second embodiment of the present invention is a compound of formula I, II or III, or a pharmaceutically acceptable salt or hydrate thereof, wherein $R_2$ is $C_1$-$C_4$ alkyl or $C_2$-$C_4$ alkenyl; and all other variables are as originally defined or as defined in any one of the preceding embodiments. In one aspect of the second embodiment, $R_2$ is $C_2$-$C_4$ alkenyl; and all other variables are as defined in the second embodiment or as defined in any one of the preceding embodiments. In a second aspect of the second embodiment, $R_2$ is vinyl; and all other variables are as defined in the second embodiment or as defined in any one of the preceding embodiments. In a third aspect of the second embodiment, $R_2$ is $C_1$-$C_4$ alkyl; and all other variables are as defined in the second embodiment or as defined in any one of the preceding embodiments. In a fourth aspect of the second embodiment, $R_2$ is ethyl; and all other variables are as defined in the second embodiment or as defined in any one of the preceding embodiments.

A third embodiment of the present invention is a compound of formula I, II, or III, or a pharmaceutically acceptable salt or hydrate thereof, wherein $R_3$ is $C_1$-$C_8$ alkyl, Het or $C_3$-$C_8$ cycloalkyl, wherein said alkyl is optionally substituted with 1 to 2 substituents selected from the group consisting of halo, OR$_{10}$, SR$_{10}$, N(R$_{10}$)$_2$, $C_1$-$C_6$ alkyl, $C_1$-$C_6$ haloalkyl, NO$_2$, CN, CF$_3$, SO$_2$($C_1$-$C_6$ alkyl), NR$_{10}$SO$_2$R$_6$, SO$_2$N(R$_6$)$_2$, NHCOOR$_6$, NHCOR$_6$, NHCONHR$_6$, CO$_2$R$_{10}$, and CON(R$_{10}$)$_2$; and Het is optionally substituted with 1 to 2 substituents selected from halo, OR$_{10}$, SR$_{10}$, N(R$_{10}$)$_2$, $C_1$-$C_6$ alkyl, $C_1$-$C_6$ haloalkyl, NO$_2$, CN, CF$_3$, SO$_2$($C_1$-$C_6$ alkyl), NR$_{10}$SO$_2$R$_6$, SO$_2$N(R$_6$)$_2$, NHCOOR$_6$, NHCOR$_6$, NHCONHR$_6$, CO$_2$R$_{10}$, and CON(R$_{10}$)$_2$; and all other variables are as originally defined or as defined in any one of the preceding embodiments. In one aspect of the third embodiment, $R_3$ is $C_1$-$C_8$ alkyl or Het, wherein said alkyl is optionally substituted with 1 to 2 substituents selected from the group consisting of halo, $OR_{10}$, $SR_{10}$, $N(R_{10})_2$, $C_1$-$C_6$ alkyl, $C_1$-$C_6$ haloalkyl, $NO_2$, $CN$, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$; and all other variables are as defined in the third embodiment or as defined in any one of the preceding embodiments. In a second aspect of the third embodiment, $R_3$ is $C_1$-$C_8$ alkyl or Het; and all other variables are as defined in the third embodiment or as defined in any one of the preceding embodiments. In a third aspect of the third embodiment, $R_3$ is $C_1$-$C_6$ alkyl, piperidinyl, pyrrolidinyl, tetrahydrofuranyl or tetrahydropyranyl; and all other variables are as defined in the third embodiment or as defined in any one of the preceding embodiments. In a fourth aspect of the third embodiment, $R_3$ is propyl or butyl; and all other variables are as defined in the third embodiment or as defined in any one of the preceding embodiments. In a fifth aspect of the third embodiment, $R_3$ is i-propyl, n-butyl or t-butyl; and all other variables are as defined in the third embodiment or as defined in any one of the preceding embodiments. In a sixth aspect of the third embodiment, $R_3$ is methyl; and all other variables are as defined in the third embodiment or as defined in any one of the preceding embodiments. In a seventh aspect of the third embodiment, $R_3$ is $C_1$-$C_8$ alkyl substituted with $NHCOOR_6$ or $N(R_{10})_2$; and all other variables are as defined in the third embodiment or as defined in any one of the preceding embodiments. In an eighth aspect of the third embodiment, $R_3$ is $C_3$ alkyl substituted with $NHCOOR_{10}$ or $N(R_{10})_2$; and all other variables are as defined in the third embodiment or as defined in any one of the preceding embodiments. In a ninth aspect of the third embodiment, $R_3$ is $C_3$-$C_8$ cycloalkyl; and all other variables are as defined in the third embodiment or as defined in any one of the preceding embodiments. In a tenth aspect of the third embodiment, $R_3$ is cyclohexyl; and all other variables are as defined in the third embodiment or as defined in any one of the preceding embodiments. In an eleventh aspect of the third embodiment, $R_3$ is cyclopentyl; and all other variables are as defined in the third embodiment or as defined in any one of the preceding embodiments. In a twelfth aspect of the third embodiment, $R_3$ is Het substituted with 1 to 2 substituents selected from halo, $OR_{10}$, $SR_{10}$, $N(R_{10})_2$, $C_1$-$C_6$ alkyl, $C_1$-$C_6$ haloalkyl, $NO_2$, $CN$, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$; and all other variables are as defined in the third embodiment or as defined in any one of the preceding embodiments. In a thirteenth aspect of the third embodiment, $R_3$ is Het substituted with $NHCOOR_6$; and all other variables are as defined in the third embodiment or as defined in any one of the preceding embodiments. In a fourteenth aspect of the third embodiment, $R_3$ is piperidinyl substituted with $NHCOOR_6$ wherein $R_6$ is $C_1$-$C_6$ alkyl; and all other variables are as defined in the third embodiment or as defined in any one of the preceding embodiments.

A fourth embodiment of the present invention is a compound of formula I, II, or III, or a pharmaceutically acceptable salt or hydrate thereof, wherein $R_5$ is H, $C_1$-$C_6$ thioalkyl, $C_1$-$C_6$ alkoxy, aryl, heteroaryl, heterocyclyl, or $CO_2R_4$; wherein aryl is phenyl or naphthyl, heteroaryl is a 5- or 6-membered aromatic ring having 1, 2 or 3 heteroatoms selected from N and O, attached through a ring carbon or nitrogen, and heterocyclyl is a 5- or 6-membered saturated or unsaturated non-aromatic ring having 1 or 2 heteroatoms selected from N and O, attached through a ring carbon or nitrogen; and wherein said aryl, heteroaryl, or heterocyclyl is optionally substituted with 1 to 4 substituents selected from the group consisting of halo, $OR_{10}$, $SR_{10}$, $N(R_7)_2$, $C_1$-$C_6$ alkyl, $C_1$-$C_6$ haloalkyl, $C_3$-$C_6$ cycloalkyl, $C_3$-$C_6$ cycloalkoxy, $NO_2$, $CN$, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$; and all other variables are as originally defined or as defined in any one of the preceding embodiments.

In a first aspect of the fourth embodiment, $R_5$ is H, $C_1$-$C_6$ thioalkyl, $C_1$-$C_6$ alkoxy, aryl, heteroaryl, or heterocyclyl; wherein aryl is phenyl or naphthyl, heteroaryl is a 5- or 6-membered aromatic ring having 1, 2 or 3 heteroatoms selected from N and O, attached through a ring carbon or nitrogen, and heterocyclyl is a 5- or 6-membered saturated or unsaturated non-aromatic ring having 1 or 2 heteroatoms selected from N and O, attached through a ring carbon or nitrogen; and wherein said aryl, heteroaryl, or heterocyclyl is optionally substituted with 1 to 4 substituents selected from the group consisting of halo, $OR_{10}$, $SR_{10}$, $N(R_7)_2$, $C_1$-$C_6$ alkyl, $C_1$-$C_6$ haloalkyl, $C_3$-$C_6$ cycloalkyl, $C_3$-$C_6$ cycloalkoxy, $NO_2$, $CN$, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$; and all other variables are as defined in the fourth embodiment or as defined in any one of the preceding embodiments.

In a second aspect of the fourth embodiment, $R_5$ is aryl wherein aryl is optionally substituted with 1 to 4 substituents selected from the group consisting of halo, $OR_{10}$, $SR_{10}$, $N(R_7)_2$, $C_1$-$C_6$ alkyl, $C_1$-$C_6$ haloalkyl, $C_3$-$C_6$ cycloalkyl, $C_3$-$C_6$ cycloalkoxy, $NO_2$, $CN$, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$; and all other variables are as defined in the fourth embodiment or as defined in any one of the preceding embodiments. In a second aspect of the fourth embodiment, $R_5$ is H, $C_1$-$C_6$ thioalkyl, $C_1$-$C_6$ alkoxy,

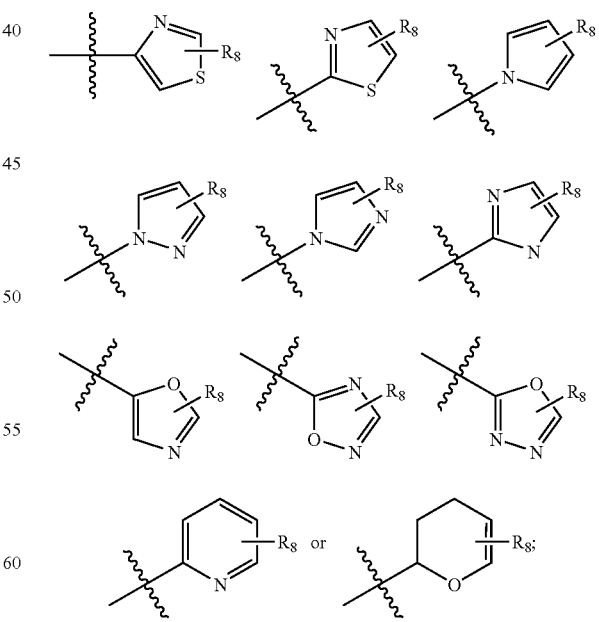

wherein $R_8$ is H, $C_1$-$C_6$ alkyl, $NHR_7$, $NHCOR_9$, $NHCONHR_9$ or $NHCOOR_9$ and each $R_9$ is independently $C_1$-$C_6$ alkyl or $C_3$-$C_6$ cycloalkyl; and all other variables are as defined in the fourth embodiment or as defined in any one of the preceding embodiments. In a third aspect of the fourth embodiment, $R_5$ is $C_1$-$C_6$ alkoxy,

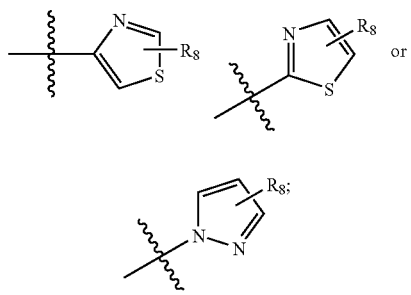

wherein $R_8$ is H, $C_1$-$C_6$ alkyl, $NHR_7$, $NHCOR_9$, $NHCONHR_9$ or $NHCOOR_9$ and each $R_9$ is independently $C_1$-$C_6$ alkyl or $C_3$-$C_6$ cycloalkyl; and all other variables are as defined in the fourth embodiment or as defined in any one of the preceding embodiments.

In a third aspect of the fourth embodiment, $R_5$ is unsubstituted phenyl; and all other variables are as defined in the fourth embodiment or as defined in any one of the preceding embodiments.

In a fourth aspect of the fourth embodiment, $R_5$ is heteroaryl optionally substituted with $N(R_7)_2$; and all other variables are as defined in the fourth embodiment or as defined in any one of the preceding embodiments.

In a fifth aspect of the fourth embodiment, $R_5$ is thiazolyl optionally substituted with $N(R_{10})_2$; and all other variables are as defined in the fourth embodiment or as defined in any one of the preceding embodiments.

In a sixth aspect of the fourth embodiment, $R_5$ is $CO_2R_4$; and all other variables are as defined in the fourth embodiment or as defined in any one of the preceding embodiments.

In a seventh aspect of the fourth embodiment, $R_5$ is $CO_2R_4$ wherein $R_4$ is H or $C_1$-$C_8$ alkyl; and all other variables are as defined in the fourth embodiment or as defined in any one of the preceding embodiments.

In an eighth aspect of the fourth embodiment, $R_5$ is $CO_2R_4$ wherein $R_4$ is H or methyl; and all other variables are as defined in the fourth embodiment or as defined in any one of the preceding embodiments.

A fifth embodiment of the present invention is a compound of formula I, II or III, or a pharmaceutically acceptable salt or hydrate thereof, wherein W is H, $C_1$-$C_6$ alkyl, $C_1$-$C_6$ alkoxy, hydroxy, chloro, or $N(R_7)_2$ wherein $R_7$ is H or $C_1$-$C_6$ alkyl. In one aspect of the fifth embodiment, W is ortho to the variable M as illustrated in formula Ia, IIa or IIIa. In a second aspect of the fifth embodiment, W is H or $C_1$-$C_6$ alkoxy; and all other variables are as defined in the fifth embodiment or as defined in any one of the preceding embodiments. In a third aspect of the fifth embodiment, W is methoxy; and all other variables are as defined in the fifth embodiment or as defined in any one of the preceding embodiments. In a fourth aspect of the fifth embodiment, W is H; and all other variables are as defined in the fifth embodiment or as defined in any one of the preceding embodiments.

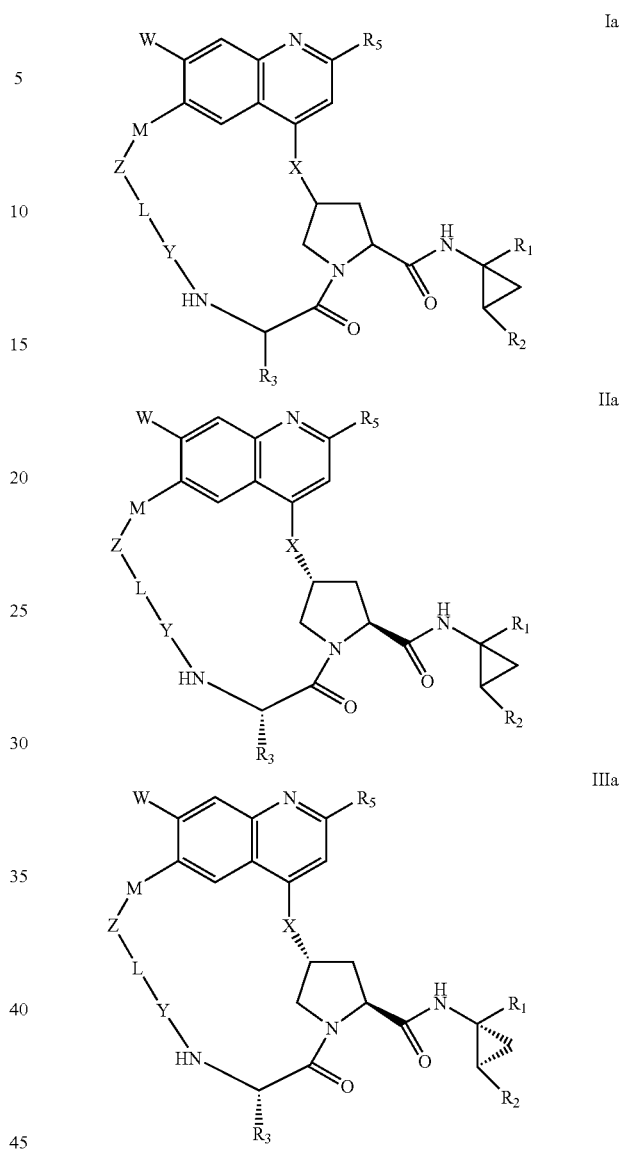

A sixth embodiment of the present invention is a compound of formula I, II or III, or a pharmaceutically acceptable salt or hydrate thereof, wherein X is O; and all other variables are as originally defined or as defined in any one of the preceding embodiments.

A seventh embodiment of the present invention is a compound of formula I, II or III, or a pharmaceutically acceptable salt or hydrate thereof, wherein Y is C=O or $SO_2$; and all other variables are as originally defined or as defined in any one of the preceding embodiments. In one aspect of the seventh embodiment, Y is C=O; and all other variables are as defined in the seventh embodiment or as defined in any one of the preceding embodiments. In another aspect of the seventh embodiment, Y is $SO_2$; and all other variables are as defined in the seventh embodiment or as defined in any one of the preceding embodiments.

An eighth embodiment of the present invention is a compound of formula I, II or III, or a pharmaceutically acceptable salt or hydrate thereof, wherein Z is O, $CH_2$ or $N(R_4)$ wherein $R_4$ is H or methyl; and all other variables are as originally defined or as defined in any one of the preceding embodiments. In a first aspect of the eighth embodiment, Z is O; and all other variables are as defined in the eighth embodiment or as defined in any one of the preceding embodiments. In a second aspect of the eighth embodiment, Z is $CH_2$; and all other variables are as defined in the eighth embodiment or as defined in any one of the preceding embodiments. In a third aspect of eighth embodiment, Z is $N(R_4)$ wherein $R_4$ is H or methyl; and all other variables are as defined in the eighth embodiment or as defined in any one of the preceding embodiments.

A ninth embodiment of the present invention is a compound of formula I, II or III, or a pharmaceutically acceptable salt or hydrate thereof, wherein M is $C_1$-$C_8$ alkylene or $C_2$-$C_8$ alkenylene, wherein said alkylene or alkenylene is optionally substituted with 1 or 2 substituents selected from $C_1$-$C_8$ alkyl, $C_3$-$C_8$ cycloalkyl($C_1$-$C_8$ alkyl), aryl($C_1$-$C_8$ alkyl) and $N(R_4)_2$; and all other variables are as defined in the ninth embodiment or as defined in any one of the preceding embodiments. In a first aspect of the eighth embodiment, M is $C_1$-$C_8$ alkylene or $C_2$-$C_8$ alkenylene, wherein said alkylene or alkenylene is optionally substituted with 1 or 2 substituents selected from $C_1$-$C_8$ alkyl, $C_3$-$C_8$ cycloalkyl($C_1$-$C_8$ alkyl), and aryl($C_1$-$C_8$ alkyl); and all other variables are as defined in the ninth embodiment or as defined in any one of the preceding embodiments. In a second aspect of the ninth embodiment, M is $C_1$-$C_8$ alkylene or $C_2$-$C_8$ alkenylene, wherein said alkylene or alkenylene is substituted with $N(R_4)_2$; and all other variables are as defined in the ninth embodiment or as defined in any one of the preceding embodiments. In a third aspect of the ninth embodiment, M is $C_1$-$C_8$ alkylene or $C_2$-$C_8$ alkenylene, wherein said alkylene or alkenylene is substituted with $N(R_4)_2$ wherein $R_4$ is $R_{10}$; and all other variables are as defined in the ninth embodiment or as defined in any one of the preceding embodiments. In a fourth aspect of the ninth embodiment, M is unsubstituted $C_1$-$C_8$ alkylene or unsubstituted $C_2$-$C_8$ alkenylene; and all other variables are as defined in the ninth embodiment or as defined in any one of the preceding embodiments. In a fifth aspect of the eighth embodiment, M is unsubstituted $C_3$ alkylene or unsubstituted $C_3$ alkenylene; and all other variables are as defined in the ninth embodiment or as defined in any one of the preceding embodiments. In a sixth aspect of the eighth embodiment, M is unsubstituted $C_4$ alkylene or unsubstituted $C_4$ alkenylene; and all other variables are as defined in the ninth embodiment or as defined in any one of the preceding embodiments. In a seventh aspect of the ninth embodiment, M is unsubstituted $C_5$ alkylene or unsubstituted $C_5$ alkenylene; and all other variables are as defined in the ninth embodiment or as defined in any one of the preceding embodiments. In an eighth aspect of the ninth embodiment, M is:

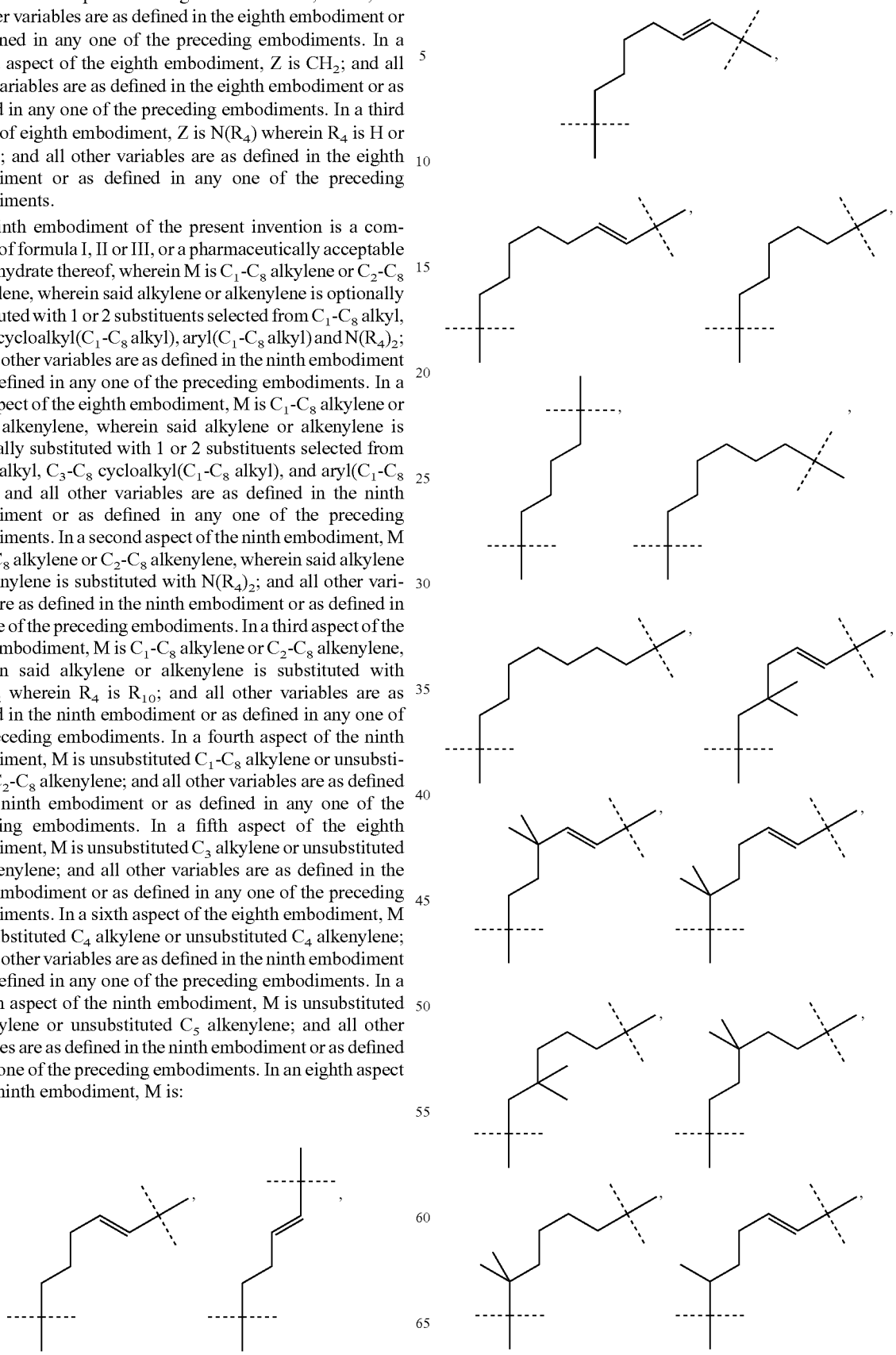

-continued

-continued

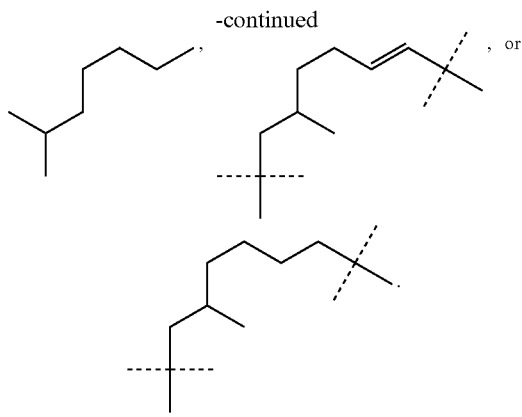

A tenth embodiment of the present invention is a compound of formula I, II or III, or a pharmaceutically acceptable salt or hydrate thereof, wherein L is a direct bond; and all other variables are as originally defined or as defined in any one of the preceding embodiments.

An eleventh embodiment of the present invention is a compound of formula I, II or III, or a pharmaceutically acceptable salt or hydrate thereof, wherein L is a direct bond and Z is O, $CH_2$ or $N(R_4)$ wherein $R_4$ is H or $C_1$-$C_8$ alkyl; and all other variables are as originally defined or as defined in any one of the preceding embodiments. In a first aspect of the eleventh embodiment, L is a direct bond and Z is O; and all other variables are as defined in the eleventh embodiment or as defined in any one of the preceding embodiments. In a second aspect of the eleventh embodiment, L is a direct bond and Z is $CH_2$; and all other variables are as defined in the eleventh embodiment or as defined in any one of the preceding embodiments. In a third aspect of the eleventh embodiment, L is a direct bond and Z is $N(R_4)$ wherein $R_4$ is H or $C_1$-$C_8$ alkyl; and all other variables are as defined in the eleventh embodiment or as defined in any one of the preceding embodiments.

A twelfth embodiment of the present invention is a compound of formula I, II or III, or a pharmaceutically acceptable salt or hydrate thereof, wherein $R_1$ is $CONHR_6$, $CONHSO_2NR_8R_9$, $CONHP(O)R_{11}R_{12}$, or $P(O)R_{11}R_{12}$; and all other variables are as originally defined or as defined in any one of the preceding embodiments.

In a first aspect of the twelfth embodiment, $R_1$ is $CONHSO_2NR_8R_9$; and all other variables are as defined in the twelfth embodiment or as defined in any one of the preceding embodiments. In a first feature of the first aspect of the twelfth embodiment, $R_8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, or heteroaryl($C_1$-$C_4$ alkyl); and $R_9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, aryl, aryl($C_1$-$C_4$ alkyl), heteroaryl, or heteroaryl($C_1$-$C_4$ alkyl), wherein said alkyl, cycloalkyl, alkoxy, aryl, or heteroaryl in both $R_8$ and $R_9$ is optionally substituted with 1 to 4 substituents selected from the group consisting of aryl, heteroaryl, $C_1$-$C_6$ alkyl, halo($C_1$-$C_6$ alkoxy), halo, $OR_{10}$, $SR_{10}$, $N(R_{10})_2$, $N(C_1$-$C_6$ alkyl)$O(C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$, wherein each aryl is independently phenyl or naphthyl and each heteroaryl is independently a 5- or 6-membered aromatic ring having 1, 2 or 3 heteroatoms selected from N, O and S, attached through a ring carbon or nitrogen, and wherein the 2 adjacent substituents of said cycloalkyl, aryl, or heteroaryl are optionally taken together to form a 3- to 6-membered cyclic ring containing 0 to 3 heteroatoms selected from N, O and S; or $R_8$ and $R_9$ are optionally taken together, with the nitrogen atom to which they are attached, to form a 4- to 8-membered monocyclic ring containing 0 to 2 additional heteroatoms selected from N, O and S; and all other variables are as defined in the twelfth embodiment or as defined in any one of the preceding embodiments.

In a second feature of the first aspect of the twelfth embodiment, $R_8$ is $C_1$-$C_8$ alkyl, $C_3$-$C_8$ cycloalkyl($C_1$-$C_8$ alkyl), aryl, aryl($C_1$-$C_4$ alkyl), heteroaryl, or heteroaryl($C_1$-$C_4$ alkyl); and $R_9$ is $C_1$-$C_8$ alkyl, $C_3$-$C_8$ cycloalkyl($C_1$-$C_8$ alkyl), $C_1$-$C_8$ alkoxy, aryl, aryl($C_1$-$C_4$ alkyl), heteroaryl, or heteroaryl($C_1$-$C_4$ alkyl), wherein said alkyl, cycloalkyl, alkoxy, aryl, or heteroaryl in both $R_8$ and $R_9$ is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR_{10}$, $SR_{10}$, $N(R_{10})_2$, $N(C_1$-$C_6$ alkyl)$O(C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$, wherein each aryl is independently phenyl or naphthyl and each heteroaryl is independently a 5- or 6-membered aromatic ring having 1, 2 or 3 heteroatoms selected from N, O and S, attached through a ring carbon or nitrogen, and wherein the 2 adjacent substituents of said cycloalkyl, aryl, or heteroaryl are optionally taken together to form a 3- to 6-membered cyclic ring containing 0 to 3 heteroatoms selected from N, O and S; or $R_8$ and $R_9$ are optionally taken together, with the nitrogen atom to which they are attached, to form a 4- to 6-membered monocyclic ring containing 0 to 2 additional heteroatoms selected from N, O and S; and all other variables are as defined in the twelfth embodiment or as defined in any one of the preceding embodiments.

In a third feature of the first aspect of the twelfth embodiment, $R_8$ is $C_1$-$C_3$ alkyl, wherein said alkyl is optionally substituted with 1 to 3 substituents selected from the group consisting of halo, $OR_{10}$, $SR_{10}$, $N(R_{10})_2$, $N(C_1$-$C_6$ alkyl)$O(C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; and $R_9$ is $C_1$-$C_3$ alkyl, $C_1$-$C_3$ alkoxy, phenyl, or —$(CH_2)_{1-2}$-phenyl, wherein said alkyl or alkoxy is optionally substituted with 1 to 3 substituents selected from the group consisting of halo, $OR_{10}$, $SR_{10}$, $N(R_{10})_2$, $N(C_1$-$C_6$ alkyl)$O(C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; or $R_8$ and $R_9$ are optionally taken together, with the nitrogen atom to which they are attached, to form a 4- to 6-membered monocyclic saturated ring containing 0 to 1 additional heteroatoms selected from N and O; and all other variables are as defined in the twelfth embodiment or as defined in any one of the preceding embodiments. In a fourth feature of the first aspect of the twelfth embodiment, $R_8$ is methyl; and all other variables are as defined in the twelfth embodiment or as defined in any one of the preceding embodiments. In a fifth feature of the first aspect of the twelfth embodiment, $R_9$ is methyl, methoxy, ethyl, i-propyl, phenyl, or benzyl; and all other variables are as defined in the twelfth embodiment or as defined in any one of the preceding embodiments. In a sixth feature of the first aspect of the twelfth embodiment, $R_8$ and $R_9$ are taken together to form a heterocyclic ring selected from the following:

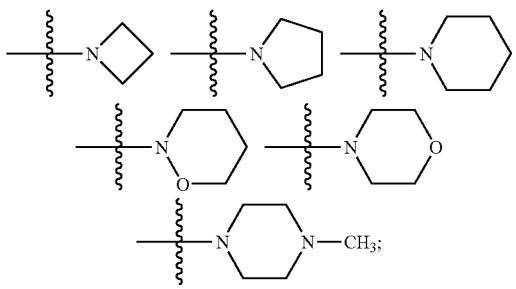

and all other variables are as defined in the twelfth embodiment or as defined in any one of the preceding embodiments. In a seventh feature of the first aspect of the twelfth embodiment, $R_8$ is methyl and $R_9$ is methoxy; and all other variables are as defined in the twelfth embodiment or as defined in any one of the preceding embodiments.

In a second aspect of the twelfth embodiment, $R_1$ is $CONHR_6$; and all other variables are as defined in the twelfth embodiment or as defined in any one of the preceding embodiments. In one feature of the second aspect of the twelfth embodiment, $R_1$ is $CONHR_6$ wherein $R_6$ is aryl($C_1$-$C_4$)alkyl optionally substituted with $P(O)R_{11}R_{12}$; and all other variables are as defined in the twelfth embodiment or as defined in any one of the preceding embodiments. In another feature of the second aspect of the twelfth embodiment, $R_1$ is $CONHR_6$ wherein $R_6$ is aryl($C_1$-$C_4$)alkyl optionally substituted with $P(O)R_{11}R_{12}$ wherein aryl is phenyl and $R_{11}$ and $R_{12}$ are $OR_{13}$ wherein $R_{13}$ is H or $C_1$-$C_6$ alkyl and all other variables are as defined in the twelfth embodiment or as defined in any one of the preceding embodiments.

In a third aspect of the twelfth embodiment, $R_1$ is CONHP(O)$R_{11}R_{12}$ or $P(O)R_{11}R_{12}$; and all other variables are as defined in the twelfth embodiment or as defined in any one of the preceding embodiments. In a first feature of the third aspect of the twelfth embodiment, both $R_1$ and $R_{12}$ are $OR_{13}$; and all other variables are as defined in the twelfth embodiment or as defined in any one of the preceding embodiments. In a second feature of the third aspect of the twelfth embodiment, $R_{11}$ is $R_{14}$ and $R_{12}$ is $OR_{13}$; and all other variables are as defined in the twelfth embodiment or as defined in any one of the preceding embodiments. In a third feature of the third aspect of the twelfth embodiment, $R_{11}$ is $N(R_{10})(R_{13})$ and $R_{12}$ is $OR_{13}$; and all other variables are as defined in the twelfth embodiment or as defined in any one of the preceding embodiments. In a fourth feature of the third aspect of the twelfth embodiment, both $R_{11}$ and $R_{12}$ are $N(R_{10})(R_{13})$; and all other variables are as defined in the twelfth embodiment or as defined in any one of the preceding embodiments.

In a fifth feature of the third aspect of the twelfth embodiment, $R_{11}$ is $N(R_{10})$—V—$CO_2R_{10}$ and $R_{12}$ is $OR_{13}$; and all other variables are as defined in the twelfth embodiment or as defined in any one of the preceding embodiments. In a sixth feature of the third aspect of the twelfth embodiment, $R_{11}$ is $N(R_{10})$—V—$CO_2R_{10}$ and $R_{12}$ is $N(R_{10})(R_{13})$; and all other variables are as defined in the twelfth embodiment or as defined in any one of the preceding embodiments. In a seventh feature of the third aspect of the twelfth embodiment, both $R_{11}$ and $R_{12}$ are $N(R_{10})$—V—$CO_2R_{10}$; and all other variables are as defined in the twelfth embodiment or as defined in any one of the preceding embodiments. In an eighth feature of the third aspect of the twelfth embodiment, $R_{11}$ is O—V—$CO_2R_{10}$ and $R_{12}$ is $OR_{13}$; and all other variables are as defined in the twelfth embodiment or as defined in any one of the preceding embodiments. In a ninth feature of the third aspect of the twelfth embodiment, $R_{11}$ is O—V—$CO_2R_{10}$ and $R_{12}$ is $N(R_{10})(R_{13})$; and all other variables are as defined in the twelfth embodiment or as defined in any one of the preceding embodiments. In a tenth feature of the third aspect of the twelfth embodiment, both $R_{11}$ and $R_{12}$ are O—V—$CO_2R_{10}$; and all other variables are as defined in the twelfth embodiment or as defined in any one of the preceding embodiments.

In an eleventh feature of the third aspect of the twelfth embodiment, $R_{11}$ is $N(R_{10})SO_2R_6$ and $R_{12}$ is $OR_{13}$; and all other variables are as defined in the twelfth embodiment or as defined in any one of the preceding embodiments. In a twelfth feature of the third aspect of the twelfth embodiment, $R_{11}$ is $N(R_{10})SO_2R_6$ wherein $R_6$ is $C_3$-$C_6$ cycloalkyl and $R_{12}$ is $OR_{13}$ wherein $R_{13}$ is H or $C_1$-$C_6$ alkyl; and all other variables are as defined in the twelfth embodiment or as defined in any one of the preceding embodiments.

In a thirteenth feature of the third aspect of the twelfth embodiment, $R_{11}$ and $R_{12}$ are taken together, with the phosphorus atom to which they are attached, to form a 5- to 7-membered monocyclic ring; and all other variables are as defined in the twelfth embodiment or as defined in any one of the preceding embodiments.

In a fourteenth feature of the third aspect of the twelfth embodiment, each $R_{13}$ is independently H, $C_1$-$C_6$ alkyl, or aryl, wherein said alkyl or aryl is optionally substituted with 1 to 2 substituents selected from the group consisting of aryl, aryl($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, OC(O)$OR_6$, OC(O)$R_6$, $OR_{10}$, $SR_{10}$, $N(R_{10})_2$, C(O)$R_{10}$, $NO_2$, CN, $CF_3$, $SO_2$($C_1$-$C_6$ alkyl), S(O)($C_1$-$C_6$ alkyl), $NR_{10}SO_2R_6$, $SO_2N(R_6)_2$, NHCOO$R_6$, NHCO$R_6$, NHCONH$R_6$, $CO_2R_{10}$, and C(O)N($R_{10}$)$_2$; and all other variables are as defined in the twelfth embodiment or as defined in any one of the preceding embodiments. In a fifteenth feature of the third aspect of the twelfth embodiment, each $R_{13}$ is independently H, $C_1$-$C_6$ alkyl, or aryl, wherein said alkyl or aryl is optionally substituted with 1 to 2 substituents selected from the group consisting of halo, OC(O)$OR_6$, OC(O)$R_6$, $OR_{10}$, CN, and $CO_2R_{10}$; and all other variables are as defined in the twelfth embodiment or as defined in any one of the preceding embodiments. In a sixteenth feature of the third aspect of the twelfth embodiment, each $R_{13}$ is independently H, $C_1$-$C_6$ alkyl, or aryl, wherein said alkyl or aryl is optionally substituted with halo, $OR_{10}$, CN, $CO_2R_{10}$, OC(O)$OR_6$ wherein $R_6$ is $C_1$-$C_6$ alkyl or $C_3$-$C_6$ cycloalkyl($C_1$-$C_4$ alkyl), or OC(O)$R_6$ wherein $R_6$ is aryl; and all other variables are as defined in the twelfth embodiment or as defined in any one of the preceding embodiments.

In a seventeenth feature of the third aspect of the twelfth embodiment, each $R_{14}$ is independently $C_1$-$C_6$ alkyl, $C_2$-$C_6$ alkenyl, aryl or heteroaryl; and all other variables are as defined in the twelfth embodiment or as defined in any one of the preceding embodiments. In an eighteenth feature of the third aspect of the twelfth embodiment, each $R_{14}$ is independently $C_1$-$C_4$ alkyl, $C_2$-$C_4$ alkenyl, phenyl or imidazolyl; and all other variables are as defined in the twelfth embodiment or as defined in any one of the preceding embodiments.

In a nineteenth feature of the third aspect of the twelfth embodiment, each V is independently CH($R_{15}$) or $CH_2CH(R_{15})$; and all other variables are as defined in the twelfth embodiment or as defined in any one of the preceding embodiments. In a twentieth feature of the third aspect of the twelfth embodiment, each V is independently CH($R_{15}$) or CH₂CH(R₁₅) and each R₁₅ is independently C₁-C₆ alkyl or aryl, wherein said alkyl or aryl is optionally substituted with 1 to 2 substituents selected from the group consisting of C₁-C₆ alkyl, halo, OC(O)OR₆, OC(O)R₆, OR₁₀, SR₁₀, N(R₁₀)₂, C(O)R₁₀, NO₂, CN, CF₃, SO₂(C₁-C₆ alkyl), S(O)(C₁-C₆ alkyl), NR₁₀SO₂R₆, SO₂N(R₆)₂, NHCOOR₆, NHCOR₆, NHCONHR₆, CO₂R₁₀, and C(O)N(R₁₀)₂; and all other variables are as defined in the twelfth embodiment or as defined in any one of the preceding embodiments. In a twenty-first feature of the third aspect of the twelfth embodiment, each V is independently CH(R₁₅) or CH₂CH(R₁₅) and each R₁₅ is independently C₁-C₆ alkyl or aryl, wherein said alkyl or aryl is optionally substituted with 1 to 2 substituents selected from the group consisting of OR₁₀ and C(O)N(R₁₀)₂; and all other variables are as defined in the twelfth embodiment or as defined in any one of the preceding embodiments.

Another embodiment of the present invention is a compound, or a pharmaceutically acceptable salt or hydrate thereof, selected from the group consisting of the compounds set forth in Examples 1 to 8 and 10 to 62 below and compounds III-9 to III-12 and III-66 to III-98.

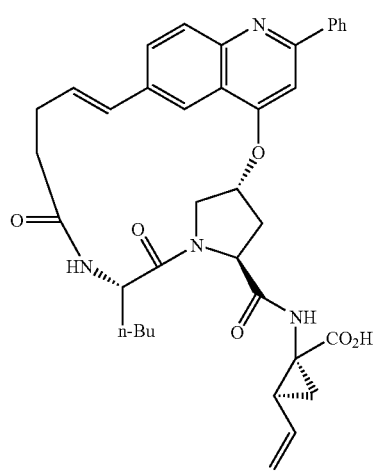

III-9

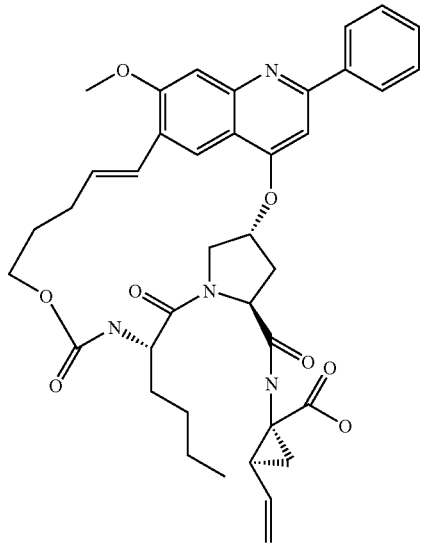

III-11

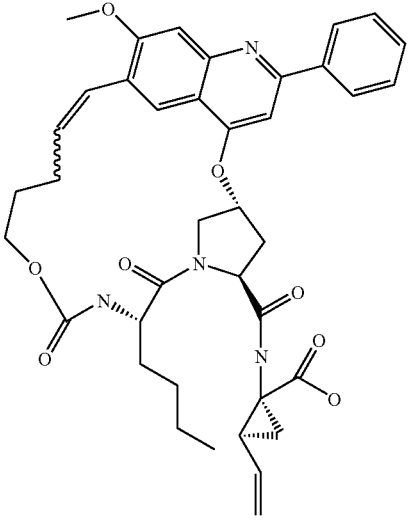

III-12

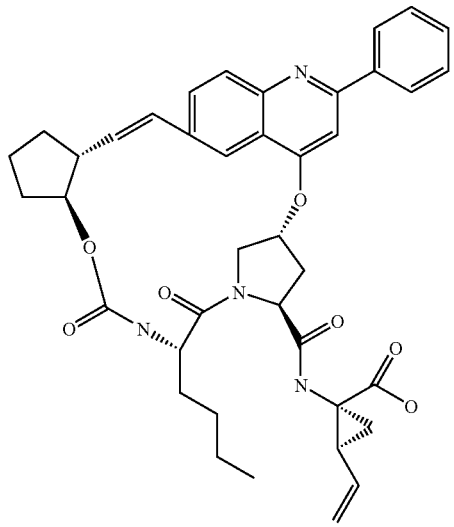

III-10

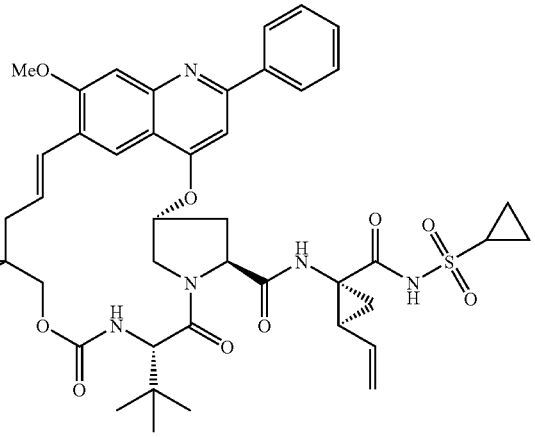

III-66

III-67
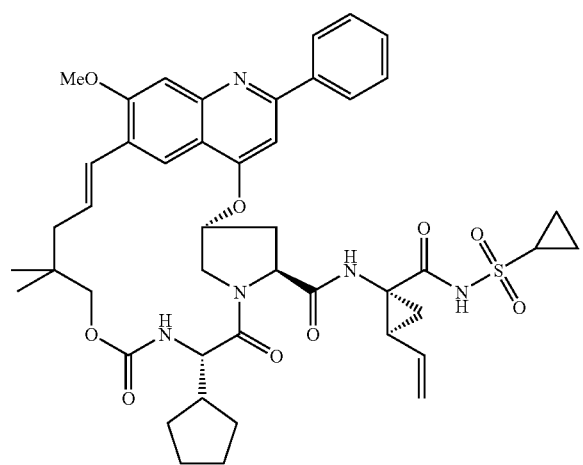
III-70
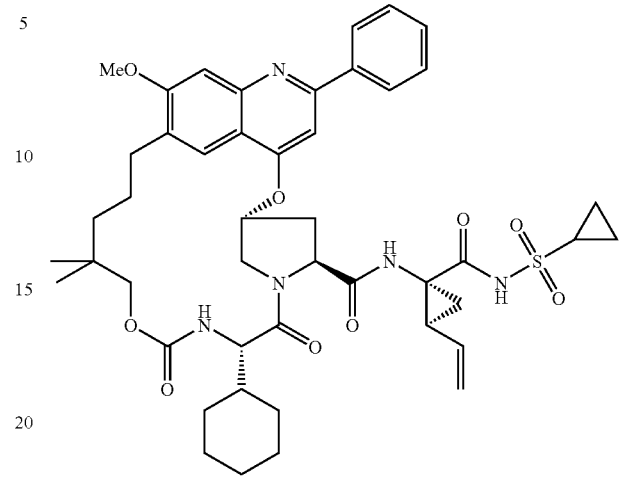
III-68
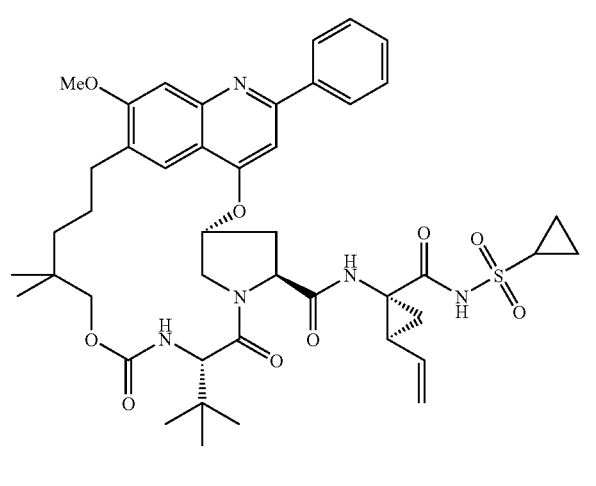
III-71
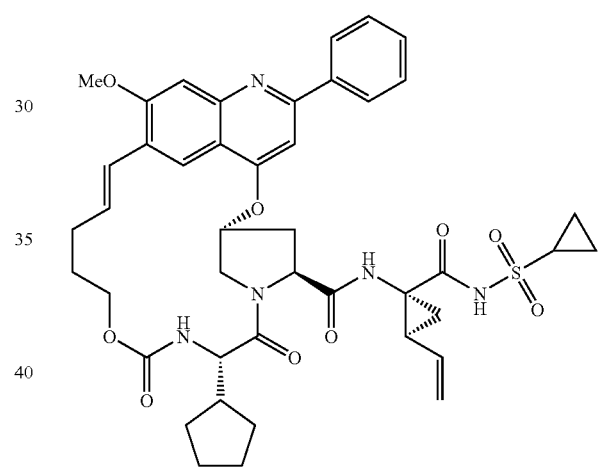
III-69
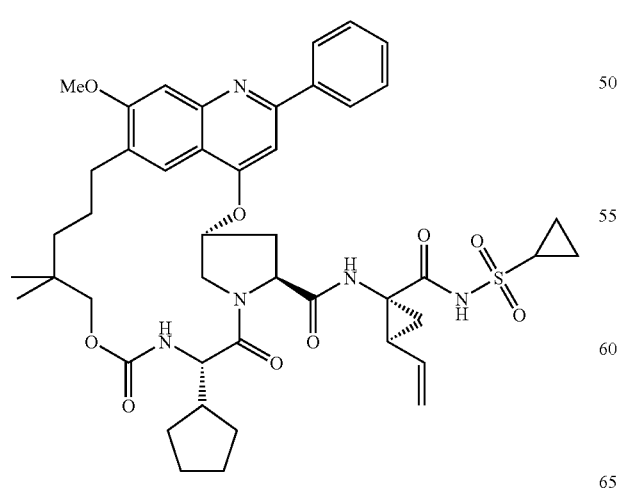
III-72
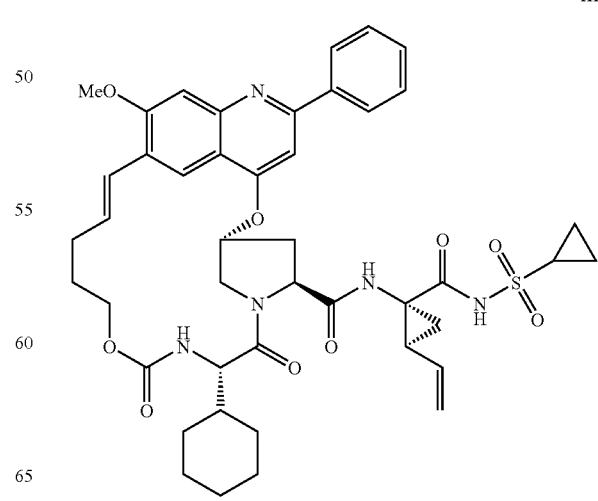

III-73
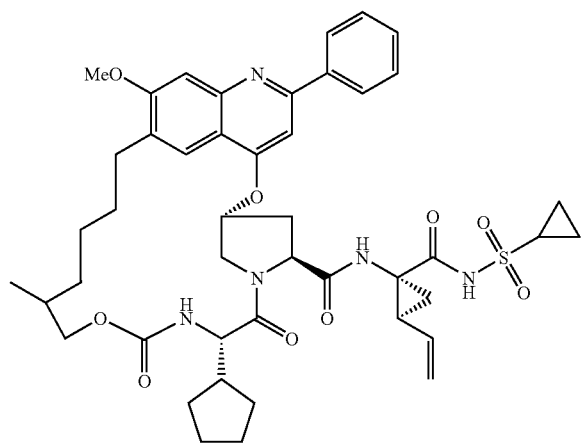
III-76
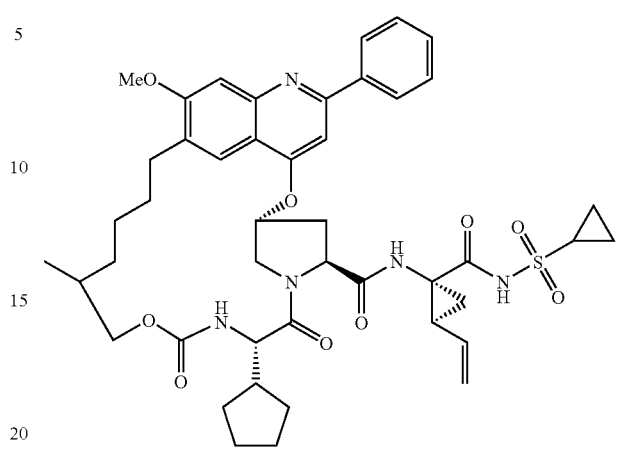
III-74
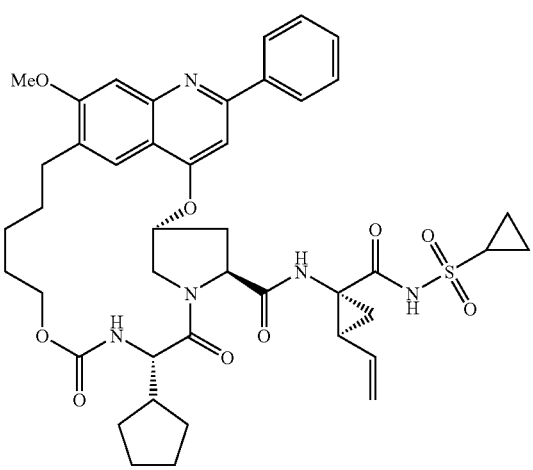
III-77
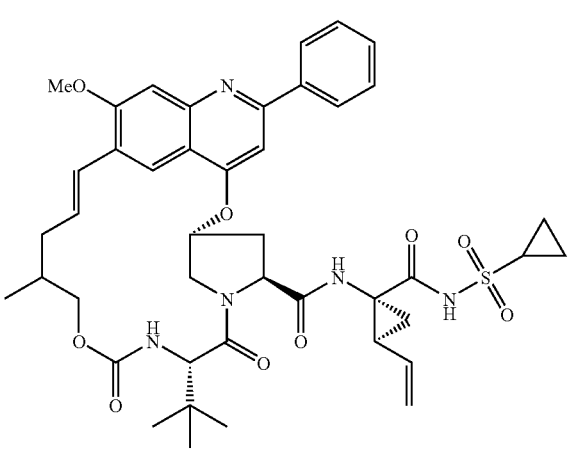
III-75
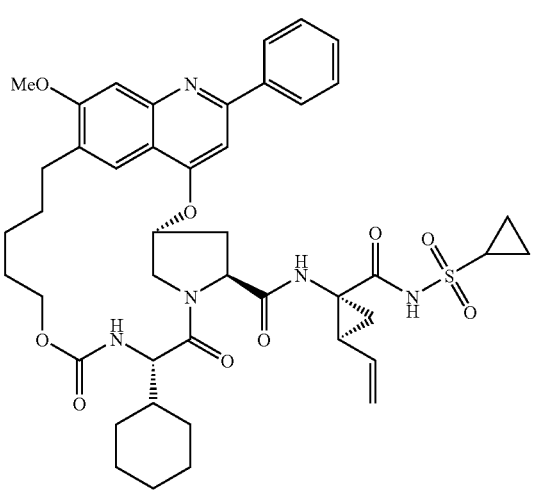
III-78
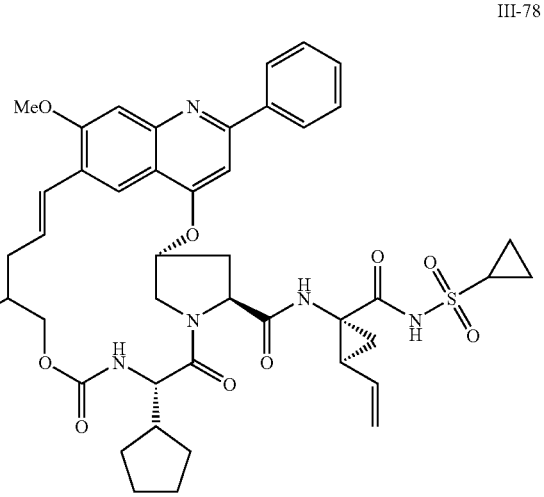

III-79
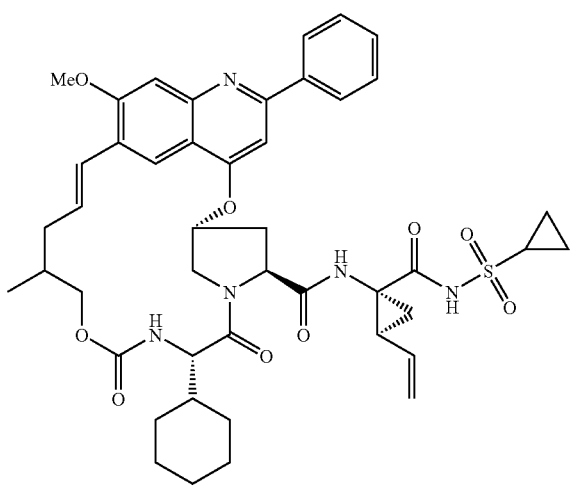
III-82
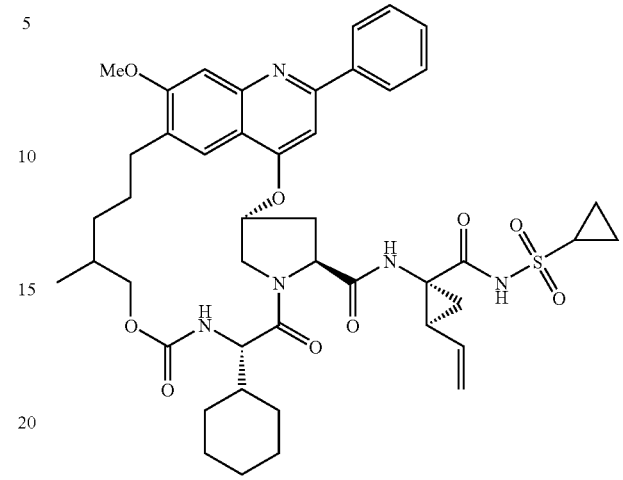
III-80
III-83
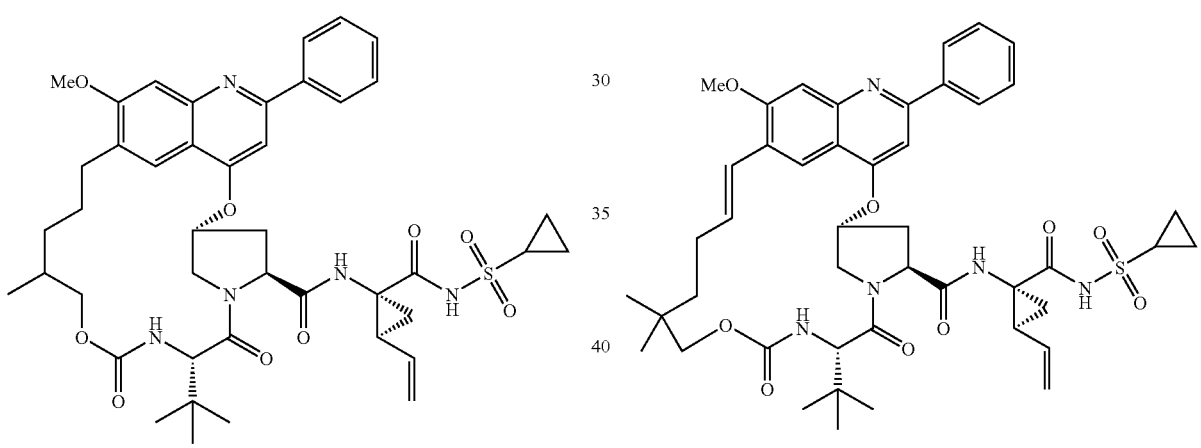
III-81
III-84
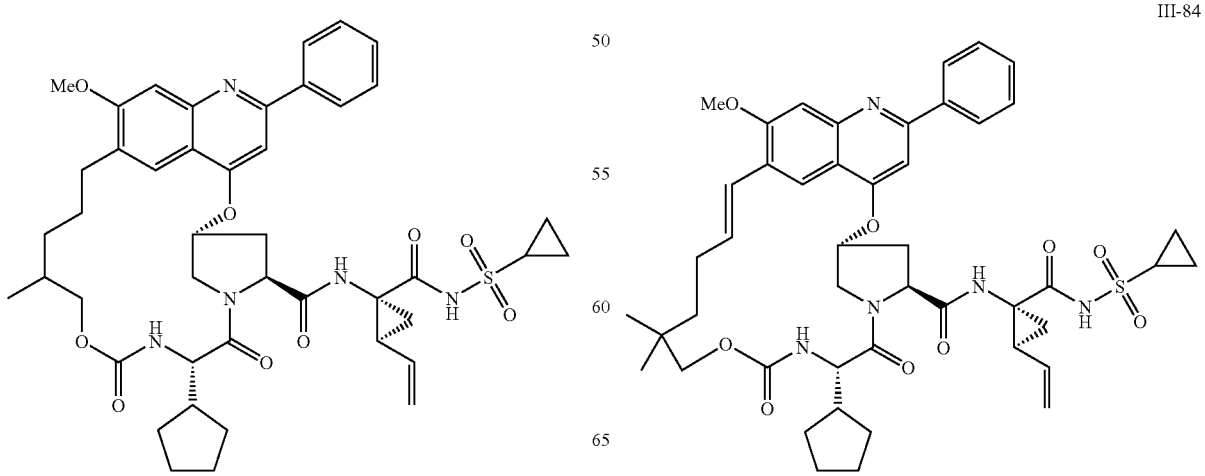

-continued
III-85
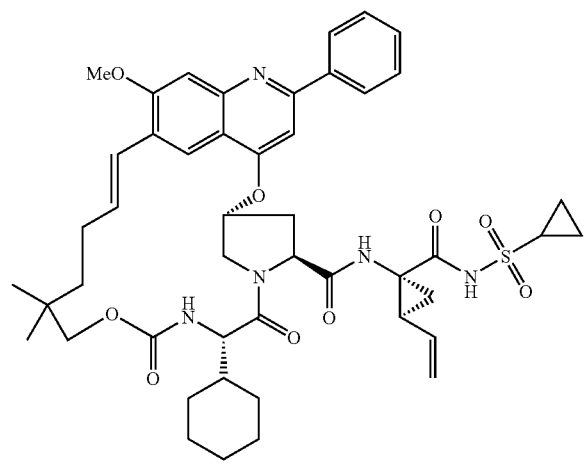
III-86
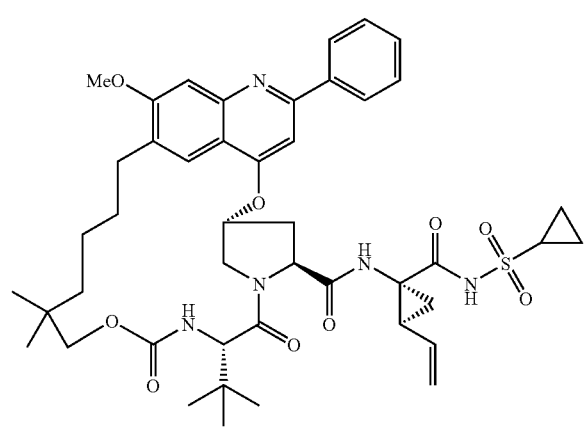
III-87
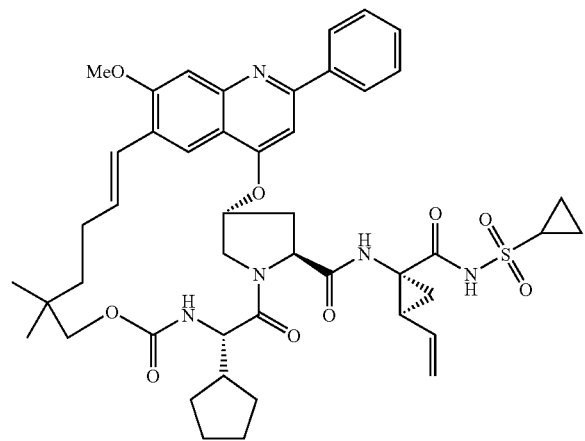
-continued
III-88
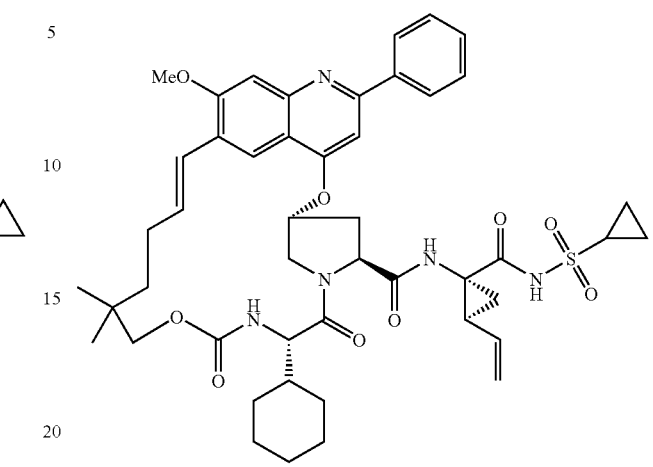
III-89
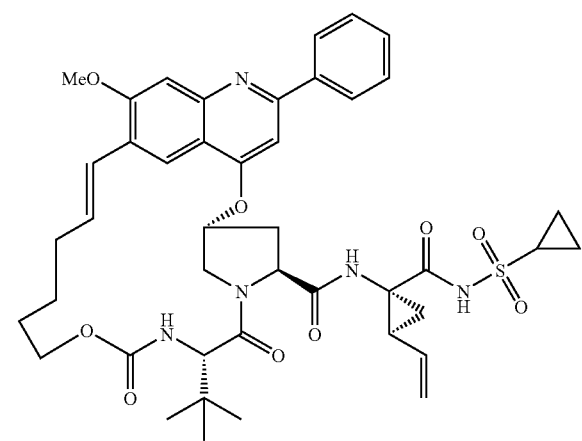
III-90
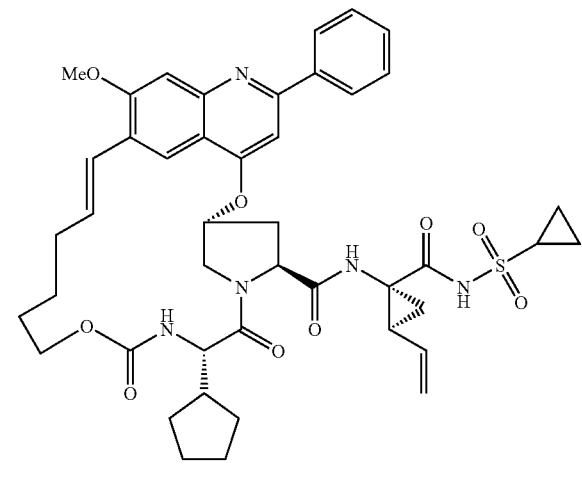

III-91
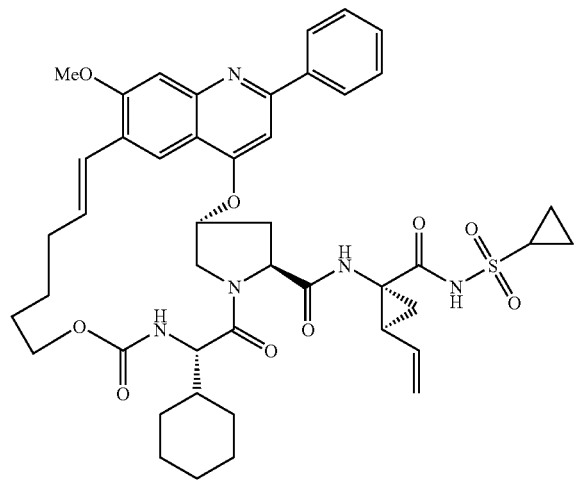
III-94
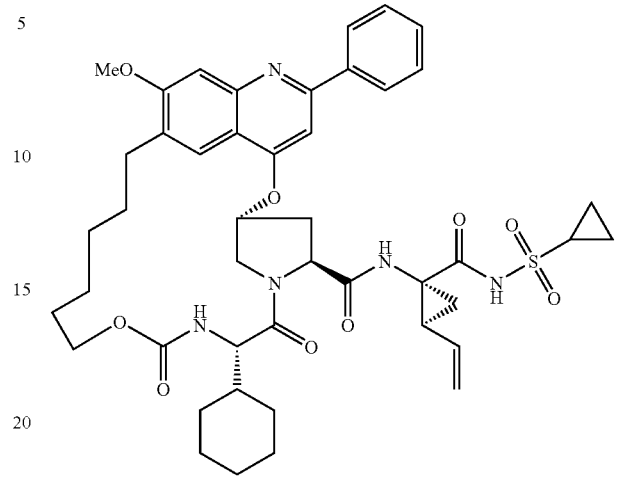
III-92
III-95
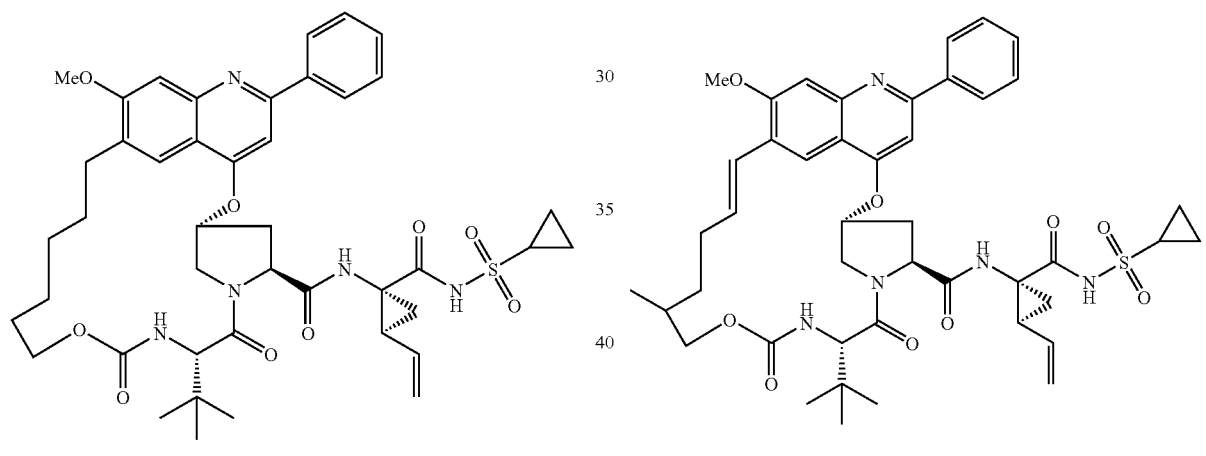
III-93
III-96
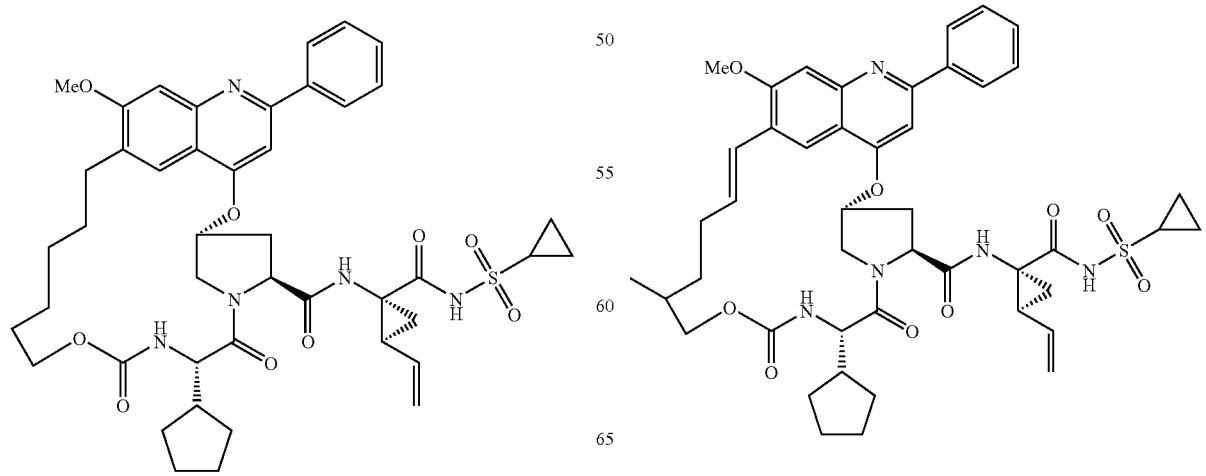

III-97

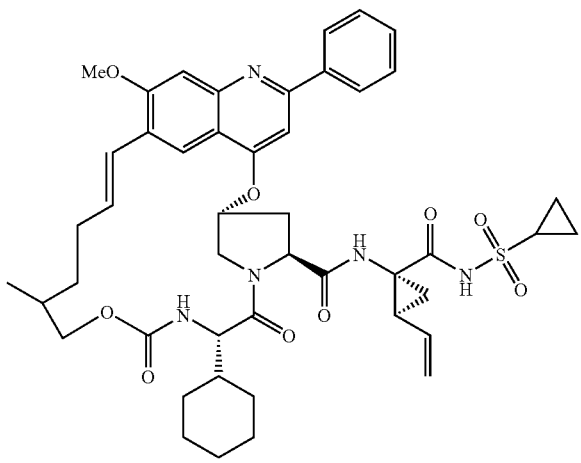

III-98

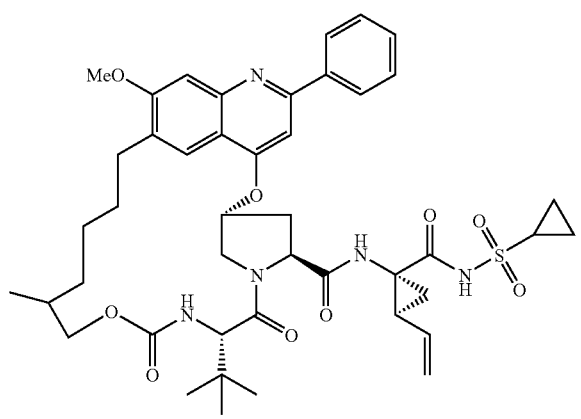

Other embodiments of the present invention include the following:

(a) A pharmaceutical composition comprising an effective amount of a compound of formula I, II or III and a pharmaceutically acceptable carrier.

(b) The pharmaceutical composition of (a), further comprising a second therapeutic agent selected from the group consisting of a HCV antiviral agent, an immunomodulator, and an anti-infective agent.

(c) The pharmaceutical composition of (b), wherein the HCV antiviral agent is an antiviral selected from the group consisting of a HCV protease inhibitor and a HCV NS5B polymerase inhibitor.

(d) A pharmaceutical combination which is (i) a compound of formula I, II or III and (ii) a second therapeutic agent selected from the group consisting of a HCV antiviral agent, an immunomodulator, and an anti-infective agent; wherein the compound of formula I, II or III and the second therapeutic agent are each employed in an amount that renders the combination effective for inhibiting HCV NS3 protease, or for treating or preventing infection by HCV.

(e) The combination of (d), wherein the HCV antiviral agent is an antiviral selected from the group consisting of a HCV protease inhibitor and a HCV NS5B polymerase inhibitor.

(f) A method of inhibiting HCV NS3 protease in a subject in need thereof which comprises administering to the subject an effective amount of a compound of formula I, II or III.

(g) A method of preventing or treating infection by HCV in a subject in need thereof which comprises administering to the subject an effective amount of a compound of formula I, II or III.

(h) The method of (g), wherein the compound of formula I, II or III is administered in combination with an effective amount of at least one second therapeutic agent selected from the group consisting of a HCV antiviral agent, an immunomodulator, and an anti-infective agent.

(i) The method of (h), wherein the HCV antiviral agent is an antiviral selected from the group consisting of a HCV protease inhibitor and a HCV NS5B polymerase inhibitor.

(j) A method of inhibiting HCV NS3 protease in a subject in need thereof which comprises administering to the subject the pharmaceutical composition of (a), (b), or (c) or the combination of (d) or (e).

(k) A method of preventing or treating infection by HCV in a subject in need thereof which comprises administering to the subject the pharmaceutical composition of (a), (b), or (c) or the combination of (d) or (e).

The present invention also includes a compound of the present invention (i) for use in, (ii) for use as a medicament for, or (iii) for use in the preparation of a medicament for: (a) inhibiting HCV NS3 protease, or (b) preventing or treating infection by HCV. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "haloalkyl" refers to an alkyl group wherein a hydrogen has been replaced by a halogen. The term "alkoxy" refers to an "alkyl-O—" group.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The terms "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "cycloalkyl-O—" group.

The term "halogen" (or "halo") refers to fluorine, chlorine, bromine and iodine (alternatively referred to as fluoro, chloro, bromo, and iodo).

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (e.g., $R_7$ and $R_{10}$) occurs more than one time in any constituent or in formula I, II or III or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula I, II or III is a reference to the compound per se, or to any one of its tautomers per se, or to mixtures of two or more tautomers.

The compounds of the present inventions are useful in the inhibition of HCV protease (e.g., HCV NS3 protease) and the prevention or treatment of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus the compounds of this invention are commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that, is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and preventing or treating HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like)

can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO-99/07733, WO 99/07734, WO 99/38888, WO 99/50230, WO 99/64442, WO 00/09543, WO-00/59929, GB-2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO-97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action*, 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'Kuru, et al., *J. Org. Chem.*, 62: 1754-1759 (1997); M. S. Wolfe, et al., *Tetrahedron Lett.*, 36: 7611-7614 (1995); U.S. Pat. No. 3,480, 613 (25 Nov. 1969); International Publication Number WO-01/90121 (29 Nov. 2001); International Publication Number WO 01/92282 (6 Dec. 2001); and International Publication Number WO 02/32920 (25 Apr. 2002); and International Publication Number WO 04/002999 (8 Jan. 2004); and International Publication Number WO 04/003000 (8 Jan. 2004); and International Publication Number WO 04/002422 (8 Jan. 2004); the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425 (4 Jul. 2002), assigned to Mitsubishi Pharma Corp.; WO 01/79246, WO-02/32920, and WO 02/48165 (20 Jun. 2002), assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), assigned to Hoffmann-LaRoche; U.S. 2002/0019363 (14 Feb. 2002);

WO 02/100415 (19 Dec. 2002); WO 03/026589 (3 Apr. 2003); WO 03/026675 (3 Apr. 2003); WO 03/093290 (13 Nov. 2003); US 2003/0236216 (25 Dec. 2003); US 2004/0006007 (8 Jan. 2004); WO 04/011478 (5 Feb. 2004); WO 04/013300 (12 Feb. 2004); US 2004/0063658 (1 Apr. 2004); and WO 04/028481 (8 Apr. 2004); the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in WO 02/057287, U.S. Pat. No. 6,777,395, WO 02/057425, US 2004/0067901, WO 03/068244, WO 2004/000858, WO 04/003138 and WO 2004/007512; the content of each is incorporated herein by reference in its entirety. Other such HCV polymerase inhibitors include, but are not limited to, valopicitabine (NM-283; Idenix) and 2'-F-2'-beta-methyl-cytidine (see also WO 2005/003147, assigned to Pharmasset, Ltd.).

In one embodiment, nucleoside HCV NS5B polymerase inhibitors that are used in combination with the present HCV NS3 protease inhibitors are selected from the following compounds:

4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C$_{12}$-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C, 2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S. P. A.; WO 02/20497 (3 Mar. 2002); WO 2005/016927 (in particular JTK003), assigned to Japan Tobacco, Inc.; the content of each is incorporated herein by reference in its entirety; and HCV-796 (Viropharma Inc.).

In one embodiment, non-nucleoside HCV NS5B polymerase inhibitors that are used in combination with the present HCV NS3 protease inhibitors are selected from the following compounds:

14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; M-(11-carboxy-14-cyclohexyl-7,8-dihydro-6H-indolo[1,2-e][1,5]benzoxazocin-7-yl)-N,N-dimethylethane-1,2-diaminium bis(trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11- carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

The above tetracyclic indole-based HCV NS5B polymerase inhibitors may be obtained following methods A-E as outlined below, wherein different variables may be selected in accordance with the specific tetracyclic indole compound to be prepared:

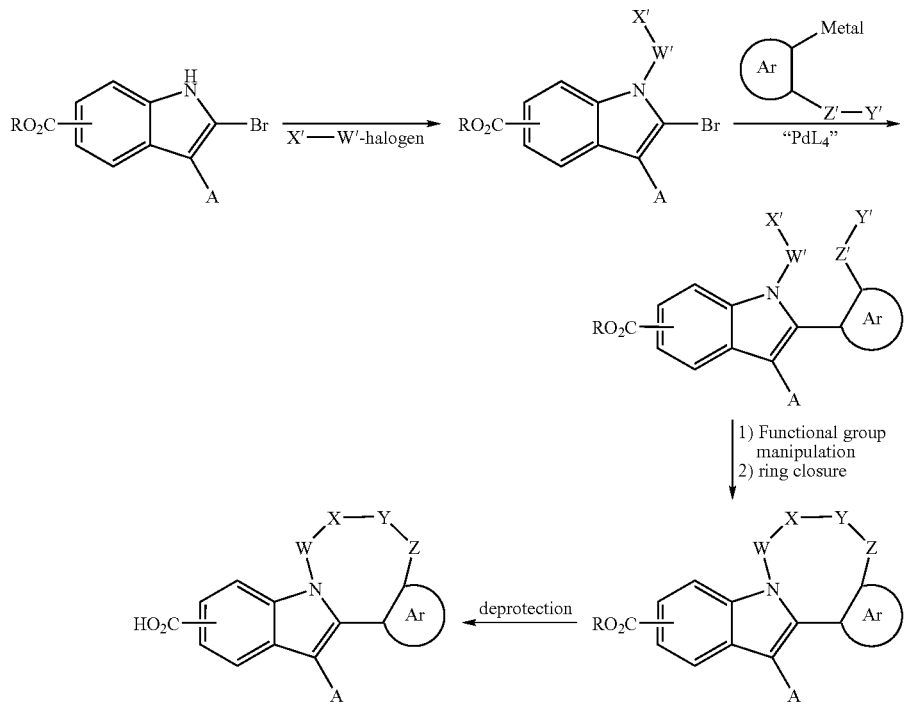

2-Bromoindole intermediate (prepared as described in published International patent application WO 2004087714) was functionalized on the indole nitrogen to introduce precursor functionality W'/X' to either or both of the elements W/X of the tether. Pd-mediated cross-coupling methodology (eg, Suzuki, Stille etc) then brought in the C2 aromatic bearing pre-cursor functionality Z'/Y' to either or both of the elements Z/Y of the tether. Functional group manipulation followed by ring closure afforded the tetracyclic system. Ester deprotection then yielded the target indole carboxylic acids, with the C2 aromatic tethered to the indole nitrogen.

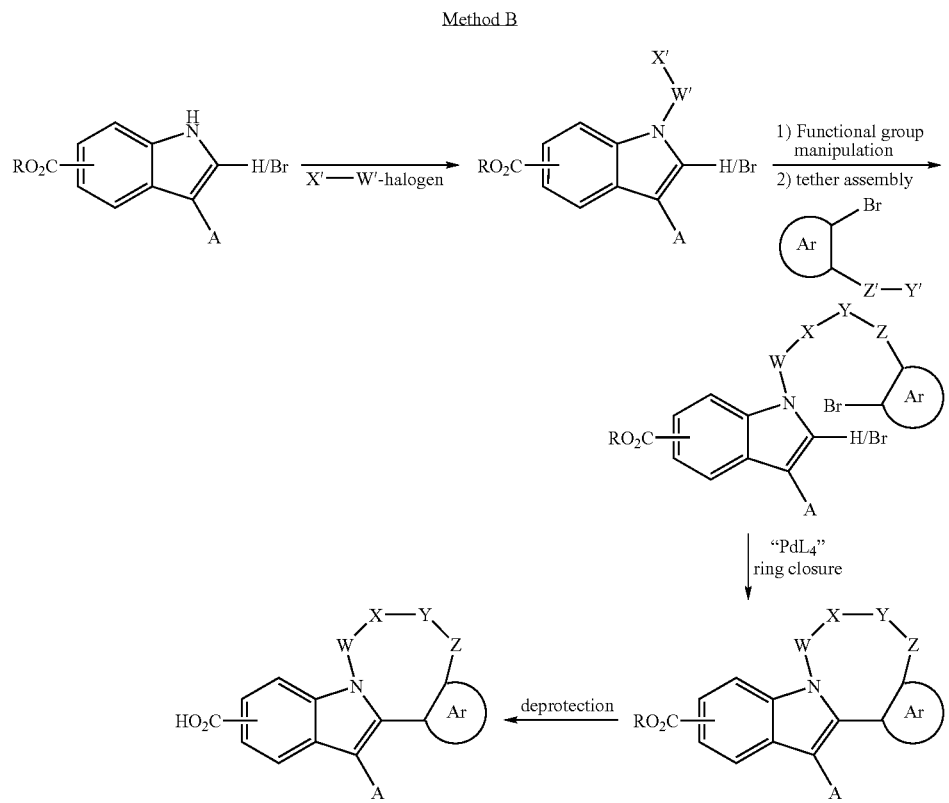
Following tether assembly out to the appropriate 2-haloaromatic, Pd-mediated ring closure afforded the fused tetracyclic system. Ester deprotection then yielded the target indole carboxylic acids, with the C2 aromatic tethered to the indole nitrogen.
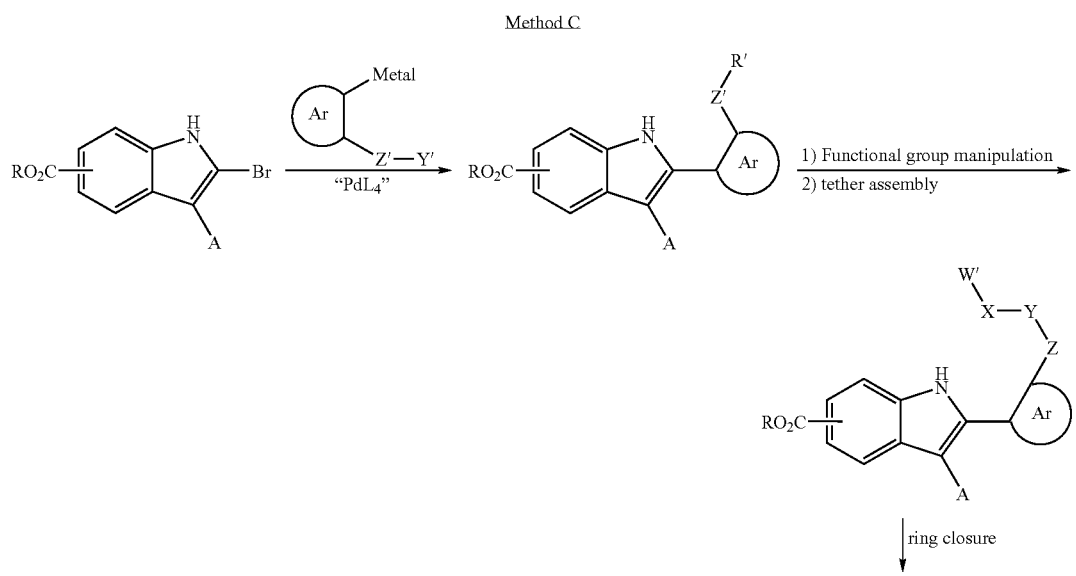

-continued

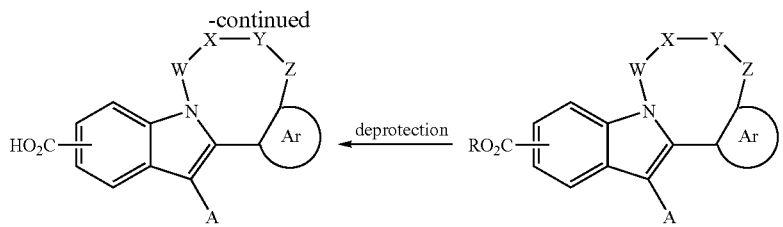

The C2 aromatic was introduced at the outset via Pd-mediated cross-coupling methodology (Suzuki, Stille etc). The tether was then built up, with cyclisation onto the indole nitrogen finally closing the ring. Ester deprotection then yielded the target indole carboxylic acids, with the C2 aromatic tethered to the indole nitrogen.

Method D

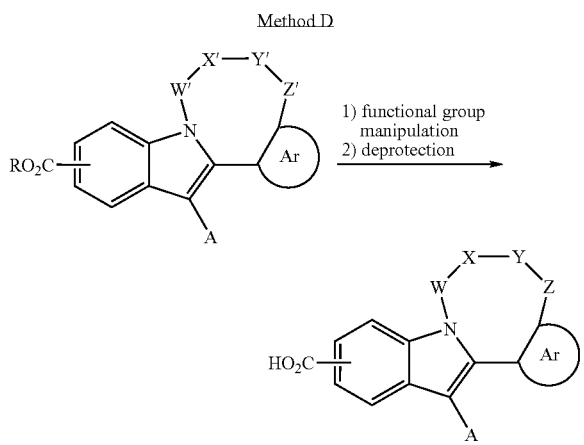

Fused tetracyclic intermediates arising from Methods A-C underwent manipulation of the functionality in the tether prior to ester deprotection to yield the target C2-tethered indole carboxylic acids.

Method E

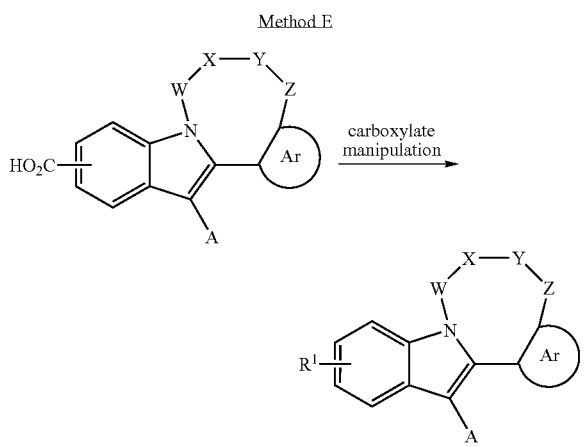

C2-tethered indole carboxylic acids arising from Methods A-D were further derivatised through manipulation of the carboxylate functionality to give compounds bearing a carboxylate replacement or carboxamide. During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The HCV NS3 protease inhibitory activity of the present compounds may be tested using assays known in the art. One such assay is HCV NS3 protease time-resolved fluorescence (TRF) assay as described in Example 9. Compounds useful as HCV NS3 protease inhibitors would have a Ki less than 50 μM, more preferably less than 10 μM.

The present invention also includes processes for making compounds of formula I, II or III. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice. The examples are not to be construed as limitations on the scope or spirit of the invention.

General Description of Synthesis

The compounds of the present invention may be synthesized as outlined in the general schemes 1-3 and schemes 4-7. Compounds wherein $R_1$ is $CONHP(O)R_{11}R_{12}$ or $P(O)R_{11}R_{12}$ can be made analogously according to the methods described in WO 2006/020276.

Scheme 1 outlines the synthesis of the proline portion of the molecule. An appropriately protected 4-hydroxyproline derivative (for example, a carbamate protected nitrogen and an ester protected acid can be reacted with an appropriately substituted 4-hydroxyquinoline in a single step via a Mitsunobu reaction (Mitsunobu, *Synthesis* 1981, 1-28). Alternatively, a two step process can be utilized in which the alcohol is converted to a leaving group such as a mesylate, benzenesulfonate, toluenesulfonate or 4-bromobenzenesulfonate in the first step by reaction with the appropriate sulfonyl chloride in a solvent with an amine base as acid scavenger. In a second step the leaving group is displaced with an appropriately substituted quinoline in a number of organic solvents (for example DMF, acetonitrile or N-methylpyrrolidinone) with either an organic or inorganic base (for example $K_2CO_3$ or $Cs_2CO_3$). The alkenyl functionality on the quinoline may be introduced at this or a later stage by palladium catalyzed reaction of a halide substituent such as bromide or iodide, or other functionality such as a triflate with an organometallic reagent such as a vinyl or allyltrialkyltin. Alternatively, the alkenyl functionality may be introduced prior to the reaction with protected prolinol.

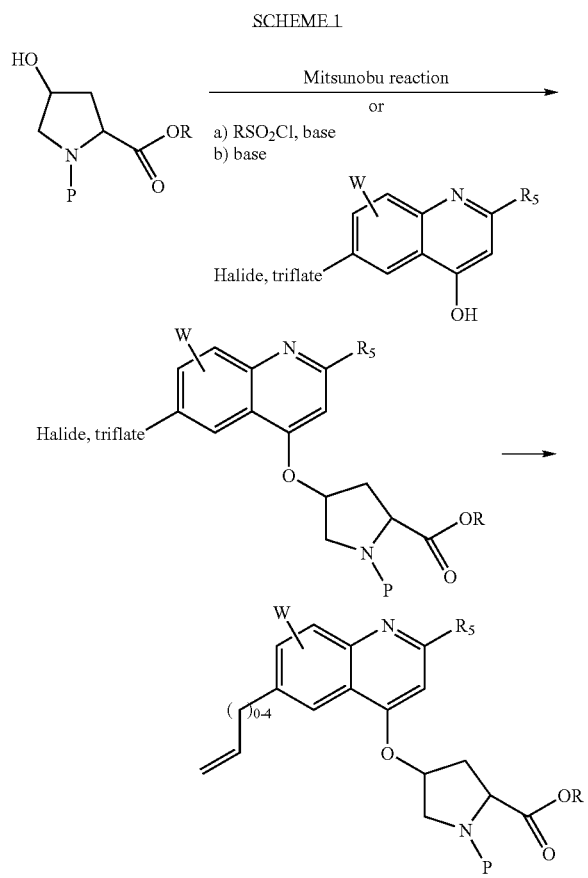

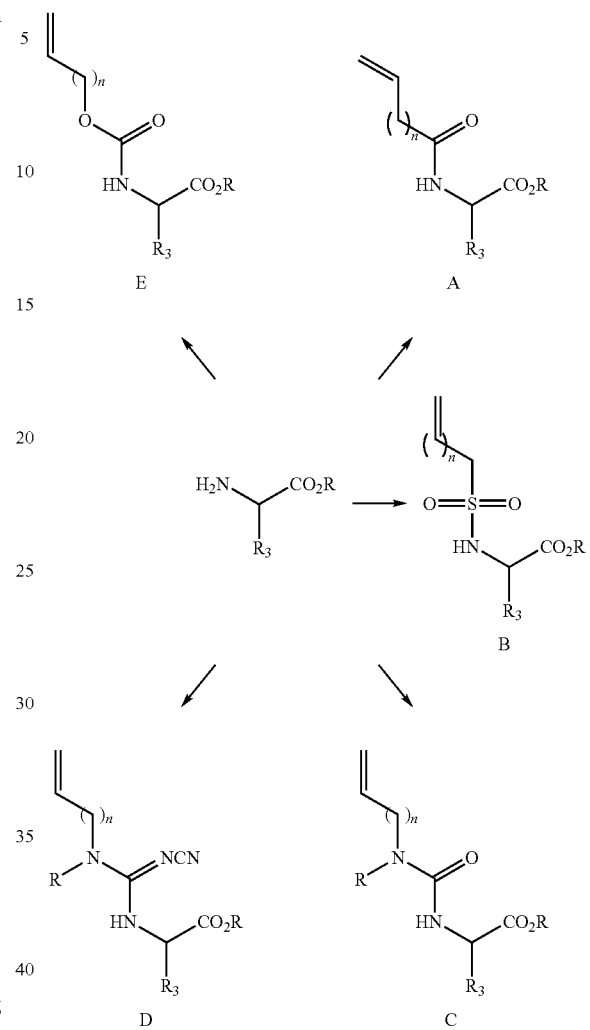

Scheme 2 describes the synthesis of the olefin containing amino acid portion. An amino acid in which the acid functionality is protected as an ester can be converted to amides A by coupling an olefinic carboxylic acid utilizing a wide range of peptide coupling agents known to those skilled in the art such as DCC, EDC, BOP, TBTU, etc. Preparation of the sulfonamides B can be accomplished by reaction with the appropriate sulfonyl chloride in an organic solvent (e.g. THF) with an amine base as scavenger. Urea derivatives C may be prepared by reacting the aminoester with a reagent such as carbonyldiimidazole, to form an intermediate isocyanate (Catalano et al., WO 03/062192) followed by addition of a second olefin containing amine. Alternatively, phosgene, diphosgene or triphosgene may be used in place of carbonyldiimidazole. Cyanoguanidine derivatives D can be prepared by reaction of the amino acid ester with diphenyl C-cyanocarbonimidate in an organic solvent, followed by addition of a second olefin containing amine. Carbamate derivatives E may be prepared by reacting an olefin containing alcohol with carbonyldiimidazole (or phosgene, triphosgene or diphosgene) in an organic solvent, followed by addition of the amino ester.

Following functionalization of the amine, the ester can be hydrolyzed under a range of basic conditions known to those skilled in the art (T. W. Greene, *Protective Groups in Organic Synthesis,* 3rd Edition, John Wiley and Sons, 1999).

Deprotection of the carbamate protecting group on the proline portion may be carried out by a variety of methods known to persons skilled in the art (T. W. Greene, *Protective Groups in Organic Synthesis,* 3rd Edition, John Wiley and Sons, 1999).

To complete the synthesis of the compounds of this invention, the amino acid derivative can be coupled to the proline derivative via a wide range of peptide coupling reagents such as DCC, EDC, BOP, TBTU etc. Macrocyclization is then achieved by an olefin metathesis using a range of catalysts that have been described in the literature for this purpose. At this stage the olefinic bond produced in the ring closing metathesis may be optionally hydrogenated to give a saturated linkage or functionalized in alternative ways such as cyclopropanation. The proline ester is then hydrolyzed under basic conditions and coupled with the cyclopropylamino acid ester (the appropriate alkenyl or alkylcyclopropane portion of the molecule can be prepared as described previously (Llinas-Brunet et al., U.S. Pat. No. 6,323,180)) and subjected to an additional basic hydrolysis step to provide the final compounds.

SCHEME 3

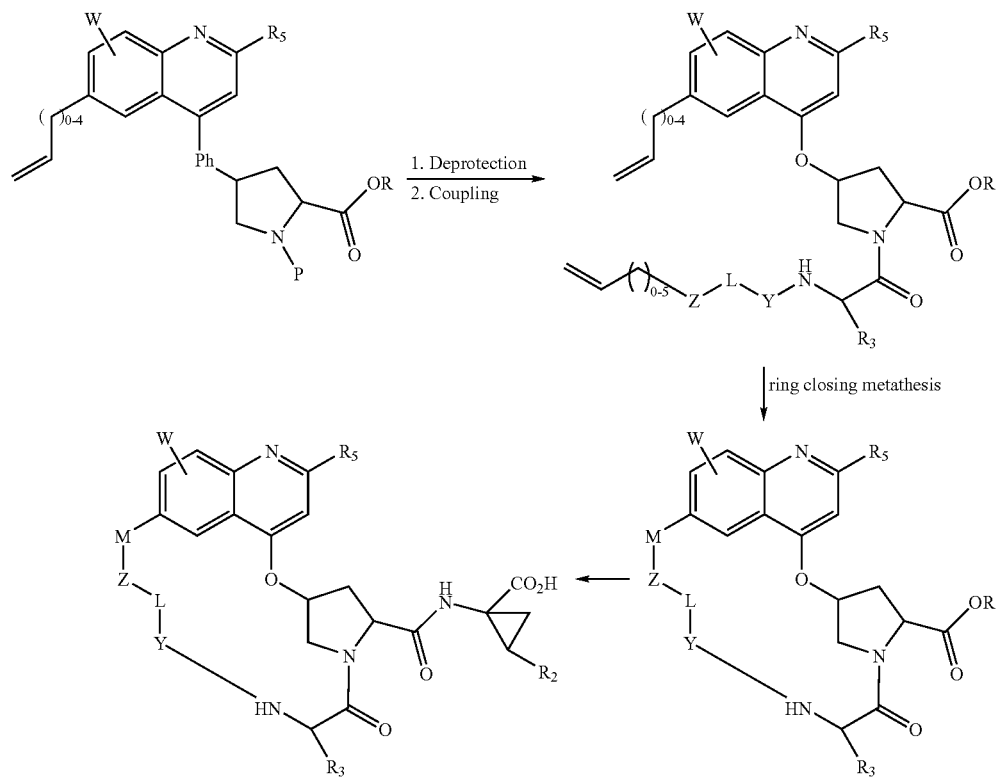

Olefin-metathesis catalysts include the following Ruthenium-based species: F. Miller et al., 118 *J. Am. Chem. Soc.* 9606 (1996); G. Kingsbury et al., 121 *J. Am. Chem. Soc.* 791 (1999); H. Scholl et al., *Org. Lett.* 953 (1999); U.S. Patent Application Publication US2002/0107138; K. Furstner et al., 64 *J. Org. Chem.* 8275 (1999). The utility of these catalysts in ring-closing metathesis is well known in the literature (e.g. Trnka and Grubbs, 34 *Acc. Chem. Res.* 18 (2001).

F
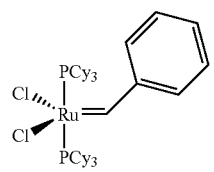

G
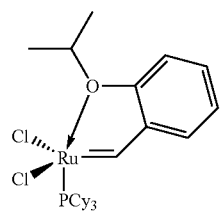

-continued

H
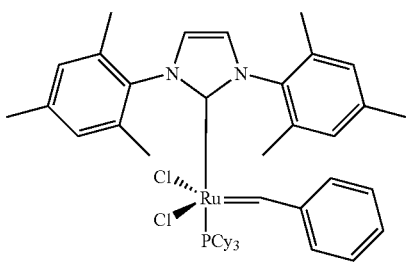

J
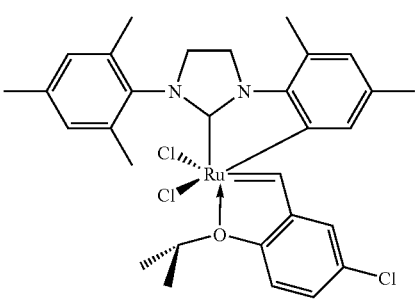

Zhan ruthenium metathesis catalyst RC-303 (Zhan catalyst 1B, RC-303, Zannan Pharma Ltd.)

SCHEME 4
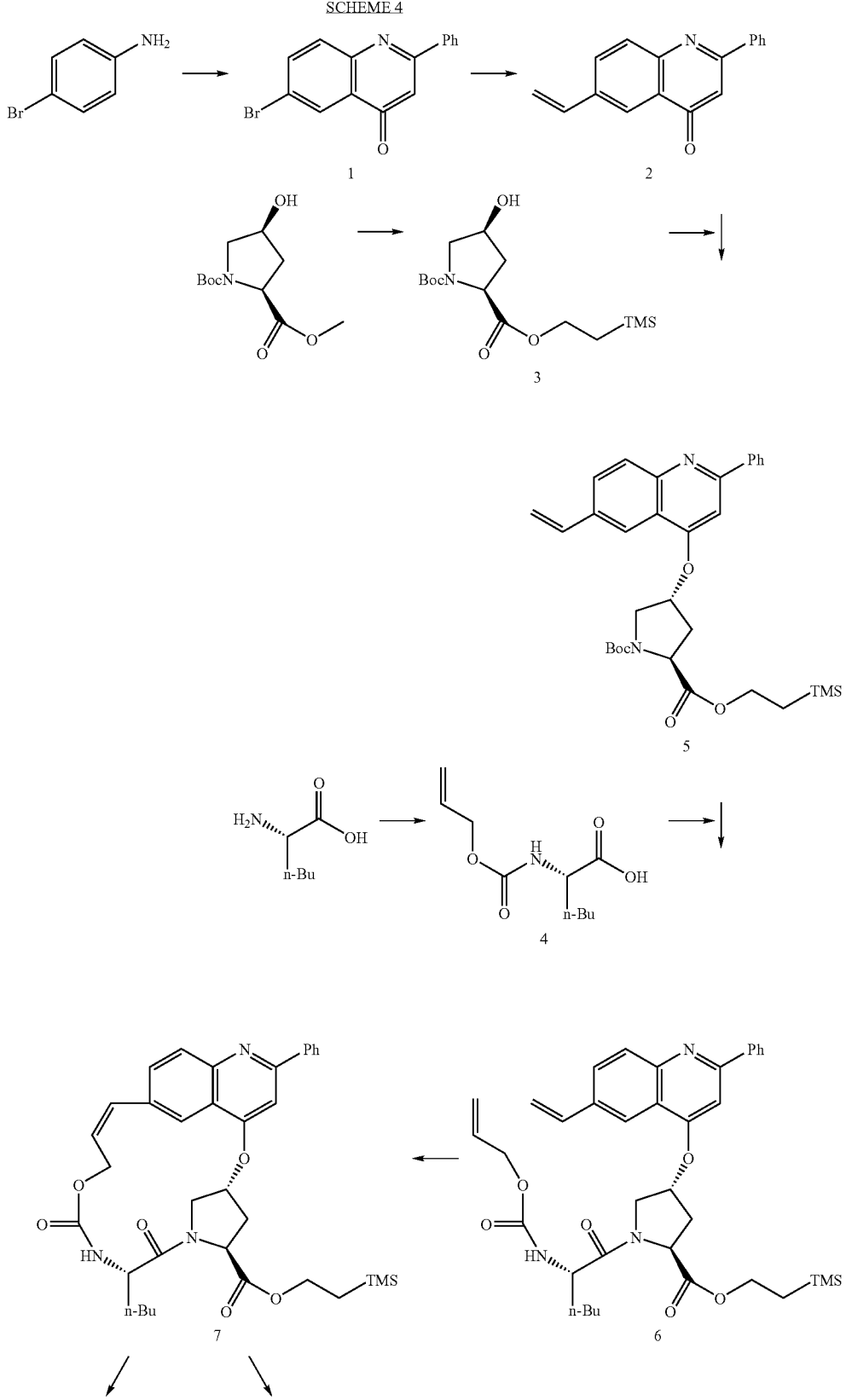

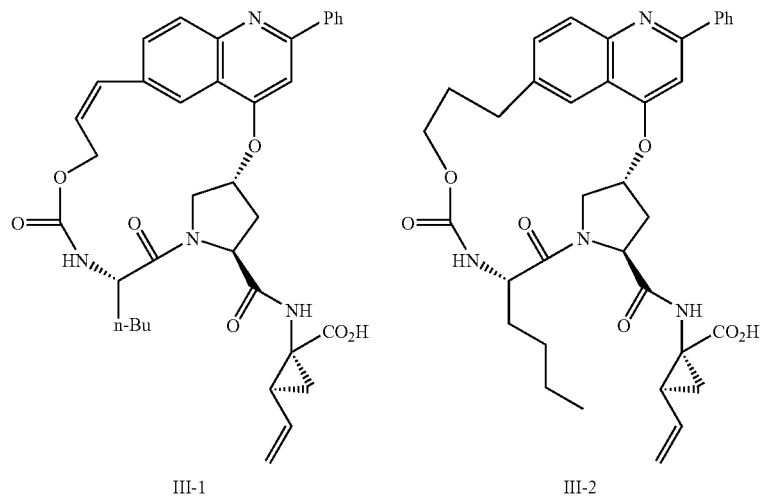

III-1    III-2

| List of Abbreviations | |
|---|---|
| DCM | Dichloromethane |
| EtOAc | Ethyl Acetate |
| DMSO | Dimethyl Sulfoxide |
| THF | Tetrahydrofuran |
| PhMe | Toluene |
| $MgSO_4$ | Magnesium Sulfate |
| $PPh_3$ | Triphenylphosphine |
| DMF | Dimethylformamide |
| TBTU | O-Benzotriazol-1-yl-N,N,N',N'-tetramethyluronium tetrafluoroborate |
| TBAF | Tetrabutylammonium fluoride |
| MeOH | Methanol |
| VinylMgBr | Vinylmagnesium bromide |
| $Et_3N$ | Triethylamine |
| Nle | Norleucine |
| EtOH | Ethanol |
| HOAc | Acetic acid |
| $CH_3CN$ | Acetonitrile |
| DIPEA | Diisoproylethylamine |
| HCl | Hydrochloric acid |
| NaOH | Sodium hydroxide |
| DBU | 1,8-Diazabicyclo[5.4.0]undec-7-ene |
| DABCO | 1,4-Diazabicyclo[2.2.2]octane |
| Brosyl chloride | 4-Bromophenyl sulfonylchloride |
| $NaHCO_3$ | Sodium bicarbonate |
| $Na_2SO_4$ | Sodium sulfate |
| EDC | N-(3-Dimethylaminopropyl)-N'-ethylcarbodiimide |
| HOAt | 1-Hydroxy-7-azabenzotriazole |
| LiOH | Lithium hydroxide |
| Pd/C | Palladium on carbon |
| TBTU | O-Benzotriazol-1-yl-N,N,N',N'-tetramethyluronium tetrafluoroborate |
| RT | room temperature |

EXAMPLE 1

(1RS,2SR)-1-({[(2R,4S,7S)-7-Butyl-6,9-dioxo-18-phenyl-3,4,6,7,8,9-hexahydro-2H,11H-14,16-etheno-2,5-methanopyrido[4,3-k][1,10,3,6]dioxadiazacyclo-heptadecin-4-yl]carbonyl}amino)-2-vinylcyclopropanecarboxylic acid (III-1)

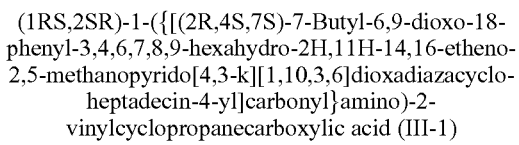

III-1

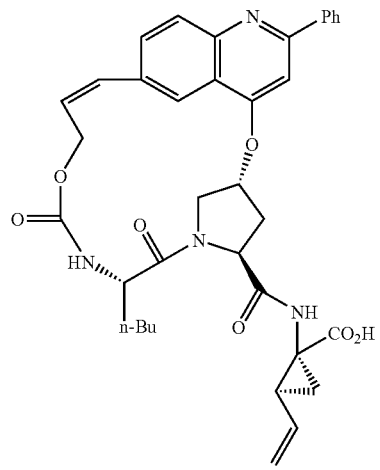

Step 1: 6-Bromo-2-phenylquinolin-4(1H)-one

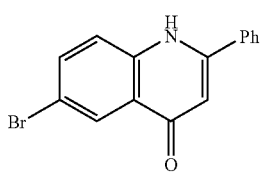

1

A mixture of 4-bromoaniline (7.0 g, 40.7 mmol), ethyl benzoylacetate (14.09 mL, 81.4 mmol), and polyphosphoric acid (15.95 g, 162.7 mmol) was heated without solvent to 150° C. for 3 h. After 3 h, the reaction was cooled to RT, and the mixture was quenched with 4 N HCl (200 mL), which caused an orange cake to form. This solid was filtered, and to this was added 2N NaOH (200 mL). The majority of the solid did not dissolve, and was filtered off. The solid was washed with water (200 mL) and a mixture of 1:1 acetone/DCM (200 mL), and stored under vacuum overnight to give 6.52 g (53% yield) of ~95% (by LC-MS) pure 6-bromo-2-phenylquinolin-4(1H)-one. Further purification can be accomplished by recrystallization with n-butoxyethanol to yield analytically pure material. $^1$H NMR (400 MHz, DMSO-$d_6$) ppm: 11.87 (br s, 1H), 8.18 (d, J=2.4 Hz, 1H), 7.82 (m, 3H), 7.73 (d, J=8.8 Hz, 1H), 7.60 (m, 3H), 6.39 (d, J=1.6 Hz, 1H). LRMS (CI, [M+H]) Calc'd=300.1. found=300.1.

Step 2: 2-Phenyl-6-vinylquinolin-4(1H)-one

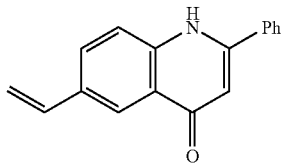

2

To a solution of 6-bromo-2-phenylquinolin-4(1H)-one 1 (1.5 g, 5.0 mmol) in DMSO (60 mL) was added vinyltributyl tin (1.75 mL, 6.0 mmol) and tetrakis-triphenylphosphine palladium (116 mg, 0.1 mmol). The mixture was then heated to 100° C. for 20 h, at which time, LC-MS revealed the disappearance of starting material. The reaction was then poured into a mixture of EtOAc (200 mL) and water (400 mL) which caused a grayish solid to precipitate. This solid was collected and dried under vacuum in a desiccator over night to yield 1.21 g (97% yield) of 2-phenyl-6-vinylquinolin-4(1H)-one which was pure by $^1$H NMR and LC-MS. $^1$H NMR (400 MHz, DMSO-$d_6$) ppm: 11.75 (br s, 1H), 8.08 (s, 1H), 7.85 (m, 3H), 7.74 (d, J=8.8 Hz, 1H), 7.59 (m, 3H), 6.88 (dd, J=17.6 Hz, 10.8 Hz, 1H), 6.34 (s, 1H), 5.90 (d, J=17.6 Hz, 1H), 5.30 (d, J=10.8 Hz, 1H). LRMS (CI, [M+H]) Calc'd=248.2. found=248.2. HRMS (APCI, [M+H]$^+$) Calc'd for $C_{15}H_{11}BrNO$: 248.1070. found: 248.1068.

Step 3: 1-tert-Butyl 2-[2-(trimethylsilyl)ethyl] (2S, 4S)-4-hydroxypyrrolidine-1,2-dicarboxylate

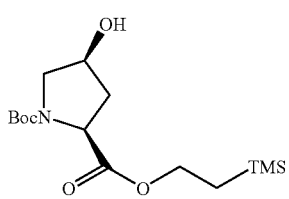

3

To a solution of 1-tert-butyl 2-methyl (2S,4S)-4-hydroxypyrrolidine-1,2-dicarboxylate (1.0 g, 4.08 mmol) in THF (30 mL) and water (6 mL) cooled to 0° C. was added a 1 M solution of NaOH (6.12 mL, 6.12 mmol). The mixture was stirred at this temperature for 2 h. At this time, TLC (100% Et$_2$O) indicated complete consumption of the starting material and formation of a more polar compound (KMnO$_4$ stain). The THF was then removed in vacuo, and the pH of the water layer was adjusted to 2-3 with 1 N HCl. The mixture was then extracted with EtOAc, dried over MgSO$_4$, and the solvent was removed in vacuo. LC-MS indicated that the major product had the desired mass. The crude compound was then taken up in PhMe (30 mL), O-2-trimethylsilyl-N,N'-diisopropylisourea (1.99 g, 8.15 mmol) was added, and the mixture was refluxed for 2 h. At this time, 30% EtOAc/hexanes (10 mL) was added and the mixture was filtered. The solvent was then removed in vacuo, and the crude product was purified on silica (40% EtOAc/hex) to yield 1.23 g (91% yield) of 1-tert-butyl 2-[2-(trimethylsilyl)ethyl] (2S,4S)-4-hydroxypyrrolidine-1,2-dicarboxylate (N-Boc-Hyp-OTMSE). $^1$H NMR (400 MHz, CDCl$_3$) ppm: mixture of amide rotamers: 4.36-4.21 (m, 4H), 3.72 (d, J=12 Hz, 0.5H), 3.63 (d, J=12 Hz, 0.5H), 3.57-3.49 (m, 1.5H). 3.50 (d, J=10.4 Hz, 0.5H), 2.31 (m, 1H), 2.07 (m, 1H), 1.46 and 1.43 (2 s, 9H), 1.03 (m, 2H), 0.06 and 0.04 (2 s, 9H). HRMS (APCI, [M+H]$^+$) Calc'd for $C_{15}H_{30}NO_5Si$: 332.1888. found: 332.1895.

Step 4: N-[(Allyloxy)carbonyl]-L-norleucine

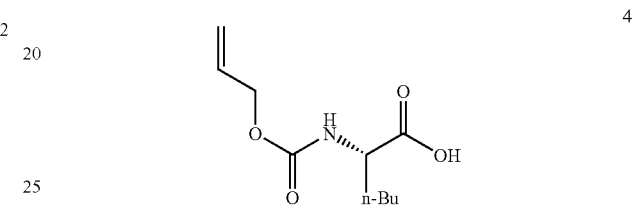

4

To a solution of L-norleucine (1.0 g, 7.6 mmol) was added a 1M solution of NaOH (7.8 mL, 7.8 mmol). The mixture was then cooled to 0° C., and allyl chloroformate and additional 1M NaOH (7.8 mL, 7.8 mmol) were added simultaneously. Following addition, the solution was warmed to RT, and stirred for a further 45 min. The mixture was then extracted with ether. The aqueous layer was then acidified with 4 N HCl to pH~5. The mixture was then further extracted with DCM. The combined organic fractions were dried over MgSO$_4$, and the solvent was removed in vacuo to yield 1.54 g (94% yield) pure product N-[(allyloxy)carbonyl]-L-norleucine 4 (N-alloc-Nle-OH). $^1$H NMR (400 MHz, MeOH-d) ppm: 7.21 (br d, J=8 Hz, 1H), 5.93 (m, 1H), 5.31 (dd, J=17.6 Hz, 1.6 Hz, 1H), 5.17 (dd, J=10.6 Hz, 1.6 Hz, 1H), 4.54 (d, J=5.6 Hz, 2H), 4.10 (m, 1H), 1.82 (m, 1H), 1.66 (m, 1H), 1.37 (m, 4H), 0.92 (t, J=6.8 Hz, 3H). LRMS (CI, [M+H]) Calc'd=216.2. found=216.2. HRMS (APCI, [M+H]$^+$) Calc'd for $C_{10}H_{18}NO_4$: 216.1231. found: 216.1235.

Step 5: 1-tert-Butyl 2-[2-(trimethylsilyl)ethyl] (2S, 4R)-4-[(2-phenyl-6-vinylquinolin-4-yl)oxy]pyrrolidine-1,2-dicarboxylate

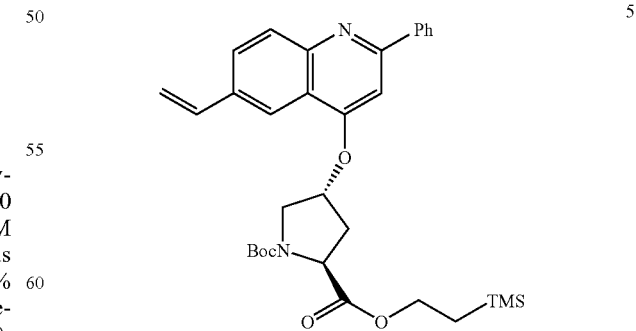

5

To a solution of 1-tert-butyl 2-[2-(trimethylsilyl)ethyl] (2S, 4S)-4-hydroxypyrrolidine-1,2-dicarboxylate 3 (1.0 g, 3.02 mmol) in THF (30 mL) was added 2-phenyl-6-vinylquinolin-4(1H)-one 2 (0.78 g, 3.17 mmol) and PPh$_3$ (1.19 g, 4.52 mmol). The flask was then cooled to 0° C. and diethylazodicarboxylate (0.713 mL, 4.52 mmol) was added slowly. The mixture was then warmed to RT and stirred overnight (16 h). At this time, the starting material to product ratio was 2:1. The reaction was re-cooled to 0° C., and additional PPh$_3$ (1.19 g, 4.52 mmol) and diethylazodicarboxylate (0.713 mL, 4.52 mmol) were added. After stirring for an additional 19 h, only a small amount of starting material remained. Silica gel was then added to the reaction and the mixture was filtered through silica gel with EtOAc as the eluent. The crude mixture was then purified on silica (5-40% EtOAc/hexanes) to yield 0.85 g (50% yield) of 1-tert-butyl 2-[2-(trimethylsilyl)ethyl] (2S,4R)-4-[(2-phenyl-6-vinylquinolin-4-yl)oxy]pyrrolidine-1,2-dicarboxylate 5. $^1$H NMR (500 MHz, CDCl$_3$) ppm: mixture of amide rotamers: 8.43 (m, 1H), 8.13-8.09 (m, 2H), 7.92 and 7.91 (2 br s, 2H), 7.56 (m, 3H), 7.12 and 7.11 (2 br s, 1H), 6.92 (br dd, J=17.5 Hz, 10.5 Hz, 1H), 6.02 (d, J=17.5 Hz, 1H), 5.58 (d, J=10.5 Hz, 1H), 5.53 and 5.49 (2 br s, 1H), 4.64 and 4.54 (2 app t, J=7.5 Hz, 1H), 4.27 (app t, J=7 Hz, 2H), 4.07 (m, 1.5H), 3.89 (br d, J=13 Hz, 0.5H), 2.81 (m, 1H), 2.55 (m, 1H), 1.47 and 1.45 (2 s, 9H), 1.04 (m, 2H), 0.07 and 0.06 (2 s, 9H). LRMS (CI, [M+H]) Calc'd=561.4. found=561.4. HRMS (APCI, [M+H]$^+$) Calc'd for C$_{32}$H$_{41}$N$_2$O$_5$Si: 561.2779. found: 561.2749.

Step 6: 2-(Trimethylsilyl)ethyl N-[(allyloxy)carbonyl]-L-norleucyl-(4R)-4-[(2-phenyl-6-vinylquinolin-4-yl)oxy]-L-prolinate

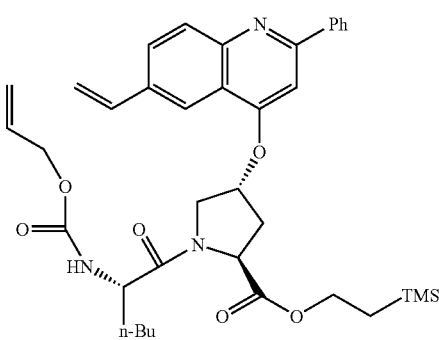

To a flask containing 1-tert-butyl 2-[2-(trimethylsilyl)ethyl] (2S,4R)-4-[(2-phenyl-6-vinylquinolin-4-yl)oxy]pyrrolidine-1,2-dicarboxylate 5 (45 mg, 0.08 mmol) was added a 4 M solution of HCl in dioxane (1.4 mL, 5.6 mmol). After 1 h, LC-MS analysis indicated complete consumption of the starting material (5) and formation of the desired -Boc product. The volatile components were then removed in vacuo, and the crude material was taken up in DMF (1 mL). To this mixture was added alloc-Nle-OH (4) (26 mg, 0.12 mmol), DIPEA (0.144 mL, 0.8 mmol), and TBTU (39 mg, 0.12 mmol). After stirring at RT for 30 min, complete consumption of the amine was evidenced via LC-MS. The reaction mixture was then worked-up with 1N HCl and EtOAc. The organic layer was washed with brine and dried over MgSO$_4$. The solvent was then removed in vacuo and the crude product was purified on silica (10-50% EtOAc/hexanes) to yield 50 mg (95% yield) of 2-(trimethylsilyl)ethyl N-[(allyloxy)carbonyl]-L-norleucyl-(4R)-4-[(2-phenyl-6-vinylquinolin-4-yl)oxy]-L-prolinate 6. $^1$H NMR (500 MHz, CDCl$_3$) ppm: mixture of amide rotamers: 8.07 (m, 3H), 7.97 (br s, 1H), 7.88 (m, 1H), 7.54-7.47 (m, 3H), 7.07 (s, 1H), 6.92 (dd, J=17.5 Hz, 10.5 Hz, 1H), 5.90 (d, J=17.5 Hz, 1H), 5.83 (m, 1H), 5.43-5.63 (m, 3H), 5.25-5.13 (m, 2H), 4.79 (app t, J=8 Hz, 1H), 4.65-4.37 (m, 4H), 4.26 (m, 2H), 4.10 and 4.08 (2 d, J=4.0 Hz and 4.5 Hz, 1H), 2.78 (m, 1H), 2.42 (m, 1H), 1.83 (m, 1H), 1.63 (m, 1H), 1.44-1.33 (m, 4H), 1.05-0.98 (m, 2H), 0.92 (m, 3H), 0.05 (s, 9H). LRMS (CI, [M+H]) Calc'd=658.4. Found=658.4. HRMS (APCI, [M+H]$^+$) Calc'd for C$_{37}$H$_{48}$N$_3$O$_6$Si: 658.3307. found: 658.3348.

Step 7: 2-(Trimethylsilyl)ethyl (2R,4S,7S)-7-butyl-6,9-dioxo-18-phenyl-3,4,6,7,8,9-hexahydro-2H,11H-14,16-etheno-2,5-methanopyrido[4,3-k][1,10,3,6]dioxadiazacycloheptadecine-4-carboxylate

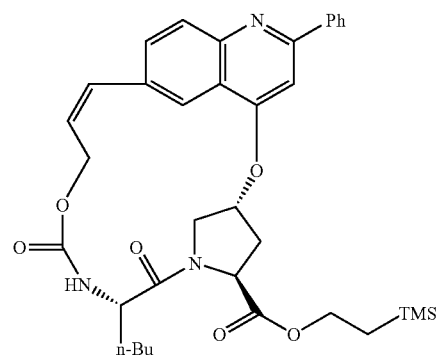

To a degassed (bubble Ar 15 min) solution of 2-(trimethylsilyl)ethyl N-[(allyloxy)carbonyl]-L-norleucyl-(4R)-4-[(2-phenyl-6-vinylquinolin-4-yl)oxy]-L-prolinate 6 (15 mg, 0.023 mmol) in DCM (5 mL) was added the Zhan ruthenium metathesis catalyst RC-301 (Zhan Catalyst I, RC-301, Zannan Pharma Ltd.) (2 mg, 0.002 mmol). The reaction was then sealed and submitted to microwave irradiation (100° C. for 10 min). LC-MS and TLC analysis at this time indicated that nearly complete consumption of the starting material had occurred and the formation of nearly a single product which had the desired mass. The solvent was then removed under nitrogen and the crude product was purified on silica (10-50% EtOAc/hex) to yield the expected product 2-(trimethylsilyl)ethyl (2R,4S,7S)-7-butyl-6,9-dioxo-18-phenyl-3,4,6,7,8,9-hexahydro-2H,11H-14,16-etheno-2,5-methanopyrido[4,3-k][1,10,3,6]dioxadiazacycloheptadecine-4-carboxylate (7) as a single compound as a single compound. $^1$H NMR (500 MHz, CDCl$_3$) ppm: 8.08 (m, 3H), 7.91 (s, 1H), 7.55-7.46 (m, 4H), 7.04 (s, 1H), 6.88 (d, J=11.5 Hz, 1H), 6.05 (m, 1H), 5.30 (d, J=10.5 Hz, 1H), 5.22 (m, 2H), 5.13 (d, J=12 Hz, 1H), 4.70 (m, 2H), 4.32 (dd, J=10.5 Hz, 7 Hz, 1H), 4.23 (m, 2H), 3.92 (dd, J=12 Hz, 3.5 Hz, 1H), 2.88 (m, 1H), 2.40 (m, 1H), 1.92 (m, 1H), 1.76 (m, 1H), 1.40 (m, 4H), 1.00 (m, 2H), 0.93 (br t, J=7 Hz, 3H), 0.04 (s, 9H). LRMS (CI, [M+H]) Calc'd=630.3. found=630.3. HRMS (APCI, [M+H]$^+$) Calc'd for C$_{35}$H$_{44}$N$_3$O$_6$Si: 630.2994. found: 630.2965.

Step 8: (1R,2S)-1-({[(2R,4S,7S)-7-Butyl-6,9-dioxo-18-phenyl-3,4,6,7,8,9-hexahydro-2H,11H-14,16-etheno-2,5-methanopyrido[4,3-k][1,10,3,6]dioxadiazacycloheptadecin-4-yl]carbonyl}amino)-2-vinylcyclopropanecarboxylic acid (III-1)

To a solution of 2-(trimethylsilyl)ethyl (2R,4S,7S)-7-butyl-6,9-dioxo-18-phenyl-3,4,6,7,8,9-hexahydro-2H,11H-14,16-etheno-2,5-methanopyrido[4,3-k][1,10,3,6]dioxadiazacycloheptadecine-4-carboxylate (16 mg, 0.025 mmol) in THF (2 mL) was added a 1M solution of TBAF (0.127 mL, 0.127 mmol). After 30 min, complete consumption of the —OTMSE ester starting material was observed. The solvent was then removed in vacuo, and the crude product was taken up in DMF (2 mL). To this solution was added ethyl (1R,2S)-1-amino-2-vinylcyclopropanecarboxylate (Llinas-Brunet et al., U.S. Pat. No. 6,323,180) (10 mg, 0.051 mmol), diisopropylethylamine (0.051 mL, 0.286 mmol), and TBTU (16 mg, 0.051 mmol). After 30 min at RT, complete consumption of the carboxylic acid partner was observed and the reaction was worked-up with 1N HCl and EtOAc. The organic layer was extracted with saturated aqueous NaHCO$_3$ and brine. The organic layer was then dried over MgSO$_4$ and the solvent was removed in vacuo. The crude product was taken up in a mixture of THF (2 mL), MeOH (1 mL), and water (0.67 mL). To this was added a 1N solution of LiOH (0.33 mL, 0.33 mmol). After 15 h at RT, brine and EtOAc were added to the reaction flask and the pH was adjusted to ~3 with 1 N HCl. Following extraction, the organic layer was washed with saturated aqueous NaHCO$_3$ and dried over MgSO$_4$. The solvent was removed in vacuo and the crude product was purified on a Gilson reverse phase chromatography system (95/5 water/acetonitrile with 0.15% TFA to 5/95) to yield 7 mg (43% yield) of the expected product (1R,2S)-1-({[(2R,4S,7S)-7-butyl-6,9-dioxo-18-phenyl-3,4,6,7,8,9-hexahydro-2H,11H-14,16-etheno-2,5-methanopyrido[4,3-k][1,10,3,6]dioxadiazacycloheptadecin-4-yl]carbonyl}amino)-2-vinylcyclopropanecarboxylic acid (III-1). $^1$H NMR (400 MHz, MeOH-d$_4$) ppm: 8.64, 8.55, 8.52 (3 s, 1H), 8.22 and 8.20 (2s, 2H), 8.09 (m, 2H), 8.00 (app dd, J=9 Hz, 2 Hz, 1H), 7.74 (m, 3H), 7.01 (d, J=11.2 Hz, 1H), 6.35-6.25 (m, 1H), 5.87-5.77 (m, 2H), 5.31-5.08 (m, 4H), 4.56 (m, 2H), 4.31 (m, 2H), 4.31 (m, 1H), 4.05 (d, J=12.5 Hz, 1H), 3.24 (m, 1H), 2.84 (m, 1H), 2.70 (m, 1H), 2.20 (app q, J=8.8. Hz, 1H), 1.85-1.64 (m, 4H), 1.44 (m, 5H), 1.04-0.95 (m, 3H). LRMS (CI, [M+H]) Calc'd=639.4. found=639.4. HRMS (APCI, [M+H]$^+$) Calc'd for C$_{36}$H$_{39}$N$_4$O$_7$: 639.2813. found: 639.2849.

EXAMPLE 2

(1R,2S)-1-({[(2R,4S,7S)-7-Butyl-6,9-dioxo-18-phenyl-3,4,6,7,8,9,12,13-octahydro-2H,11H-14,16-etheno-2,5-methanopyrido[4,3-k][1,10,3,6]dioxadiazacycloheptadecin-4-yl]carbonyl}amino)-2-vinylcyclopropanecarboxylic acid (III-2)

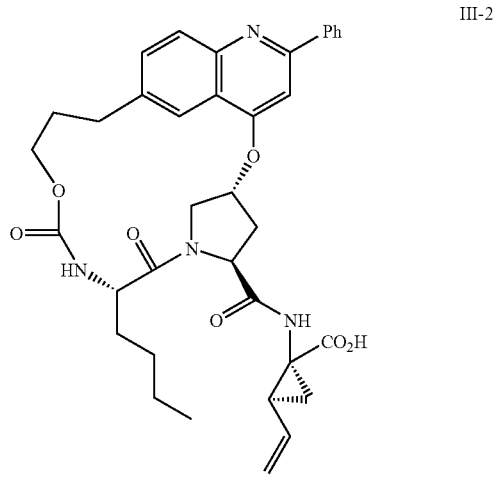

To a solution of 2-(trimethylsilyl)ethyl (2R,4S,7S)-7-butyl-6,9-dioxo-18-phenyl-3,4,6,7,8,9-hexahydro-2H,1H-14,16-etheno-2,5-methanopyrido[4,3-k][1,10,3,6]dioxadiazacycloheptadecine-4-carboxylate (Example 1 Step 7) (6 mg, 0.01 mmol) in EtOAc (1 mL) was added 10% Pd/C (1 mg, 0.001 mmol Pd). The flask was quickly evacuated and hydrogen gas was then introduced. This cycle was repeated three times and a balloon of H$_2$ was left over the reaction. After 5 h, only a trace amount of unreduced starting material remained, and after 15 h, complete consumption of the starting material had occurred. The crude product was then filtered through celite with EtOAc as the eluent. The solvent was removed in vacuo and the crude material was used directly in the next reaction. To a solution of this crude product (6 mg, 0.009 mmol) in THF (1 mL) was added a 1M solution of TBAF (0.047 mL, 0.047 mmol). After 30 min, complete consumption of the —OTMSE ester starting material was observed. The solvent was then removed in vacuo, and the crude product was taken up in DMF (1 mL). To this solution was added ethyl (+/−)-1-amino-2-vinylcyclopropanecarboxylate (4 mg, 0.019 mmol), diisopropylethylamine (0.017 mL, 0.095 mmol), and TBTU (6 mg, 0.019 mmol). After 1 h at RT, complete consumption of the carboxylic acid partner was observed and the reaction was worked-up with 1N HCl and EtOAc. The organic layer was extracted with saturated aqueous NaHCO$_3$ and brine. The organic layer was then dried over MgSO$_4$ and the solvent was removed in vacuo. The crude product was taken up in a mixture of THF (0.6 mL), MeOH (0.3 mL), and water (0.2 mL). To this was added a 1N solution of LiOH (0.1 mL, 0.1 mmol). After 18 h at RT, brine and EtOAc were added to the reaction flask and the pH was adjusted to ~3 with 1 N HCl. Following extraction, the organic layer was washed with saturated aqueous NaHCO$_3$ and dried over MgSO$_4$. The solvent was removed in vacuo and the crude product was purified on a Gilson reverse phase chromatography system (95/5 water/acetonitrile with 0.15% TFA to 5/95) to yield 2.3 mg (38% yield) of (1R,2S)-1-({[(2R,4S,7S)-7-butyl-6,9-dioxo-18-phenyl-3,4,6,7,8,9,12,13-octahydro-2H,1H-14,16-etheno-2,5-methanopyrido[4,3-k][1,10,3,6]dioxadiazacycloheptadecin-4-yl]carbonyl}amino)-2-vinylcyclopropanecarboxylic acid (III-2). $^1$H NMR (500 MHz, MeOH-d$_4$) ppm: mixture of diastereomers due to racemic ethyl (+/−)-1-amino-2-vinylcyclopropanecarboxylate: 8.81 and 8.67 (2 s, 1H), 8.15 (d, J=8.5 Hz, 1H), 8.08 (m, 2H), 7.98 (m, 1H), 7.87 (m, 1H), 7.75 (m, 3H), 5.80 (m, 2H), 5.32 and 5.28 (2 m, 1H), 5.09 (m, 2H), 4.63 (m, 2H), 4.06-3.94 (m, 2H), 3.78 (m, 1H), 3.10 (m, 1H), 2.98 and 2.95 (2 t, J=3.5 Hz, 1H), 2.83 (m, 1H), 2.62 (m, 1H), 2.30 (m, 1H), 2.20 (app pent, J=8.5 Hz, 1H), 1.86 (m, 1H), 1.81-1.71 (m, 2H), 1.49-1.30 (m, 5H), 0.97 (m, 3H). LRMS (CI, [M+H]) Calc'd=641.4. found=641.4. HRMS (APCI, [M+H]$^+$) Calc'd for C$_{36}$H$_{41}$N$_4$O$_7$: 641.2970. found: 641.3000.

EXAMPLE 3

(1R,2S)-1-({[(2R,4S,7S)-7-Butyl-6,9-dioxo-20-phenyl-3,4,6,7,8,9,12,13-octahydro-2H,11H-16,18-ethanediylidene-2,5-methanopyrido[4,3-k][1,10,3,6]dioxadiazacyclononadecin-4-yl]carbonyl}amino)-2-vinylcyclopropanecarboxylic acid (III-3)

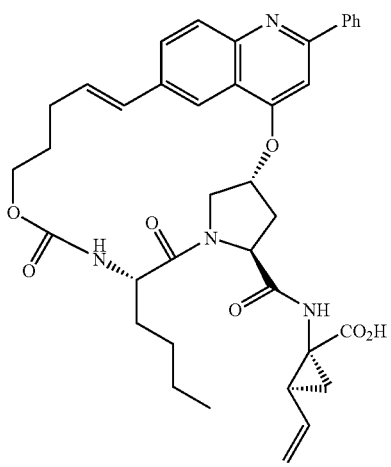

III-3

The title compound was prepared in a manner similar to Example 1 (Steps 1-8). [(4-Pentenyloxy)carbonyl]-L-norleucine (preparation described below) was used in place of N-[(allyloxy)carbonyl]-L-norleucine. $^1$H NMR (500 MHz, MeOH-$d_4$) ppm: 8.70 (s, 1H), 8.11 (m, 3H), 7.96 (m, 1H), 7.74 (m, 4H), 6.71 (d, J=15.9 Hz, 1H), 6.59 (m, 1H), 5.83 (m, 2H), 5.27 (d, 1H), 5.10 (d, 1H), 4.83 (m, 2H), 4.48 (m, 3H), 4.16 (d, 1H), 4.00 (m, 1H), 2.80 (m, 1H), 2.56 (m, 1H), 2.18 (m, 2H), 1.91 (dd, 1H), 1.90-1.63 (m, 6H), 1.50-1.40 (m, 5H), 0.95 (t, 3H). LRMS (CI, [M+H]) Calc'd=667.4. found=667.4. HRMS (APCI, [M+H]$^+$) Calc'd for $C_{38}H_{43}N4O_7$: 667.3126. found: 667.3119.

[(4-Pentenyloxy)carbonyl]-L-norleucine

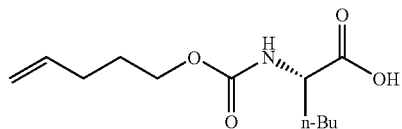

11

To a solution of 1-penten-4-ol (0.95 g, 11.0 mmol) in DMF (15 mL) at 0° C. was added carbonyldiimidazole (1.79 g, 11.0 mmol). The reaction mixture was warmed to RT and stirred for 30 min. L-norleucine methyl ester hydrochloride (2.0 g, 1.0 mmol) was then added, the reaction mixture was heated to 50° C. and stirred for 15 min. Upon cooling, the reaction mixture was diluted with ethyl ether and washed twice with water. The organic layer was dried over NaSO$_4$, filtered and concentrated. The crude product was purified by silica gel chromatography (gradient elution 10 to 90% ethyl acetate in hexanes) to afford [(4-pentenyloxy)carbonyl]-L-norleucine methyl ester (2.1 g, 74% yield) as a clear oil. $^1$H NMR (500 MHz, CDCl$_3$) ppm: δ 5.81 (m, 1H), 5.14 (d, J=7.6 Hz, 1H), 5.06-4.97 (m, 2H), 4.35 (q, J=5.4 Hz, 1H), 4.08 (t, J=6.6 Hz, 2H), 3.75 (s, 3H), 2.12 (q, J=7.1 Hz, 2H), 1.82 (brs, 1H), 1.72 (quin, J=7.1 Hz, 2H), 1.65 (br s, 1H), 1.32 (m, 4H), 0.90 (t, J=7.1 Hz, 3H).

To a solution of [(4-pentenyloxy)carbonyl]-L-norleucine methyl ester (1.8 g, 7.0 mmol) in THF (5 mL) at RT was added 1M sodium hydroxide solution (5 mL). The reaction mixture was stirred at RT for 3 h. The reaction mixture was then worked up with EtOAc and 1M HCl. The organic layer was separated and washed with H$_2$O, brine, dried over Na$_2$SO$_4$, filtered and concentrated to give [(4-pentenyloxy)carbonyl]-L-norleucine (1.4 g, 82% yield). $^1$H NMR (500 MHz, CD$_3$OD) ppm: δ 5.82 (m, 1H), 5.05 (d, 1H), 4.98 (d, 1H), 4.86 (brs, 2H), 4.10 (m, 1H), 4.08 (t, 2H), 2.16 (q, 2H), 1.82 (m, 1H), 1.72 (m, 3H), 1.38 (m, 4H), 0.93 (t, 3H).

EXAMPLE 4

(1R,2S)-1-({[(2R,4S,7S)-7-Butyl-6,9-dioxo-19-phenyl-3,4,6,7,8,9,11,12-octahydro-2H-15,17-ethanediylidene-2,5-methanopyrido[4,3-k][1,10,3,6]dioxadiazacyclooctadecin-4-yl]carbonyl}amino)-2-vinylcyclopropanecarboxylic acid (III-4)

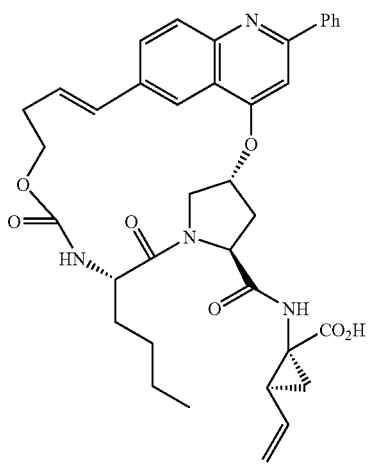

III-4

The title compound was prepared in a manner similar to Example 1 (Steps 1-8). N-[(but-3-en-1-yloxy)carbonyl]-L-norleucine was prepared according to the procedure used for [(4-pentenyloxy)carbonyl]-L-norleucine (Example 3), and was used in place of N-[(allyloxy)carbonyl]-L-norleucine. $^1$H NMR (500 MHz, MeOH-$d_4$) ppm: 8.58 (s, 1H), 8.42 (s, 1H), 8.09 (m, 3H), 7.96 (d, 1H), 7.74 (m, 4H), 6.70 (d, J=15.2 Hz, 1H), 6.39 (m, 1H), 5.87 (m, 2H), 5.29 (d, 1H), 5.10 (d, 1H), 4.80 (m, 2H), 4.71 (m, 2H), 4.57 (t, 1H), 4.07 (m, 2H), 2.86 (dd, 1H), 2.70 (m, 1H), 2.55 (m, 1H), 2.48 (t, 1H), 2.17 (dd, 1H), 1.85 (m, 1H), 1.79-1.64 (m, 2H), 1.55-1.37 (m, 5H), 1.01 (t, 3H). LRMS (CI, [M+H]) Calc'd=653.4. found=653.4.

EXAMPLE 5

(1R,2S)-1-({[(2R,4S,7S)-7-Butyl-6,9-dioxo-19-phenyl-3,4,6,7,8,9,11,12,13,14-decahydro-2H-15,17-ethanediylidene-2,5-methanopyrido[4,3-k][1,10,3,6]dioxadiazacyclooctadecin-4-yl]carbonyl}amino)-2-vinylcyclopropanecarboxylic acid (III-5)

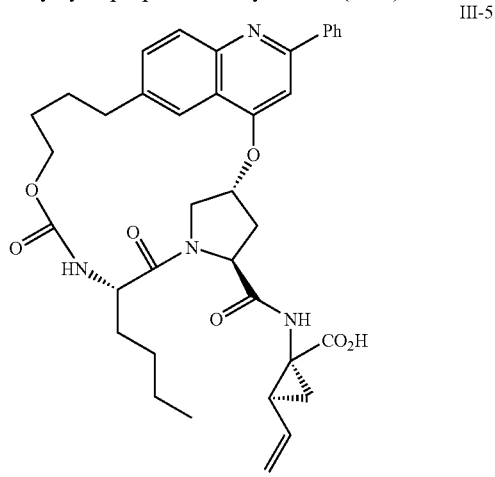

The title compound was prepared in a manner similar to Example 1 (Steps 1-7) and Example 2. N-[(But-3-en-1-yloxy)carbonyl]-L-norleucine was prepared according to the procedure used for [(4-pentenyloxy)carbonyl]-L-norleucine, and was used in place of N-[(allyloxy)carbonyl]-L-norleucine. $^1$H NMR (500 MHz, MeOH-$d_4$) ppm: 8.59 (s, 1H), 8.34 (s, 1H), 8.10 (m, 3H), 7.96 (d, 1H), 7.77 (m, 4H), 5.82 (m, 2H), 5.30 (d, 1H), 5.10 (d, 1H), 4.82 (m, 2H), 4.64 (m, 2H), 4.59 (t, 1H), 4.10 (m, 2H), 3.80 (m, 1H), 3.08 (m, 1H), 2.88 (m, 2H), 2.60 (m, 1H), 2.19 (dd, 1H), 1.90-1.63 (m, 6H), 1.50-1.40 (m, 5H), 0.95 (t, 3H). LRMS (CI, [M+H]) Calc'd=655.4. found=655.4.

EXAMPLE 6

(1R,2S)-1-({[(2R,4S,7S)-7-Butyl-6,9-dioxo-18-phenyl-3,4,6,7,8,9,10,11-octahydro-2H-14,16-ethanediylidene-2,5-methanopyrido[3,4-p][1,5,8]oxadiazacycloheptadecin-4-yl]carbonyl}amino)-2-vinylcyclopropanecarboxylic acid (III-6)

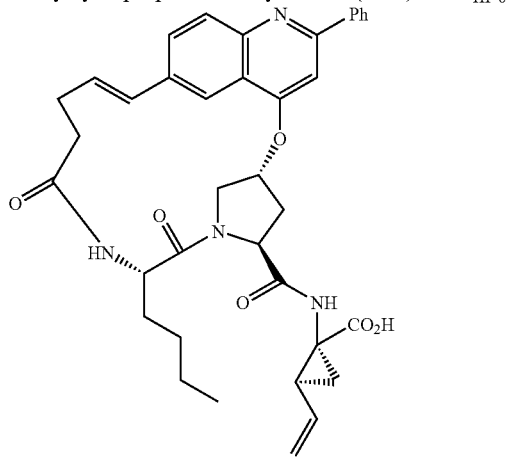

The title compound was prepared in a manner similar to Example 1 (Steps 1-8). N-Pent-4-enoyl-L-norleucine was prepared as described below, and was used in place of N-[(allyloxy)carbonyl]-L-norleucine. $^1$H NMR (500 MHz, MeOH-$d_4$) ppm: 9.10 (s, 1H), 8.21 (s, 1H), 8.10 (m, 3H), 7.96 (m, 1H), 7.84 (m, 4H), 6.76 (d, J=15.6 Hz, 1H), 6.35 (m, 1H), 6.08 (s, 1H), 5.83 (m, 2H), 5.35 (d, 1H), 5.12 (d, 1H), 5.01 (t, 1H), 4.80 (d, 2H), 4.50 (d, 1H), 3.65 (d, 1H), 2.85 (m, 1H), 2.74 (m, 1H), 2.50 (m, 3H), 2.10 (dd, 1H), 1.80-1.63 (m, 3H), 1.50-1.40 (m, 5H), 0.94 (t, 3H). LRMS (CI, [M+H]) Calc'd=637.4. found=637.4. HRMS (APCI, [M+H]$^+$) Calc'd for $C_{37}H_{41}N_4O_6$: 637.3021. found: 637.3019.

N-Pent-4-enoyl-L-norleucine

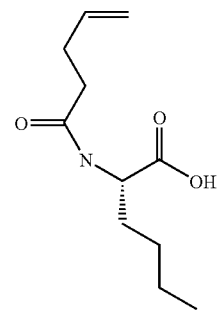

To a solution of L-norleucine methyl ester hydrochloride (0.50 g, 2.75 mmol) and 4-pentenoic acid (0.33 g, 3.30 mmol) in DMF (5 mL) was added EDC (0.79 g, 4.13 mmol) and HOBt (0.56 g, 4.13 mmol). The reaction mixture was stirred at 50° C. for 15 h, cooled and poured onto a mixture of ethyl ether and water. The organic layer was washed with water, dried over NaSO$_4$, filtered and concentrated. The crude product was purified by silica gel chromatography (gradient elution 10% to 90% ethyl acetate in hexanes) to give N-pent-4-enoyl-L-norleucine methyl ester.

N-Pent-4-enoyl-L-norleucine methyl ester (0.30 g, 1.32 mmol) was dissolved in THF (3 mL) and 1 M NaOH (3 mL) was added at RT. The reaction mixture was stirred for 3 h, poured onto ethyl acetate and 1 M HCl and the layers were separated. The organic layer was washed with water, dried over NaSO$_4$, filtered and concentrated to give N-pent-4-enoyl-L-norleucine (0.25 g, 89% yield): $^1$H NMR (400 MHz, CD$_3$OD) δ ppm 5.81 (m, 1H), 5.02 (d, 1H), 4.95 (d, 1H), 4.82 (br s, 1H), 4.27 (m, 1H), 2.32 (br s, 4H), 1.80 (m, 1H), 1.65 (m, 1H), 1.37 (m, 4H), 0.9 (t, 3H).

EXAMPLE 7

(1R,2S)-1-({[(6R,8S,11S,14aS,17aR)-11-Butyl-10,13-dioxo-3-phenyl-7,8,10,11,12,13,15,16,17,17a-decahydro-6H,14aH-1,20-etheno-6,9-methanocyclopenta[q]pyrido[4,3-k][1,10,3,6]dioxadiazacyclooctadecin-8-yl]carbonyl}amino)-2-vinylcyclopropanecarboxylic acid (III-7)

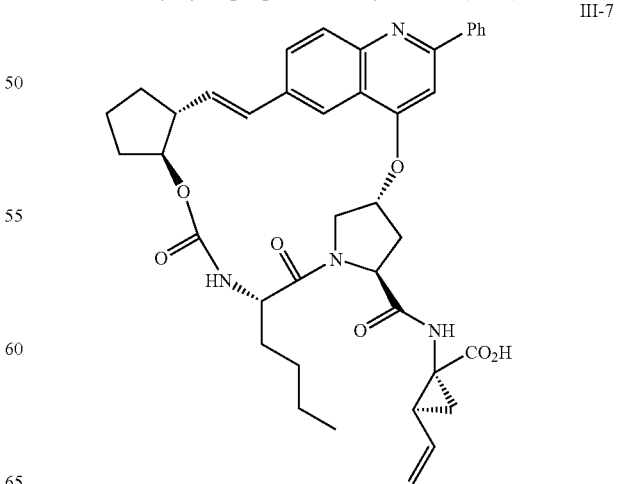

The title compound was prepared in a manner similar to Example 1 (Steps 1-8). (+/−)-N-({[2-Vinylcyclopentyl]

oxy}carbonyl)-L-norleucine was prepared as indicated below, and was used in place of N-[(allyloxy)carbonyl]-L-norleucine. ¹H NMR (500 MHz, MeOH-d₄) ppm: mixture of 2 diastereomers (at vinylcyclopentanol stereocenters): 8.54 (br s, 2H), 8.07 (m, 3H), 7.94 (m, 1H), 7.75 (m, 4H), 6.71 (dd, J=16 z, 4.5 Hz, 1H), 6.60 (d, J=16 Hz, 1H), 5.82 (m, 2H), 5.24 (2d, J=17 Hz, 1H), 5.09 (2d, J=10.5 Hz, 1H), 4.76 (m, 2H), 4.68 (m, 1H), 4.50 (m, 1H), 4.09 (2d, J=12 Hz, 1H), 2.82 (m, 1H), 2.68 (m, 1H), 2.50 (m, 1H), 2.14 (m, 2H), 1.97-1.65 (m, 8H), 1.73 (m, 1H), 1.66 (m, 1H), 1.52-1.37 (m, 5H), 0.99 (t, J=3H). LRMS (CI, [M+H]) Calc'd=693.3. found=693.3. HRMS (APCI, [M+H]⁺) Calc'd for $C_{40}H_{44}N_4O_7$: 693.3283. found: 693.3247.

N-({[2-Vinylcyclopentyl]oxy}carbonyl)-L-norleucine

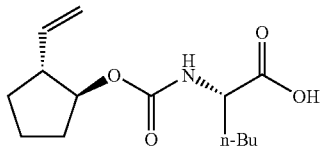

16

To a dark colored solution of $CuBr(Me_2S)$ (122 mg, 0.59 mmol) in THF (10 mL) cooled to −40° C. was added cyclopenteneoxide (0.52 mL, 5.94 mmol). VinylMgBr (11.9 mmol of a 1 M solution in THF, 11.9 mmol) was then added dropwise over 20 min. The mixture was then slowly warmed to −20° C. and then to 0° C. and stirred at this temperature for 2 h. Sat. aq. $NH_4Cl$ was then added along with EtOAc to quench the reaction. The organic layer was dried over $MgSO_4$ and the solvent was removed in vacuo to give 550 mg (82%) of crude product which appeared to be nearly exclusively the trans isomer. The crude product was used as is in further reactions.

To a solution of diphosgene (1.16 g, 5.88 mmol) in THF (10 mL) cooled to 0° C. was added a solution of trans-2-vinylcyclopentanol (550 mg, 4.9 mol) and $Et_3N$ (0.72 mL, 5.15 mmol). After 1 h, TLC revealed the consumption of the vinylcyclopentanol. THF and excess diphosgene were removed in vacuo to a volume of ~10 mL. In a separate flask was added ½ of the NaOH solution and nle (0.71 g, 5.4 mmol). To this was added the THF solution of chloroformate and the remainder of the NaOH solution. After 30 min, TLC revealed the consumption of the chloroformate. The mixture was acidified with 4 N HCl (1.3 mL) to ~pH 3. The mixture was then extracted with EtOAc. The organic layer was dried over $MgSO_4$ and the solvent was removed in vacuo. The crude product was then purified on silica (10-80% EtOAc/hexanes with 2% HOAc) and then on a Gilson reverse phase system to give 300 mg (23%) of the expected product. ¹H NMR (400 MHz, MeOH-d₄) ppm: 5.81 (m, 1H), 5.07 (d, =15.6 Hz, 1H), 4.99 (d, J=10.4 Hz, 1H), 4.75 (m, 1H), 4.08 (m, 2H), 2.58 (m, 1H), 1.93 (m, 2H), 1.82-1.61 (m, 5H), 1.51 (m, 1H), 1.36 (m, 4H), 0.92 (t, J=7.2 Hz, 3H). LRMS (CI, [M+H]) Calc'd=270.3. found=270.3.

EXAMPLE 8

(1R,2S)-1-({[(2R,4S,7S)-7-Butyl-23-methoxy-6,9-dioxo-20-phenyl-3,4,6,7,8,9,12,13-octahydro-2H,11H-16,18-etheno-2,5-methanopyrido[4,3-k][1,10,3,6]dioxadiazacyclononadecin-4-yl]carbonyl}amino)-2-vinylcyclopropanecarboxylic acid (III-8)

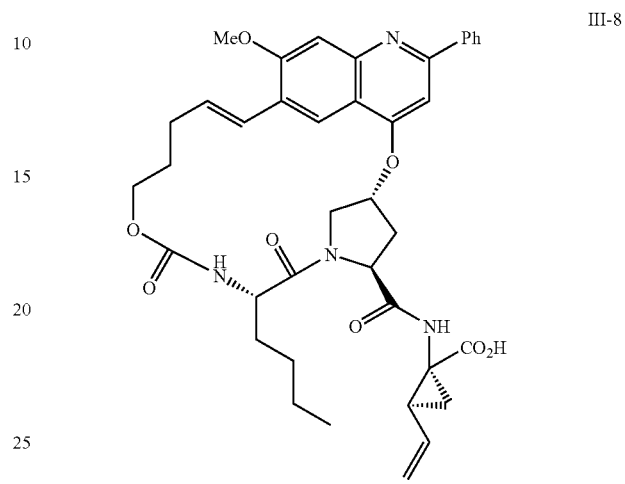

The title compound was prepared in a manner similar to Example 1 (Steps 1-8). [(4-Pentenyloxy)carbonyl]-L-norleucine (Example 3) was used in place of N-[(allyloxy)carbonyl]-L-norleucine. 7-Methoxy-2-phenyl-6-vinylquinolin-4(1H)-one (preparation described below) was used in place of 2-phenyl-6-vinylquinolin-4(1H)-one. ¹H NMR (500 MHz, MeOH-d₄) ppm: 8.62 (s, 1H), 8.58 (s, 1H), 8.05 (m, 2H), 7.74 (m, 3H), 7.61 (s, 1H), 7.48 (s, 1H), 6.77 (d, J=16 Hz, 1H), 6.41 (dt, J=16 Hz, 7 Hz, 1H), 5.82 (m, 2H), 5.25 (d, J=17 Hz, 1H), 5.08 (d, J=12 Hz, 1H), 4.89 (m, 1H), 4.48 (m, 1H), 4.39 (m, 1H), 4.32 (m, 1H), 4.10 (m, 1H), 4.04 (s, 3H), 4.00 (m 1H), 3.23 (m, 1H), 2.78 (dd, J=14 Hz, 7.5 Hz, 1H), 2.33 (m, 1H), 2.30 (m, 2H), 2.16 (q, J=9 Hz, 1H), 1.84 (m, 3H), 1.69 (m, 3H), 1.50 (m, 2H), 1.43 (m, 3H), 1.01 (m, 3H). LRMS (CI, [M+H]) Calc'd=697.3. found=697.4.

Step 1: Ethyl (2Z)-3-(methylamino)-3-phenylacrylate

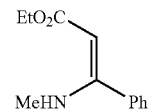

18

To a solution of methylamine (65.03 mL of a 2M solution in THF, 130.06 mmol) and ethyl benzoylacetate (4.505 mL, 26.01 mmol) in EtOH (26 mL) was added HOAc (7.45 mL, 130.06 mmol). The mixture was then heated to reflux for 15 h. At this time, crude 1H NMR revealed only product and $MeNH_2$—HOAc. The reaction mixture was then cooled to RT, and the solvent was removed in vacuo. The crude reaction was then extracted with 1 N HCl and DCM. The organic layer was then dried over $MgSO_4$, and the solvent was removed in vacuo to yield 5.3 g (99%) of ethyl (2Z)-3-(methylamino)-3-phenylacrylate. The product was used as is in subsequent reactions. ¹H NMR (500 MHz, $CDCl_3$) ppm: 8.50 (br s, 1H), 7.40 (m, 3H), 7.35 (m, 2H), 4.59 (s, 1H), 4.15 (q, J=7.0 Hz, 2H), 2.77 (d, J=5.0 Hz, 3H), 2.50 (s, 3H), 1.27 (t, J=7.0 Hz, 3H).

Step 2: Ethyl (2Z)-3-[(4-bromo-3-methoxyphenyl)amino]-3-phenylacrylate

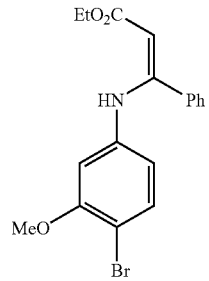

19

To a solution of ethyl (2Z)-3-(methylamino)-3-phenylacrylate (4.47 g, 21.77 mmol) in DCM (100 mL) was added 4-bromo-3-methoxyaniline (4 g, 19.80 mmol) and PPTS (5.47 g, 21.77 mmol). The mixture was then heated to reflux for 24 h. At this time crude 1H NMR revealed nearly complete consumption of the aniline. The reaction was then cooled to RT, filtered, and the solvent was removed in vacuo. The crude product was purified on silica (75% DCM/hexanes) to yield ethyl (2Z)-3-[(4-bromo-3-methoxyphenyl)amino]-3-phenylacrylate (6.5 g, 87%) which was used as is in subsequent reactions. $^1$H NMR (500 MHz, CDCl$_3$) ppm: 10.32 (br s, 1H), 7.32 (m, 5H), 7.20 (d, J=8.5 Hz, 1H), 6.19 (dd, J=8.5 Hz, 2.5 Hz, 1H), 6.11 (d, J=2.5 z, 1H), 5.03 (s, 1H), 4.21 (q, J=7.0 Hz, 2H), 3.50 (s, 3H), 1.32 (t, J=7.0 Hz, 3H).

Step 3: 6-Bromo-7-methoxy-2-phenylquinolin-4(1H)-one

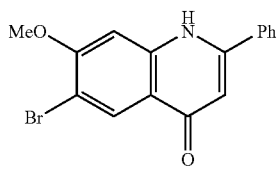

20

To refluxing (~300° C.) dowtherm A (100 ml) (mixture of biphenyl and diphenyl ether) was added ethyl (2Z)-3-[(4-bromo-3-methoxyphenyl)amino]-3-phenylacrylate (6.5 g, 17.27 mmol) in DOWTHERM A (5 mL, washed with 1 mL). Almost immediately, white solid begins to precipitate out of solution. Refluxing was continued for 40 min, and the reaction was cooled to RT and let stand for 1 h. The white solid was then filtered off, and the washed extensively with hexanes to give 6-bromo-7-methoxy-2-phenylquinolin-4(1H)-one as white crystals (4.72 g, 83%). $^1$H NMR (400 MHz, DMSO-d$_6$): 11.69 (s, 1H), 8.19 (s, 1H), 7.82 (m, 2H), 7.59 (m, 3H), 7.35 (s, 1H), 6.33 (s, 1H), 3.96 (s, 3H). LRMS (CI, [M+H]) Calc'd=330.0. found=330.1.

Step 4: 7-Methoxy-2-phenyl-6-vinylquinolin-4(1H)-one

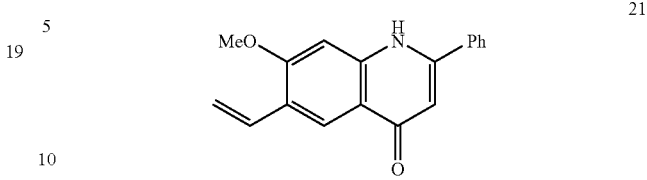

21

To a solution of 6-bromo-7-methoxy-2-phenylquinolin-4(1H)-one (1.0 g, 3.03 mmol) in DMSO (35 mL) was added tri(n-butyl)vinyltin (1.06 mL, 3.63 mmol) and finally tetrakis(triphenylphosphine)palladium (88 mg, 0.076 mmol). The mixture was then degassed using a freeze/pump/thaw cycle (2×). The mixture was then heated to 100° C. in a sealed tube for 22 h. At this time, LC-MS revealed complete consumption of the bromoquinoline). The reaction mixture was then poured into a mixture of water (200 mL) and EtOAc (200 mL) which caused solid to crash out. The solid was filtered off, washed with CH$_3$CN, EtOAc, DCM, and then hexanes to give 7-methoxy-2-phenyl-6-vinylquinolin-4(1H)-one as a light greenish solid (670 mg, 80%). $^1$H NMR (400 MHz, DMSO-d$_6$) ppm: 11.58 (s, 1H), 8.16 (s, 1H), 7.83 (m, 2H), 7.58 (m, 3H), 7.25 (s, 1H), 6.99 (dd, J=11 Hz, 17.5 Hz, 1H), 6.28 (s, 1H), 5.85 (d, J=17.5 Hz, 1H), 5.31 (d, J=11 Hz, 1H), 3.92 (s, 3H). LRMS (CI, [M+H]) Calc'd=278.1. found=278.2.

EXAMPLE 9

HCV NS3 Protease Time-Resolved Fluorescence (TRF) Assay

The NS3 protease TRF assay was performed in a final volume of 100 µl in assay buffer containing 50 mM HEPES, pH 7.5, 150 mM NaCl, 15% glycerol, 0.15% TRITON X-100, 10 mM DTT, and 0.1% PEG 8000. The NS3 protease was pre-incubated with various concentrations of inhibitors for 10-30 minutes. The peptide substrate for the assay is Ac—C(Eu)-DDMEE-Abu-[COO]-XSAK(QSY7)-NH2, where Eu is an europium-labeled group, Abu is 1-aminobutanoic acid which connects an ester linkage with 2-hydroxy propanoic acid (X). Hydrolysis of the peptide by NS3 protease activity causes in separation of the fluorophore from the quencher, resulting in an increase in fluorescence. Activity of the protease was initiated by adding the TRF peptide substrate (final concentration 50-100 nM). The reaction was quenched after 1 hour at room temperature with 100 µl of 500 mM MES, pH 5.5. Product fluorescence was detected using either a VICTOR V2 or FUSION fluorimeter (Perkin Elmer Life and Analytical Sciences) with excitation at 340 nm and emission at 615 nm with 50-400 µs delay. Testing concentrations of different enzyme forms was selected with a signal to background ratio of 10-30. The inhibition constants were derived using a four-parameter fit.

Compounds III-1 to III-8 and III-13 to III-65 were tested to have a Ki value of less than 10 µM in the NS3 protease TRF assay as described above.

Synthesis of Intermediates:

2-(Dimethylamino)pent-4-en-1-ol (22)

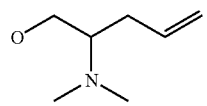

Step 1: Ethyl 2-aminopent-4-enoate

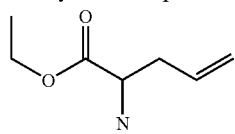

A solution of RS-2-amino-4-pentenoic acid (2.5 g, 21.7 mmol) and conc. HCl (3.6 mL) were dissolved in 50 mL EtOH and refluxed for 18 h. The reaction mixture was poured into sat'd NaHCO₃ and EtOAc, the organic layer was separated, dried over anhydrous NaSO₄ and concentrated to give the amino ester as a colorless oil (0.95 g, 31% yield).

Step 2: Ethyl 2-(dimethylamino)pent-4-enoate

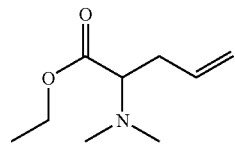

To a solution of the amino ester (250 mg, 1.7 mmol) in 10 mL MeOH was added sodium cyanoborohydride (329 mg, 5.2 mmol) and paraformaldehyde (157 mg, 5.2 mmol). The suspension was stirred at 50° C. for 48 h, then acidified with 6 N HCl and washed with EtOAc. The aqueous layer was basified with sat'd NaHCO₃, and extracted with EtOAc. The organic layer was dried over anhydrous NaSO₄ and concentrated to give the dimethylamino ester as an orange oil (112 mg, 37% yield).

Step 3: 2-(dimethylamino)pent-4-en-1-ol (22)

To an ice-cooled solution of the amino ester in 10 mL THF was added slowly 1 M lithium aluminum hydride in THF (1.75 mL, 1.75 mmol). After 2 hrs, 0.067 mL of water, 0.20 mL 3 N NaOH and 0.20 mL of water were added sequentially. Diethyl ether was added and the suspension was stirred for 10 min, then filtered, dried over anhydrous NaSO₄ and concentrated to give the desired amino alcohol as a colorless oil (125 mg, 83% yield). $^1$H NMR (400 MHz, CDCl₃, ppm) δ 5.70 (m, 1H), 5.01 (dd, 2H), 3.48 (dd, 1H), 3.22 (t, 1H), 2.63 (m, 1H), 2.31 (m, 1H), 2.23 (s, 6H), and 1.8 (m, 1H).

The following carbamate intermediates were prepared using the chemistry described for the preparation of N-(allyloxy)carbonyl-L-norleucine (Example 1 Step 4), by utilizing the appropriate amino acid and alcohol (Int=Intermediate):

| Int | Amino Acid | Alcohol | Structure |
| --- | --- | --- | --- |
| A1 | L-Norleucine | 3-Buten-1-ol | 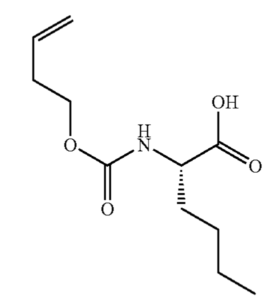 |
| A2 | L-Norleucine | 4-Penten-1-ol | 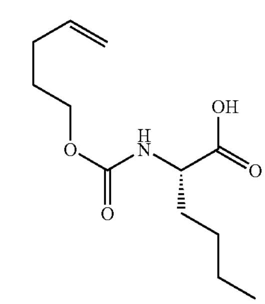 |

-continued
| Int | Amino Acid | Alcohol | Structure |
|---|---|---|---|
| A3 | L-Norleucine | 5-Hexen-1-ol | 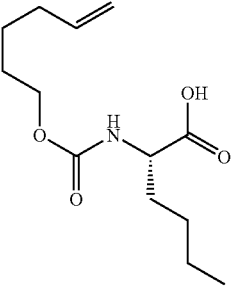 |
| A4 | L-Norleucine | 6-Hepten-1-ol | 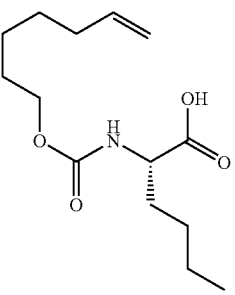 |
| A5 | L-Norleucine | 3,3-Dimethyl-4-penten-1-ol<br>Ref: Srikrishna, A.; Dethe, D. H.; Kumar, P. R. Tet. Lett. (2004), 45(14), pp 2939-2942. | 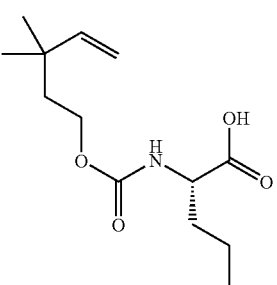 |
| A6 | L-Norleucine | 2,2-Dimethyl-4-penten-1-ol<br>Ref: Hill, E. A.; Link, D. C.; Donndelinger, P. J. Org. Chem. (1981), 46(6), pp 1177-1182. | 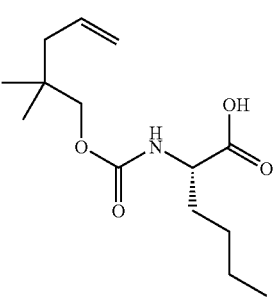 |
| A7 | L-Norleucine | Trans-2-vinyl-cyclopentan-1-ol<br>Ref: Hill, E. A.; Link, D. C.; Donndelinger, P. J. Org. Chem. (1981), 46(6), pp 1177-1182. | 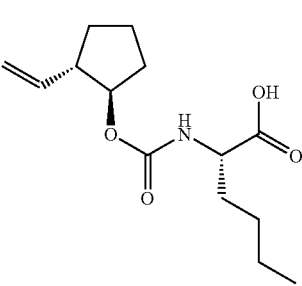 |

-continued

| Int | Amino Acid | Alcohol | Structure |
|---|---|---|---|
| A8 | L-Valine | 3-Buten-1-ol | 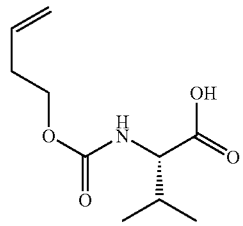 |
| A9 | L-Valine | 4-Penten-1-ol | 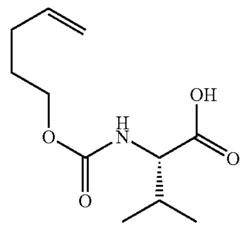 |
| A10 | L-t-Butylglycine | 4-Penten-1-ol | 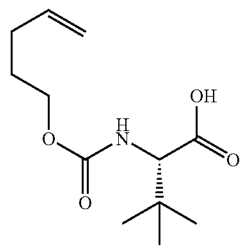 |
| A11 | L-N-Δ-Boc Ornithine | 4-Penten-1-ol | 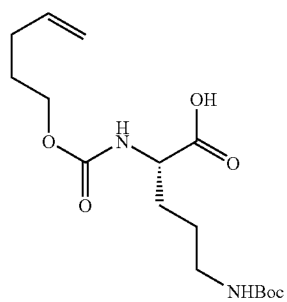 |
| A12 | L-Alanine | 4-Penten-1-ol | 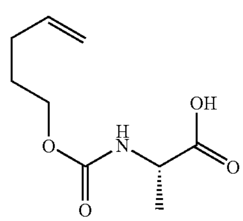 |
| A13 | L-cyclohexyl-glycine | 2,2-Dimethyl-4-penten-1-ol Ref: Hill, E. A.; Link, D. C.; Donndelinger, P. J. Org. Chem. (1981), 46(6), pp 1177-1182. | 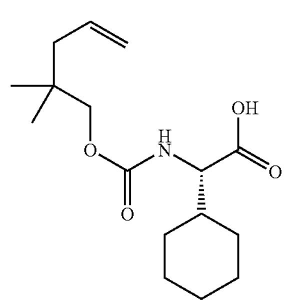 |

-continued

| Int | Amino Acid | Alcohol | Structure |
|---|---|---|---|
| A14 | L-norleucine | 2-(dimethylamino)pent-4-en-1-ol (Intermediate A1) | 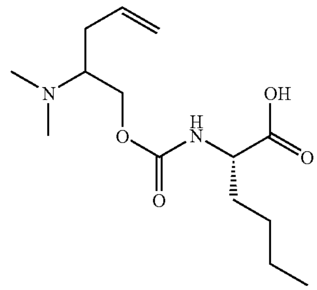 |
| A15 | L-(N-Boc-4-piperidinyl)-glycine | 4-Penten-1-ol | 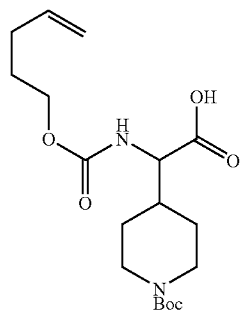 |

The following amide intermediates were prepared using the chemistry described for the preparation of N-pent-4-enoyl-L-norleucine (as described in Example 6), by utilizing the appropriate amino acid and unsaturated carboxylic acid:

| Int | Amino Acid | Unsaturated Carboxylic acid | Structure |
|---|---|---|---|
| A16 | L-Norleucine | 5-Hexenoic acid | 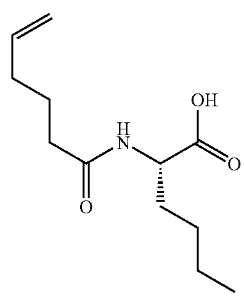 |
| A17 | L-Norleucine | 6-Heptenoic acid | 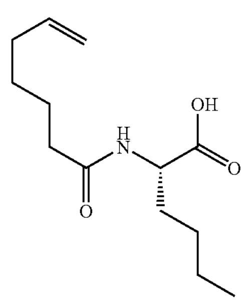 |

A18: (2S)-3-Methyl-2-({[methyl(pent-4-en-1-yl)amino]carbonyl}amino)butanoic acid

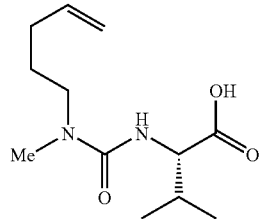

A18

Step 1: Methyl (2S)-3-methyl-2-({[methyl(pent-4-en-1-yl)amino]carbonyl}amino)butanoate

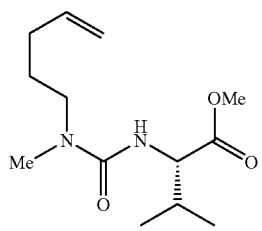

An oven-dried 500 mL round bottom flask under nitrogen was charged with THF (20 mL), N-methylpent-4-en-1-amine (*Org. Lett.* (2005), 7(9), pp 1737-1739) (1.0 g, 10.1 mmol) and methyl (2S)-2-isocyanato-3-methylbutanoate (*J.O.C.* (1992), 57(26), pp 7364-7366) (1.60 g, 10.1 mmol). Contents of the reaction flask were stirred at RT for 2 hours then rotary evaporated to afford the title compound as a colorless oil. LRMS m/e [M+H]$^+$ 257.

Step 2: (2S)-3-Methyl-2-({[methyl(pent-4-en-1-yl)amino]carbonyl}amino)butanoic acid (A18)

A 250 mL round bottom flask under nitrogen was charged with methyl (2S)-3-methyl-2-({[methyl(pent-4-en-1-yl)amino]carbonyl}amino)butanoate from the previous step, THF (40 mL), and aqueous LiOH (1 M, 60 mmol, 60 mL). The reaction mixture was stirred 18 hours. THF was removed by evaporation. The remaining aqueous mixture was poured into water and washed once with EtOAc. The aqueous layer was acidified with 1 M hydrochloric acid and extracted with EtOAc (3×). Combined organic extracts were dried with anhydrous $NaSO_4$, filtered and evaporated to give the title compound as a pale oil (2.34 g, 9.66 mmol, 95%). LRMS m/e $[M+H]^+$ 243.

The following urea intermediates were prepared using the chemistry described for the preparation of (2S)-3-Methyl-2-({[methyl(pent-4-en-1-yl)amino]carbonyl}amino)butanoic acid (as described in Linker A18), by utilizing the appropriate amino acid and amine:

| Int | Amino Acid | Amine | Structure |
|---|---|---|---|
| A19 | L-Norleucine | Pent-4-en-1-amine Ref: Org. Lett. (2005), 7(9), pp 1737-1739. | 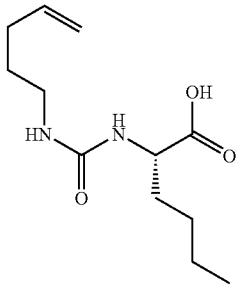 |
| A20 | L-valine | Pent-4-en-1-amine Ref: Org. Lett. (2005), 7(9), pp 1737-1739. | 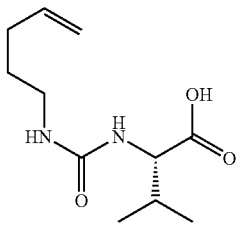 |
| A21 | L-Valine | 1,1-Dimethylpent-4-enylamine Ref: WO 2000/68246 | 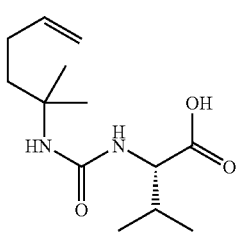 |

The following EXAMPLES were prepared using the designated procedure described above in conjunction with the designated linker described above.

| Ex./Cpd | Structure | Name | LRMS (M + H)+ | Prepared using the appropriate Linker according to the procedure below. | Linker |
|---|---|---|---|---|---|
| 10/ III-13 | 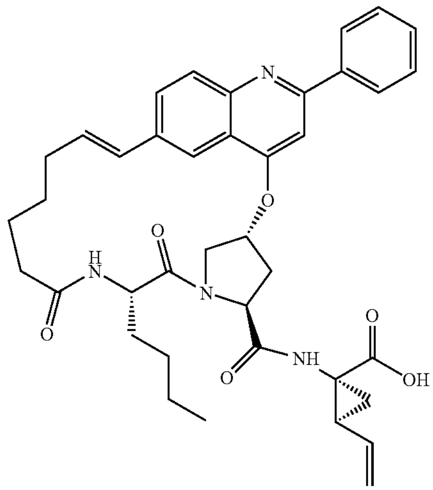 | (1R,2S)-1-({[(2R,4S,7S)-7-Butyl-6,9-dioxo-20-phenyl-3,4,6,7,8,9,10,11,12,13-decahydro-2H-16,18-ethanediylidene-2,5-methanopyrido[3,4-r][1,5,8]oxadiazacyclononadecin-4-yl]carbonyl}amino)-2-vinylcyclopropane carboxylic acid | 665.5 | See Example 1 | A17 |
| 11/ III-14 | 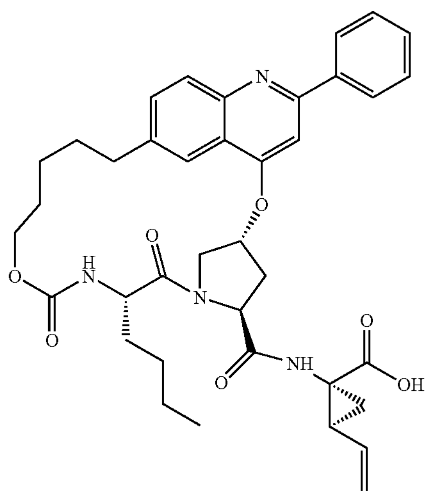 | (1R,2S)-1-({[(2R,4S,7S)-7-Butyl-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclonadecin-4-yl]carbonyl}amino)-2-vinylcyclopropanecarboxylic acid | 669.4 | See Example 2 | A2 |
| 12/ III-15 | 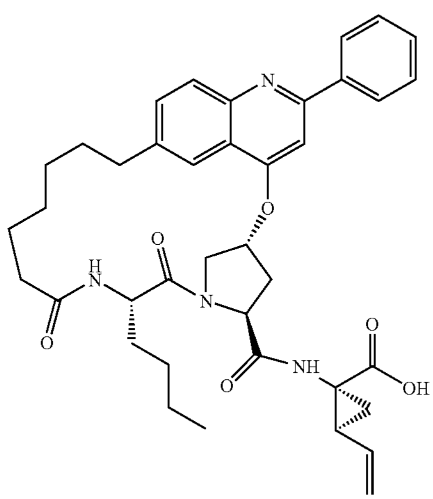 | (1R,2S)-1-({[(2R,4S,7S)-7-Butyl-6,9-dioxo-20-phenyl-3,4,6,7,8,9,10,11,12,13,14,15-dodecahydro-2H-16,18-ethanediylidene-2,5-methanopyrido[3,4-r][1,5,8]oxadiazacyclononadecin-4-yl]carbonyl}amino)-2-vinylcyclopropanecarboxylic acid | 667.5 | See Example 2 | A17 |

-continued

| Ex./Cpd | Structure | Name | LRMS (M + H)+ | Prepared using the appropriate Linker according to the procedure below. | Linker |
|---|---|---|---|---|---|
| 13/III-16 | 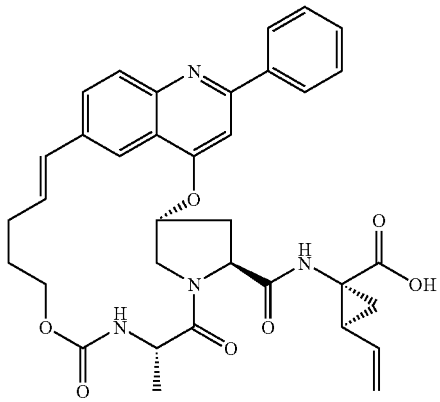 | (1R,2S)-1-({[(2R,4S,7S)-7-Methyl-6,9-dioxo-20-phenyl-3,4,6,7,8,9,12,13-octahydro-2H,11H-16,18-ethanediylidene-2,5-methanopyrido[4,3-k][1,10,3,6]dioxadiazacyclonadecin-4-yl]carbonyl}amino)-2-vinylcyclopropanecarboxylic acid | 625.3 | See Example 1 | A12 |
| 14/III-17 | 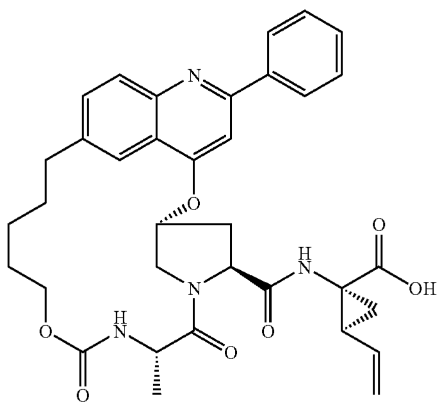 | (1R,2S)-1-({[(2R,4S,7S)-7-Methyl-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclonadecin-4-yl]carbonyl}amino)-2-vinylcyclopropanecarboxylic acid | 627.4 | See Example 2 | A12 |
| 15/III-18 | 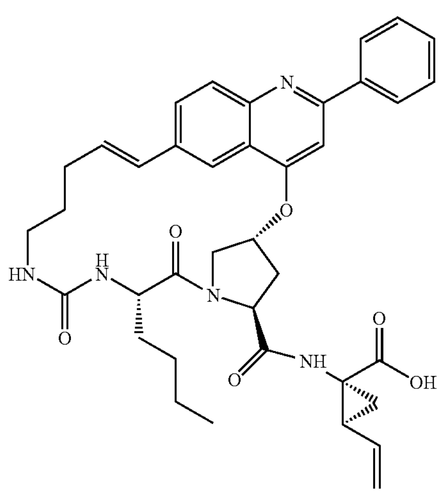 | (1R,2S)-1-({[(2R,4S,7S)-7-Butyl-6,9-dioxo-20-phenyl-3,4,6,7,8,9,10,11,12,13-decahydro-2H-16,18-ethanediylidene-2,5-methanopyrido[3,4-r][1,5,8,10]oxatriazacyclononadecin-4-yl]carbonyl}amino)-2-vinylcyclopropanecarboxylic acid | 666.3 | See Example 1 | A19 |

-continued

| Ex./Cpd | Structure | Name | LRMS (M + H)+ | Prepared using the appropriate Linker according to the procedure below. | Linker |
|---|---|---|---|---|---|
| 16/III-19 | 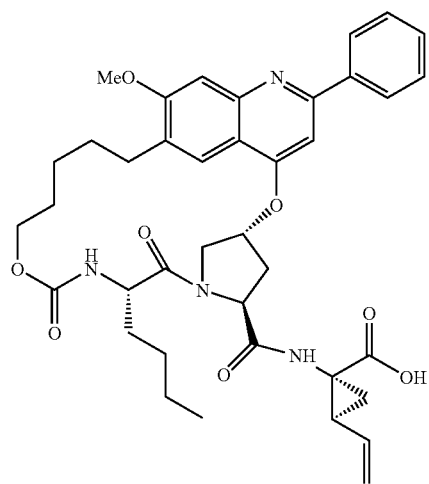 | (1R,2S)-1-({[(2R,4S,7S)-7-Butyl-23-methoxy-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecin-4-yl]carbonyl}amino)-2-vinylcyclopropanecarboxylic acid | 699.4 | See Example 8 | A2 |

EXAMPLE 17

(2R,4S,7S)-7-Butyl-N-((1R,2S)-1-{[(cyclopropylsulfonyl)amino]carbonyl}-2-vinylcyclopropyl)-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecine-4-carboxamide (III-20)

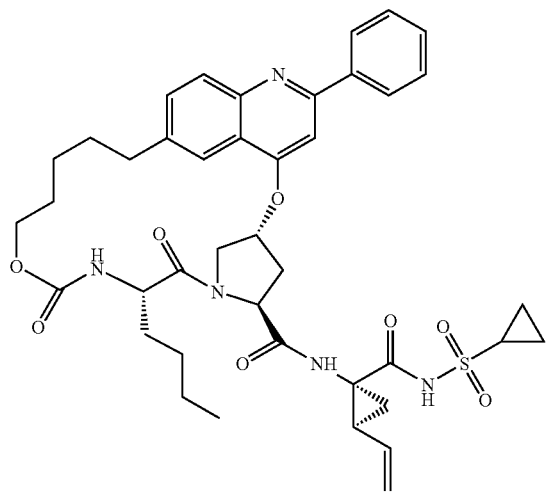

To a solution of EXAMPLE 11 (35 mg, 0.052 mmol) in DMF (0.3 mL) at 40° C. was added carbonyldiimidazole (8 mg, 0.052 mmol) and the reaction mixture was stirred for 1 h. Cyclopropylsulfonamide (10 mg, 0.078 mmol) and DBU (16 mg, 0.01 mmol) were added and the reaction mixture was stirred for 1 h. Following cooling, the reaction mixture was purified on reverse phase HPLC to afford EXAMPLE 17 (22 mg, 54% yield). $^1$H NMR (500 MHz, CD$_3$OD, ppm) δ 8.19 (d, J=1.5 Hz, 1H), 8.14 (d, J=8.8 Hz, 1H), 8.09 (m, 2H), 7.98 (dd, J=8.8, 1.5 Hz, 1H), 7.82 (s, 1H), 7.75 (m, 3H), 6.01 (m, 1H), 5.75 (ddd, J=17.1, 10.3, 8.8 Hz, 1H), 5.29 (dd, J=17.1, 1.5 Hz, 1H), 5.13 (dd, J=10.5, 1.5 Hz, 1H), 4.57 (dd, J=10.7, 6.8 Hz, 1H), 4.41 (t, J=7.6 Hz, 1H), 4.27 (m, 1H), 4.12 (dd, J=12.0, 2.9 Hz, 1H), 3.78 (m, 1H), 3.02-2.95 (m, 2H), 2.83 (m, 1H), 2.68 (dd, J=13.9, 6.6 Hz, 1H), 2.44 (m, 1H), 2.20 (q, J=8.8 Hz, 1H), 1.90 (dd, J=8.1, 5.4 Hz, 1H), 1.88-1.69 (m, 5H), 1.57 (m, 1H), 1.42-1.32 (m, 7H), 1.29 (m, 2H), 1.21 (m, 1H), 1.10 (m, 2H), and 0.96 (m, 3H). LRMS (M+H)+ calcd=772.3. found=772.4.

EXAMPLE 18

(2R,4S,7S)-7-butyl-N-((1R,2R)-1-[(cyclopropylsulfonyl)amino]carbonyl-2-ethylcyclopropyl)-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecine-4-carboxamide (III-21)

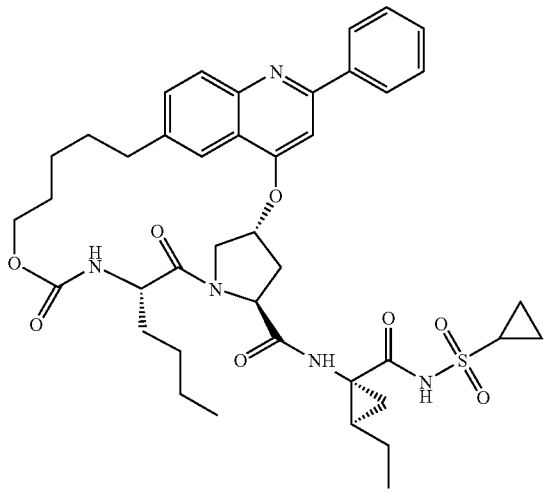

To a solution of EXAMPLE 17 (4 mg, 0.005 mmol) in EtOAc (1 mL) at RT was added 10% Palladium/C (2 mg). The reaction mixture was stirred under balloon pressure $H_2$ for 3 h. The reaction mixture was filtered and concentrated to give EXAMPLE 18 (4 mg, 100% yield). $^1$H NMR (500 MHz, CD$_3$OD, ppm) δ 8.18 (s, 1H), 8.15 (d, J=8.8 Hz, 1H), 8.07 (m, 2H), 7.97 (d, J=8.8 Hz, 1H), 7.80 (s, 1H), 7.75 (m, 3H), 6.02 (s, 1H), 4.57 (m, 1H), 4.40 (t, J=7.5 Hz, 1H), 4.25 (m, 1H), 4.14 (d, J=12.0 Hz, 1H), 3.78 (m, 1H), 3.62 (s, 1H), 3.00 (m, 2H), 2.81 (m, 1H), 2.65 (m, 1H), 2.41 (m, 1H), 2.20 (m, 2H), 2.05 (m, 1H), 1.88-1.40 (m, 9H), 1.42-1.25 (m, 7H), 1.18 (m, 2H), 0.96 (m, 3H), and 0.89 (m, 3H). LRMS (M+H)$^+$ calcd=774.3. found=774.4.

EXAMPLE 19

(2R,4S,7S)—N-((1R,2S)-1-{[(Cyclopropylsulfonyl)amino]carbonyl}-2-vinylcyclopropyl)-7-methyl-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecine-4-carboxamide (III-22)

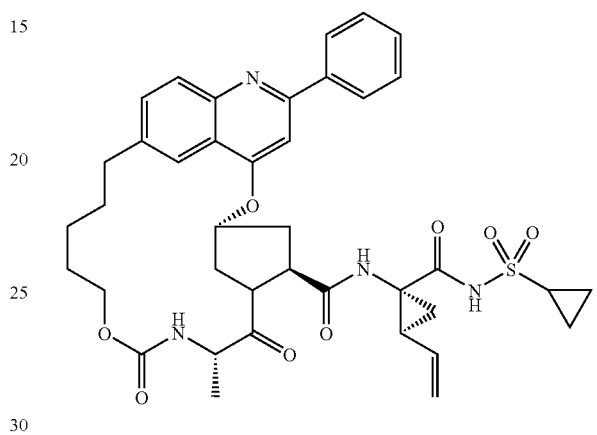

EXAMPLE 19 was prepared according to the procedure for EXAMPLE 17, using EXAMPLE 14 as starting material. $^1$H NMR (500 MHz, CD$_3$OD, ppm) δ 8.23 (s, 1H), 8.14 (d, J=8.8 Hz, 1H), 8.08 (d, J=7.1 Hz, 1H), 8.00 (d, J=8.6 Hz, 1H), 7.82 (s, 1H), 7.75 (m, 3H), 6.03 (s, 1H), 5.72 (m, 1H), 5.28 (d, J=17.3 Hz, 1H), 5.12 (d, J=10.3 Hz, 1H), 4.55 (m, 2H), 4.23 (m, 1H), 4.15 (d, J=12.2 Hz, 1H), 3.80 (m, 1H), 2.97 (m, 2H), 2.84 (m, 1H), 2.71 (q, J=7.6 Hz, 1H), 2.43 (m, 1H), 2.20 (q, J=8.5 Hz, 1H), 1.89 (m, 2H), 1.80 (m, 2H), 1.60 (m, 1H), 1.37 (m, 6H), 1.28 (m, 2H), 1.19 (m, 1H), and 1.08 (m, 2H). LRMS (M+H)$^+$ calcd 730.3. found=730.4.

SCHEME 5

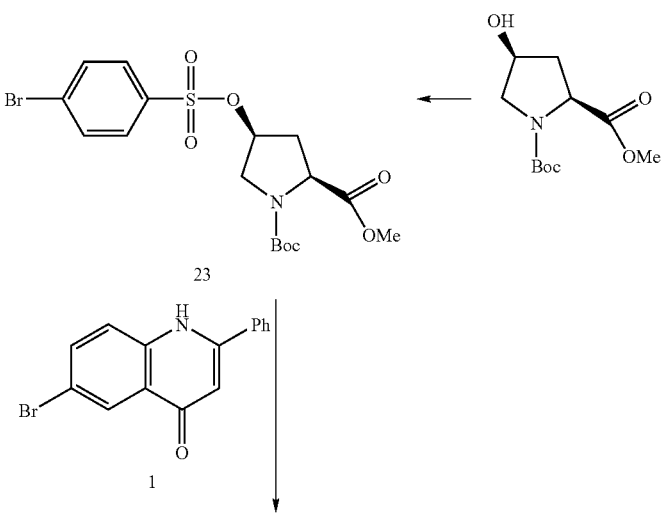

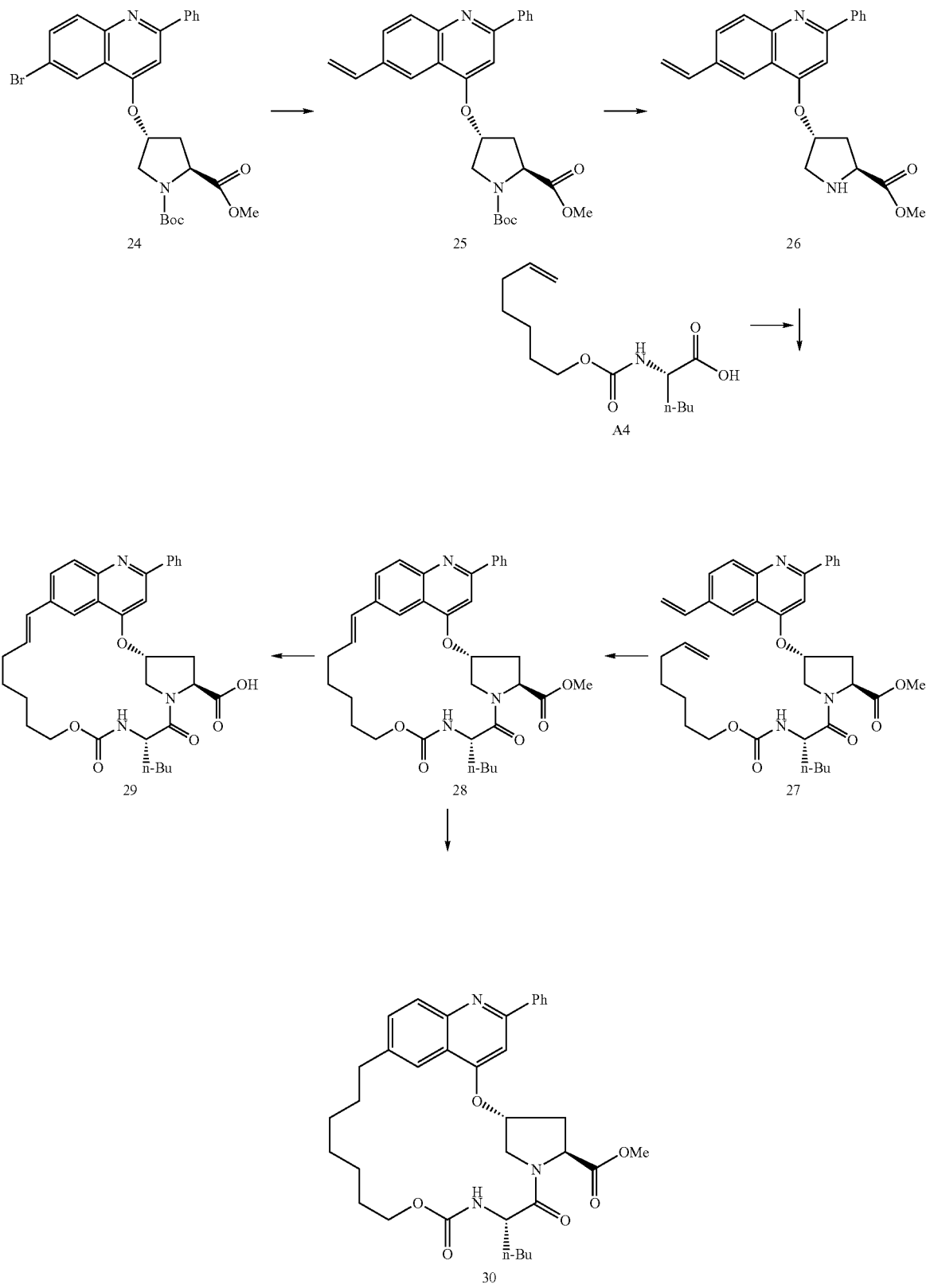

85
86
-continued
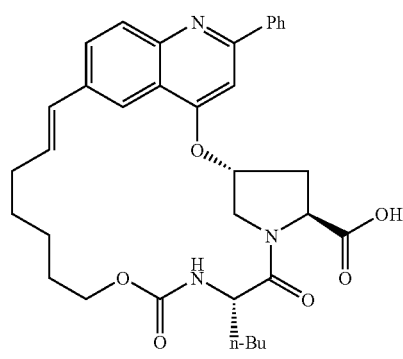
29
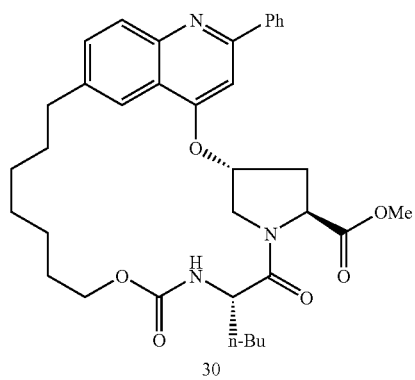
30
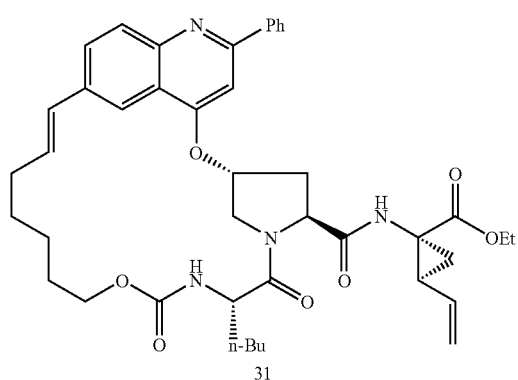
31
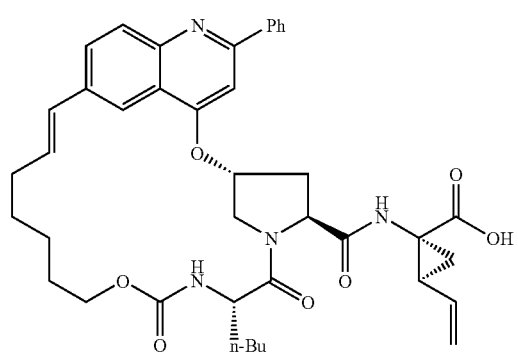
Ex 20
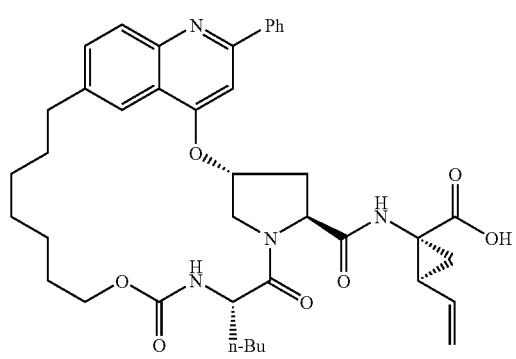
Ex 21

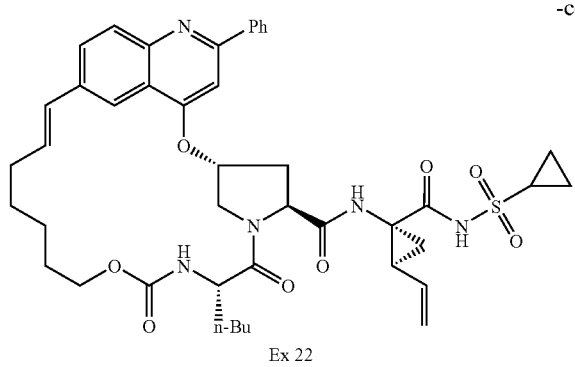

Ex 22

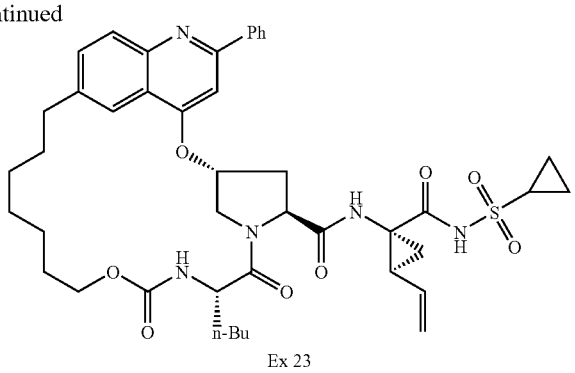

Ex 23

EXAMPLE 20

(1R,2S)-1-({[(2R,4S,7S)-7-Butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosin-4-yl]carbonyl}amino)-2-vinylcyclopropanecarboxylic acid (III-23)

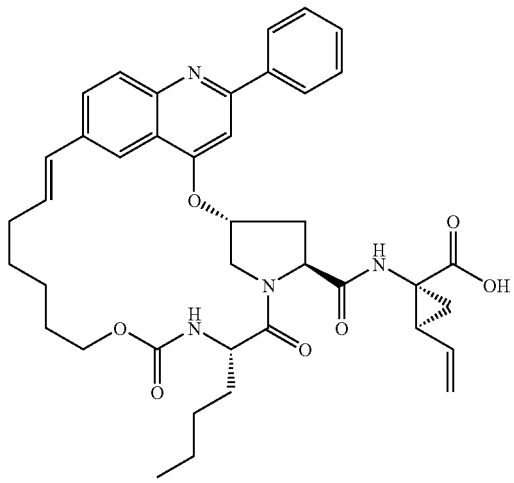

Step 1: 1-tert-Butyl 2-methyl (2S,4S)-4-{[(4-bromophenyl)sulfonyl]oxy}pyrrolidine-1,2-dicarboxylate

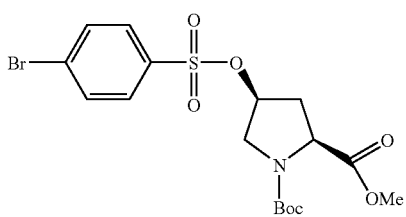

23

To a solution of 1-tert-butyl 2-methyl (2S,4S)-4-hydroxy-pyrrolidine-1,2-dicarboxylate (2.15 g, 8.76 mmol) and DABCO (1.57 g, 14.0 mmol) in PhMe (10 mL) at RT was added a solution of brosyl chloride (3.14 g, 12.3 mmol) in PhMe (5 mL). A white precipitate formed, the reaction mixture was stirred for 20 min and filtered. The filtrate was partitioned between EtOAc and saturated aqueous NaHCO$_3$. The layers were separated and the organic was washed with 1 M HCl, water and brine, dried over Na$_2$SO$_4$, filtered and concentrated. The resulting oil, 1-tert-butyl 2-methyl (2S,4S)-4-{[(4-bromophenyl)sulfonyl]oxy}pyrrolidine-1,2-dicarboxylate 23 (4.0 g, 98% yield), was used without further purification. LRMS (M+Na)$^+$ Calcd.: 488. found 488.

Step 2: 1-tert-Butyl 2-methyl (2S,4R)-4-[(6-bromo-2-phenylquinolin-4-yl)oxy]pyrrolidine-1,2-dicarboxylate

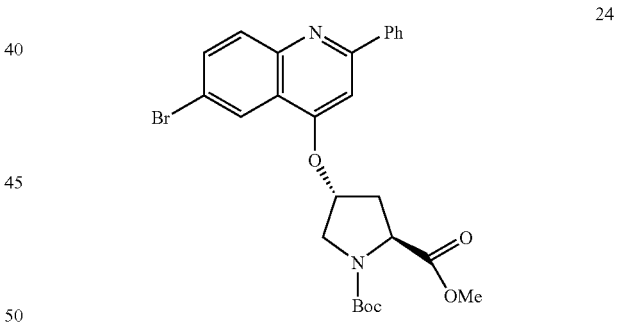

24

To a solution of 1-tert-butyl 2-methyl (2S,4S)-4-{[(4-bromophenyl)sulfonyl]oxy}pyrrolidine-1,2-dicarboxylate 23 (14.0 g, 30.2 mmol) and 6-bromo-2-phenylquinolin-4(1H)-one (1, 9.5 g, 31.7 mmol) in N-methylpyrrolidine (100 mL) was added cesium carbonate (14.7 g, 45.2 mmol). The reaction mixture was heated to 45° C. and stirred for 5 h and cooled. The reaction mixture was poured onto EtOAc and water and the white solids were removed by filtration. The layers were separated and the organic was washed with saturated aqueous NaHCO$_3$, water and brine, dried over Na$_2$SO$_4$, filtered and concentrated. The residue was purified on silica gel (gradient elution 5% to 45% EtOAc in hexanes) to give 1-tert-butyl 2-methyl (2S,4R)-4-[(6-bromo-2-phenylquinolin-4-yl)oxy]pyrrolidine-1,2-dicarboxylate 24 (9.9 g, 62% yield) as a pale yellow solid. LRMS (M+H)$^+$ Calcd.: 527. found 527.

Step 3: 1-tert-Butyl 2-methyl (2S,4R)-4-[(2-phenyl-6-vinylquinolin-4-yl)oxy]pyrrolidine-1,2-dicarboxylate

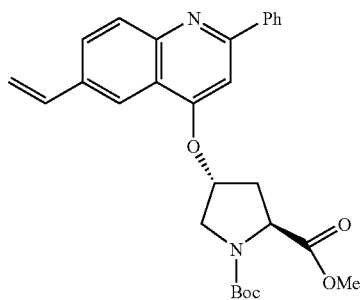

25

To a solution of 1-tert-butyl 2-methyl (2S,4R)-4-[(6-bromo-2-phenylquinolin-4-yl)oxy]pyrrolidine-1,2-dicarboxylate 24 (1.45 g, 2.75 mmol) in toluene (20 mL) was added vinyltributyltin (0.96 mL, 3.3 mmol) and tetrakistriphenylphosphine palladium (318 mg, 0.27 mmol). The mixture was then heated to 110° C. for 3 h, at which time, LC-MS revealed the disappearance of starting material. The reaction mixture was concentrated and purified on silica gel (gradient elution 15% to 50% EtOAc in hexanes) to give 1-tert-butyl 2-methyl (2S,4R)-4-[(2-phenyl-6-vinylquinolin-4-yl)oxy]pyrrolidine-1,2-dicarboxylate 25 (0.74 g, 56% yield) as a yellow solid. LRMS (M+H)$^+$ Calcd.: 475. found 475.

Step 4: Methyl (4R)-4-[(2-phenyl-6-vinylquinolin-4-yl)oxy]-L-prolinate chloride

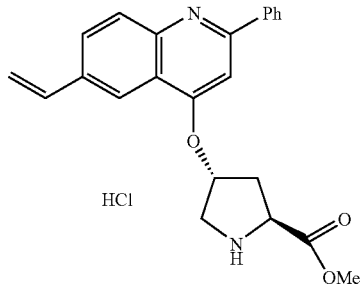

26

To a flask containing 1-tert-butyl 2-methyl (2S,4R)-4-[(2-phenyl-6-vinylquinolin-4-yl)oxy]pyrrolidine-1,2-dicarboxylate 25 (740 mg, 1.56 mmol) was added a 4 M solution of HCl in dioxane (15 mL). After 2 hrs, LC-MS analysis indicated complete consumption of the starting material. The reaction mixture was concentrated to give methyl (4R)-4-[(2-phenyl-6-vinylquinolin-4-yl)oxy]-L-prolinate chloride 26 (700 mg, 99% yield) as a yellow powder which was used without further purification. LRMS (M+H)$^+$ Calcd.: 375. found 375.

Step 5: Methyl N-[(hept-6-enyloxy)carbonyl]-L-norleucyl-(4R)-4-[(2-phenyl-6-vinylquinolin-4-yl)oxy]-L-prolinate

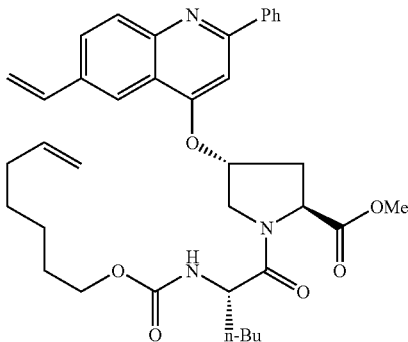

27

To a solution of methyl (4R)-4-[(2-phenyl-6-vinylquinolin-4-yl)oxy]-L-prolinate chloride 26 (300 mg, 0.73 mmol) and N-[(hept-6-en-1-yloxy)carbonyl]-L-norleucine A4 (258 mg, 0.95 mmol) was added EDC (280 mg, 1.46 mmol), HOAt (200 mg, 1.46 mmol) and DIPEA (0.59 mL, 2.9 mmol). The reaction mixture was stirred for 2 h at RT and then worked-up with 1N HCl and EtOAc. The organic layer was washed with brine and dried over Na$_2$SO$_4$, filtered and concentrated. The crude product was purified on silica gel (gradient elution 10% to 100% EtOAc in hexanes) to give methyl N-[(hept-6-enyloxy)carbonyl]-L-norleucyl-(4R)-4-[(2-phenyl-6-vinylquinolin-4-yl)oxy]-L-prolinate 27 (411 mg, 89% yield) as a colorless oil. LRMS (M+H)$^+$ Calcd.: 628. found 628.

Step 6: Methyl (2R,4S,7S)-7-butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosine-4-carboxylate

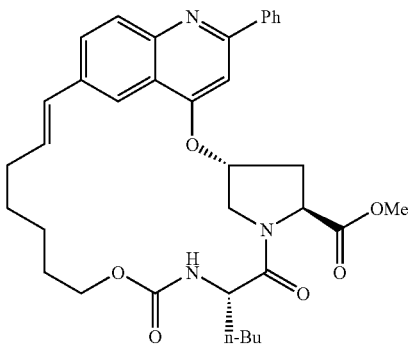

28

To a degassed (N$_2$, 15 min) solution of methyl N-[(hept-6-enyloxy)carbonyl]-L-norleucyl-(4R)-4-[(2-phenyl-6-vinylquinolin-4-yl)oxy]-L-prolinate 27 (400 mg, 0.64 mmol) in DCE (100 mL) was added the Zhan ruthenium metathesis catalyst RC-301 (Zhan Catalyst I, RC-301, Zannan Pharma Ltd.) (42 mg, 0.06 mmol). The reaction was then heated to 100° C. and stirred for 2 hrs. LC-MS analysis indicated nearly complete consumption of the starting material had occurred. The reaction mixture was concentrated and the crude product was purified on silica gel (gradient elution, 10% to 100% EtOAc in hexane) to yield methyl (2R,4S,7S)-7-butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosine-4-carboxylate 28 (347 mg, 90% yield) as a tan solid. LRMS (M+H)$^+$ Calcd.: 600. found 600.

Step 7: (2R,4S,7S)-7-Butyl-6,9-dioxo-22-phenyl-3,4,
6,7,8,9,12,13,14,15-decahydro-2H,11H-18,20-
ethanediylidene-2,5-methanopyrido[4,3-k][1,10,3,6]
dioxadiazacyclohenicosine-4-carboxylic acid

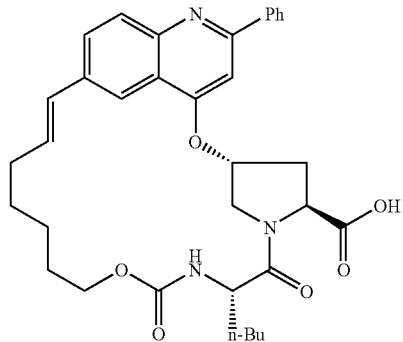

29

A solution of methyl (2R,4S,7S)-7-butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosine-4-carboxylate 28 (170 mg, 0.29 mmol) in THF (2 mL), MeOH (1 mL), and LiOH (1 N, 1 mL) was heated to 40° C. and stirred for 1 h, at which time complete consumption of the methyl ester starting material was observed by LC-MS. The mixture was then worked-up with 0.5 N HCl and EtOAc. The organic layer was then dried over Na$_2$SO$_4$, filtered and concentrated. The product, (2R,4S,7S)-7-butyl-6,9-dioxo-22-phenyl-3,4,6,7,8,9,12,13,14,15-decahydro-2H,11H-18,20-ethanediylidene-2,5-methano pyrido[4,3-k][1,10,3,6]dioxadiazacyclohenicosine-4-carboxylic acid 29 (153 mg, 92% yield) was used with no further purification. LRMS (M+H)]$^+$ Calcd.: 586. found 586.

Step 8: Ethyl (1R,2S)-1-({[(2R,4S,7S)-7-butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosin-4-yl]carbonyl}amino)-2-vinylcyclopropanecarboxylate

31

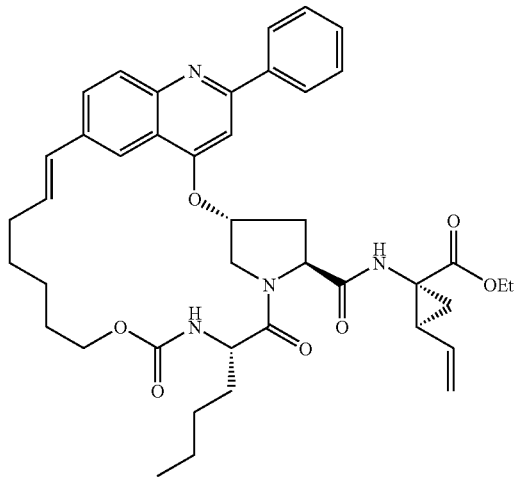

To a solution of (2R,4S,7S)-7-butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosine-4-carboxylic acid 29 (150 mg, 0.26 mmol) in DMF (5 mL) was added ethyl (1R,2S)-1-amino-2-vinylcyclopropanecarboxylate (Llinas-Brunet et al., U.S. Pat. No. 6,323,180) (98 mg, 0.52 mmol), TBTU (247 mg, 0.76 mmol) and DIPEA (0.44 mL, 2.5 mmol) and the reaction mixture was stirred at RT for 2 h. The reaction mixture was partitioned between EtOAc and saturated aqueous NaHCO$_3$. The layers were separated and the organic was washed with water and brine, dried over Na$_2$SO$_4$, filtered and concentrated. The crude product was purified on silica gel (gradient elution, 10% to 100% EtOAc in hexane) to yield ethyl (1R,2S)-1-({[(2R,4S,7S)-7-butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosin-4-yl]carbonyl}amino)-2-vinylcyclopropanecarboxylate 31 (157 mg, 85%) as a white foam. LRMS (M+H)$^+$ Calcd.: 723. found 723.

Step 9: (1R,2S)-1-({[(2R,4S,7S)-7-Butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosin-4-yl]carbonyl}amino)-2-vinylcyclopropanecarboxylic acid (EXAMPLE 20)

To a solution of ethyl (1R,2S)-1-({[(2R,4S,7S)-7-butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosin-4-yl]carbonyl}amino)-2-vinylcyclopropanecarboxylate 31 (150 mg, 0.21 mmol) in THF (2 mL) and EtOH (1 mL) was added 1 M LiOH (2 mL). The reaction mixture was heated to 50° C. and stirred for 5 h. The reaction mixture was cooled, acidified to pH=6 with 1 M HCl and extracted with EtOAc three times. The combined organic layers were washed with water, brine, dried over Na$_2$SO$_4$, filtered and concentrated. Purification by reverse phase HPLC gave (1R,2S)-1-({[(2R,4S,7S)-7-butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosin-4-yl]carbonyl}amino)-2-vinylcyclopropanecarboxylic acid (EXAMPLE 20) (127 mg, 88% yield) as a white foam. $^1$H NMR (500 MHz, CD$_3$OD, ppm) δ 8.28 (s, 1H), 8.12 (s, 2H), 8.08 (d, J=6.8 Hz, 2H), 7.72 (m, 4H), 6.68 (d, J=16.1 Hz, 1H), 6.51 (m, 1H), 5.83 (m, 2H), 5.28 (d, J=17.1 Hz, 1H), 5.09 (d, J=10.5 Hz, 1H), 4.70 (d, J=11.9 Hz, 1H), 4.56 (m, 2H), 4.27 (m, 1H), 4.10 (d, J=12.2 Hz, 1H), 3.29 (m, 1H), 2.76 (m, 1H), 2.56 (m, 1H), 2.38 (q, J=4.6 Hz, 2H), 2.18 (q, J=8.8 Hz, 1H), 1.84 (m, 1H), 1.72 (m, 2 H), 1.66 (m, 4H), 1.44 (m, 7H), and 0.98 (t, J=7.1 Hz, 3H). LRMS (M+H)$^+$ calcd=695.3. found 695.4.

EXAMPLE 21

(1R,2S)-1-({[(2R,4S,7S)-7-Butyl-6,9-dioxo-22-phenyl-3,4,6,7,8,9,12,13,14,15,16,17-dodecahydro-2H,11H-18,20-ethanediylidene-2,5-methanopyrido[4,3-k][1,10,3,6]dioxadiazacyclohenicosin-4-yl]carbonyl}amino)-2-vinylcyclopropanecarboxylic acid (III-24)

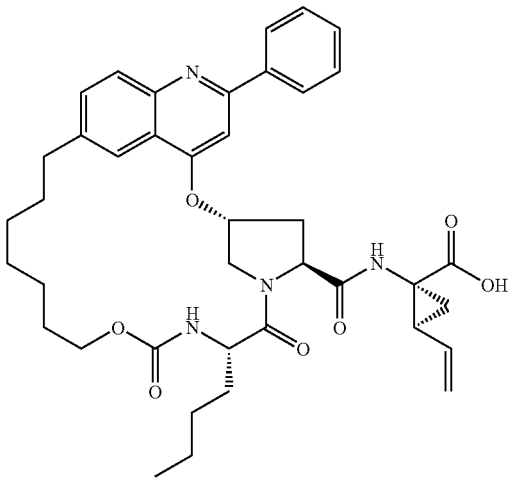

Step 1: Methyl (2R,4S,7S)-7-butyl-6,9-dioxo-22-phenyl-3,4,6,7,8,9,12,13,14,15,16,17-dodecahydro-2H,11H-18,20-ethanediylidene-2,5-methanopyrido[4,3-k][1,10,3,6]dioxadiazacyclohenicosine-4-carboxylate

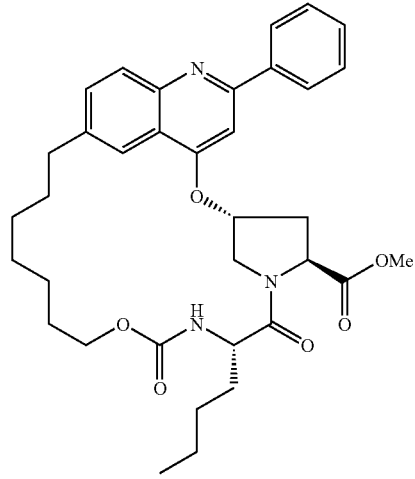

A solution of methyl (2R,4S,7S)-7-butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosine-4-carboxylate 28 (EXAMPLE 20, Step 6) (125 mg, 0.21 mmol) and 10% Pd/C (10 mg) in EtOAc (5 mL) at RT was stirred under balloon pressure $H_2$ for 2 h. The reaction mixture was filtered and concentrated to give methyl (2R,4S,7S)-7-butyl-6,9-dioxo-22-phenyl-3,4,6,7,8,9,12,13,14,15,16,17-dodecahydro-2H,11H-18,20-ethanediylidene-2,5-methanopyrido[4,3-k][1,10,3,6]dioxadiazacyclohenicosine-4-carboxylate 30 (121 mg, 96% yield) which was used with no further purification. LRMS (M+H)$^+$= 602.

Steps 2-4: (1R,2S)-1-({[(2R,4S,7S)-7-Butyl-6,9-dioxo-22-phenyl-3,4,6,7,8,9,12,13,14,15,16,17-dodecahydro-2H,11H-18,20-ethanediylidene-2,5-methanopyrido[4,3-k][1,10,3,6]dioxadiazacyclohenicosin-4-yl]carbonyl}amino)-2-vinylcyclopropanecarboxylic acid (EXAMPLE 21)

EXAMPLE 21 was prepared using the procedure for EXAMPLE 20 (Steps 7, 8 and 9) using 30 as starting material instead of 28. $^1$H NMR (500 MHz, CD$_3$OD, ppm) δ 8.10 (m, 4H), 7.97 (d, J=8.3 Hz, 1H), 7.74 (m, 4H), 5.90 (s, 1H), 5.85 (m, 1H), 5.28 (d, J=16.9 Hz, 1H), 5.10 (d, J=10.3 Hz, 1H), 4.67 (t, J=9.0 Hz, 1H), 4.63 (d, J=12.2 Hz, 1H), 4.41 (t, J=6.8 Hz, 1H), 4.14 (d, J=12.7 Hz, 1H), 4.04 (m, 1H), 3.66 (m, 1H), 2.95 (m, 1H), 2.90 (m, 1H), 2.57 (m, 1H), 2.20 (q, J=8.3 Hz, 1H), 1.81 (m, 3H), 1.69 (m, 1H), 1.64 (m, 1H), 1.56 (m, 1H), 1.40 (m, 12H), and 0.95 (t, J=6.8 Hz, 3H). LRMS (M+H)$^+$ calcd=697.4. found=697.5.

EXAMPLE 22

(2R,4S,7S)-7-Butyl-N-((1R,2S)-1-{[(cyclopropylsulfonyl)amino]carbonyl}-2-vinylcyclopropyl)-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosine-4-carboxamide (III-25)

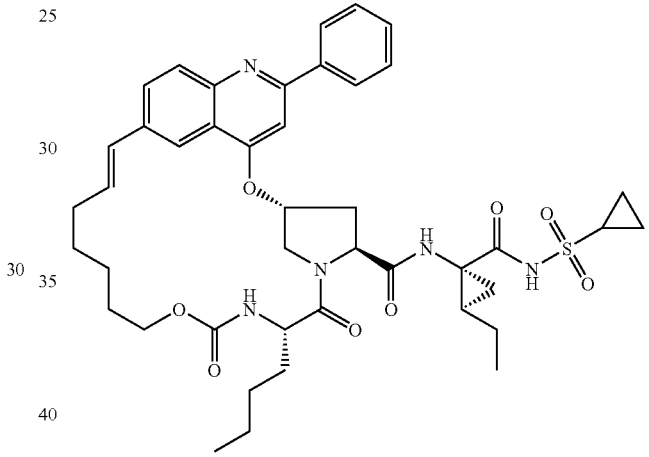

To a solution of (1R,2S)-1-({[(2R,4S,7S)-7-butyl-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosin-4-yl]carbonyl}amino)-2-vinylcyclopropanecarboxylic acid (EXAMPLE 20) (50 mg, 0.07 mmol) in DMF (1 mL) at 40° C. was added carbonyldiimidazole (18 mg, 0.1 mmol) and the reaction mixture was stirred for 1 h. Cyclopropylsulfonamide (13 mg, 0.1 mmol) and DBU (0.032 mL, 0.2 mmol) were added and the reaction mixture was stirred for 1 h. Following cooling, the reaction mixture was purified on reverse phase HPLC to afford (2R,4S,7S)-7-butyl-N-((1R,2S)-1-{[(cyclopropylsulfonyl)amino]carbonyl}-2-vinylcyclopropyl)-6,9-dioxo-22-phenyl-3,4,6,7,8,9,12,13,14,15-decahydro-2H,11H-18,20-ethanediylidene-2,5-methanopyrido[4,3-k][1,10,3,6]dioxadiazacyclohenicosine-4-carboxamide (EXAMPLE 22) (16 mg, 27% yield). $^1$H NMR (500 MHz, CD$_3$OD, ppm) δ 8.30 (s, 1H), 8.08 (m, 4H), 7.75 (m, 4H), 6.68 (d, J=15.9 Hz, 1H), 6.55 (m, 1H), 5.92 (s, 1H), 5.72 (m, 1H), 5.27 (d, J=17.3 Hz, 1H), 5.11 (d, J=10.5 Hz, 1H), 4.74 (d, J=11.5 Hz, 1H), 4.53 (t, J=8.06 Hz, 1H), 4.48 (m, 1H), 4.36 (m, 1H), 4.15 (d, J=12.2 Hz, 1H), 3.89 (m, 1H), 2.96 (m, 1H), 2.74 (m, 1H), 2.45 (m, 1H), 2.39 (m, 2H), 2.17 (q, J=8.8 Hz, 1H), 1.88 (m, 1H), 1.83 (m, 1H), 1.73 (m, 3H), 1.64 (m, 2H), 1.44 (m, 6H), 1.34 (m, 1H), 1.26 (m, 1H), 1.22 (m, 1H), 1.09 (m, 1H), and 0.97 (t, J=6.8 Hz, 3H). LRMS (M+H)$^+$ calcd=798.3. found 798.4.

EXAMPLE 23

(2R,4S,7S)-7-Butyl-N-((1R,2S)-1-{[(cyclopropylsulfonyl)amino]carbonyl}-2-vinylcyclopropyl)-6,9-dioxo-22-phenyl-3,4,6,7,8,9,12,13,14,15,16,17-dodecahydro-2H,11H-18,20-ethanediylidene-2,5-methanopyrido[4,3-k][1,10,3,6]dioxadiazacyclohenicosine-4-carboxamide (III-26)

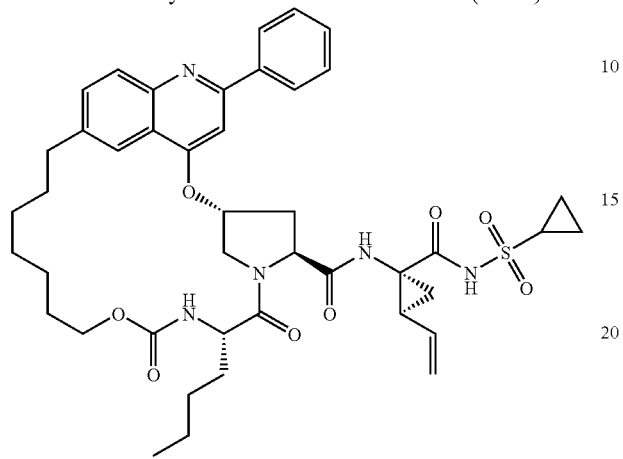

EXAMPLE 23 was prepared using the procedure described for EXAMPLE 22 by using EXAMPLE 21 as starting material instead of EXAMPLE 20. $^1$H NMR (500 MHz, CD$_3$OD, ppm) δ 8.16 (d, J=8.6 Hz, 1H), 8.10 (m, 3H), 8.07 (d, J=8.8 Hz, 1H), 7.80 (s, 1H), 7.75 (m, 3H), 5.97 (s, 1H), 5.76 (m, 1H), 5.31 (d, J=17.1 Hz, 1H), 5.13 (d, J=10.5 Hz, 1H), 4.64 (m, 2H), 4.40 (t, J=8.3 Hz, 1H), 4.16 (d, J=12.5 Hz, 1H), 4.07 (m, 1H), 3.63 (m, 1H), 2.96 (m, 2H), 2.89 (m, 1H), 2.76 (m, 1H), 2.48 (m, 1H), 2.23 (q, J=8.8 Hz, 1H), 1.91 (m, 1H), 1.67 (m, 3H), 1.56 (m, 1H), 1.41 (m, 1H), 1.40-1.19 (m, 14H), 1.10 (m, 2H), and 0.94 (t, J=6.8 Hz, 3H). LRMS (M+H)$^+$ calcd=800.4. found=800.5.

The following EXAMPLES were prepared using the designated procedure described above in conjunction with the designated linker described above.

| Ex/Cpd | Structure | Name | LRMS M+H)$^+$ | Prepared using the apropriate Linker according to the procedure below | Linker |
|---|---|---|---|---|---|
| 24/III-27 | 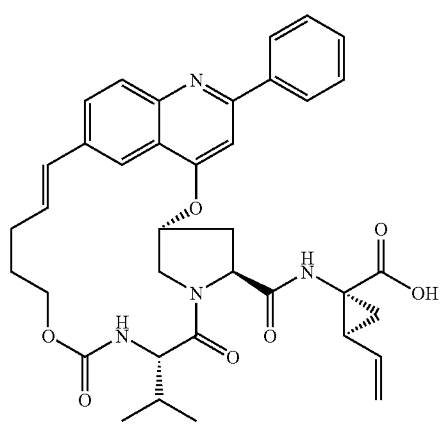 | (1R,2S)-1-({[(2R,4S,7S)-7-Isopropyl-6,9-dioxo-20-phenyl-3,4,6,7,8,9,12,13-octahydro-2H,11H-16,18-ethanediylidene-2,5-methano pyrido[4,3-k][1,10,3,6]dioxa diazacyclononadecin-4-yl]carbonyl}amino)-2-vinyl cyclopropanecarboxylic acid | 653.2 | See Example 20 | A9 |

-continued

| Ex/Cpd | Structure | Name | LRMS M + H)+ | Prepared using the apropriate Linker according to the procedure below | Linker |
|---|---|---|---|---|---|
| 25/III-28 | 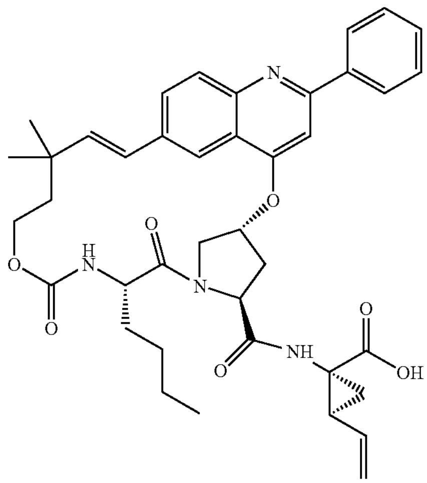 | (1R,2S)-1-({[(2R,4S,7S)-7-Butyl-13,13,-dimethyl-6,9-dioxo-20-phenyl-3,4,6,7,8,9,12,13-octahydro-2H,11H-16,18-ethanediylidene-2,5-methanopyrido[4,3-k][1,10,3,6]dioxadiazacyclononadecin-4-yl]carbonyl}amino)-2-vinylcyclopropane carboxylic acid | 695.5 | See Example 20 | A5 |
| 26/III-29 | 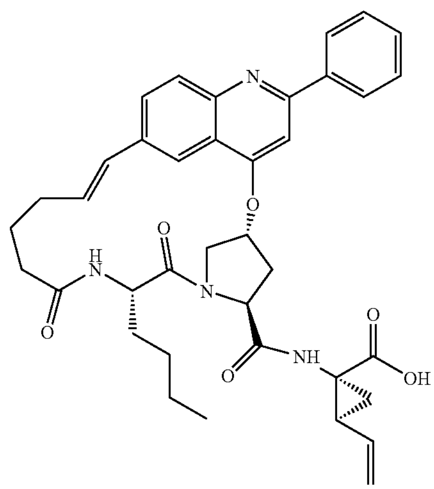 | (1R,2S)-1-({[(2R,4S,7S)-7-Butyl-6,9-dioxo-19-phenyl-3,4,7,8,9,10,11,12-octahydro-2H,6H-15,17-ethanediylid ene-2,5-methano pyrido[3,4-q][1,5,8]oxadiazacyclooctadecin-4-yl]carbonyl}amino)-2-vinylcyclopropane carboxylic acid | 651.3 | See Example 20 | A16 |
| 27/III-30 | 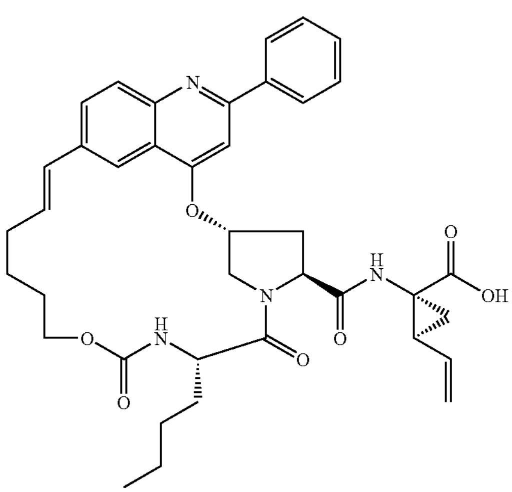 | (1R,2S)-1-({[(2R,4S,7S)-7-Butyl-6,9-dioxo-21-phenyl-3,4,6,7,8,9,11,12,13,14-decahydro-2H-17,19-ethane diylidene-2,5-methanopyrido[4,3-k][1,10,3,6]dioxadiaza cycloicosin-4-yl]carbonyl}amino)-2-vinylcyclopropane carboxylic acid | 681.4 | See Example 20 | A3 |

-continued

| Ex/Cpd | Name | LRMS M + H)+ | Prepared using the apropriate Linker according to the procedure below | Linker |
|---|---|---|---|---|
| 28/III-31 | (1R,2S)-1-({[(2R,4S,7S)-7-Butyl-6,9-dioxo-21-phenyl-3,4,6,7,8,9,11,12,13,14,15,16-dodecahydro-2H-17,19-ethanediylidene-2,5-methano pyrido[4,3-k][1,10,3,6]dioxadiazacycloicosin-4-yl]carbonyl}amino)-2-vinyl cyclopropanecarboxylic acid | 683.5 | See Example 21 | A3 |
| 29/III-32 | (1R,2S)-1-({[(2R,4S,7S)-7-Butyl-6,9-dioxo-19-phenyl-3,4,7,8,9,10,11,12,13,14,-decahydro-2H,6H-15,17-ethanediylidene-2,5-methano pyrido[3,4-q][1,5,8]oxadiazacyclooctadecin-4-yl]carbonyl}amino)-2-vinyl cyclopropanecarboxylic acid | 653.4 | See Example 21 | A16 |
| 30/III-33 | (1R,2S)-1-({[(2R,4S,7S)-7-Isopropyl-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecin-4-yl]carbonyl}amino)-2-vinylcyclopropanecarboxylic acid | 655.3 | See Example 21 | A9 |

-continued

| Ex/ Cpd | Structure | Name | LRMS M + H)+ | Prepared using the apropriate Linker according to the procedure below | Linker |
|---|---|---|---|---|---|
| 31/ III-34 | 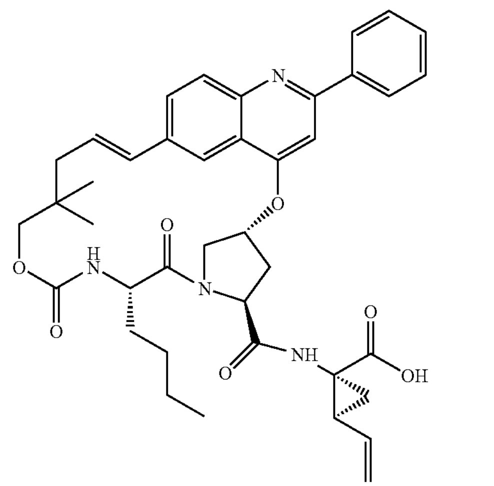 | (1R,S)-1-({[(2R,4S,7S)-7-Butyl-12,12-dimethyl-6,9-dioxo-20-phenyl-3,4,6,7,8,9,12,13-octahydro-2H,11H-16,18-ethanediylidene-2,5-methanopyrido[4,3-k][1,10,3,6]dioxadiazacyclononadecin-4-yl]carbonyl}amino)-2-vinylcyclopropane carboxylic acid | 695.3 | See Example 20 | A6 |
| 32/ III-35 | 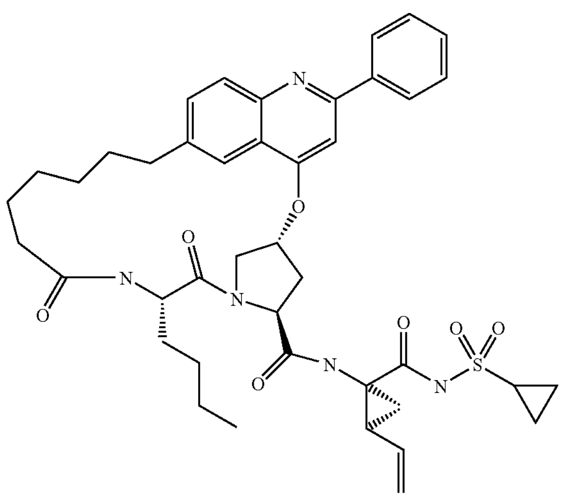 | (2R,4S,7S)-7-Butyl-N-((1R,2S)-1-{[(cyclopropylsulfonyl)amino]carbonyl}-2-vinylcyclopropyl)-6,9-dioxo-20-phenyl-3,4,6,7,8,9,10,11,12,13,14,15-dodecahydro-2H-16,18-ethanediylidene-2,5-methanopyrido[3,4-r][1,5,8]oxadiazacyclononadecine-4-carboxamide | 770.4 | See Example 23 | A17 |
| 33/ III-36 | 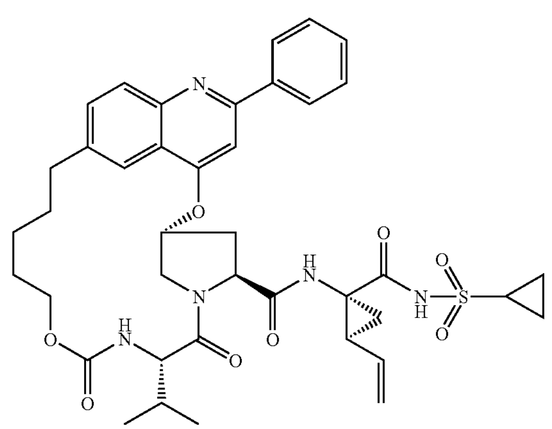 | (2R,4S,7S)-N-((1R,2S)-1-{[(Cyclopropylsulfonyl)amino]carbonyl}-2-vinylcyclopropyl)-7-isopropyl-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecine-4-carboxamide | 758.2 | See Example 23 | A9 |

-continued

| Ex/Cpd | Structure | Name | LRMS M+H)+ | Prepared using the apropriate Linker according to the procedure below | Linker |
| --- | --- | --- | --- | --- | --- |
| 34/ III-37 | 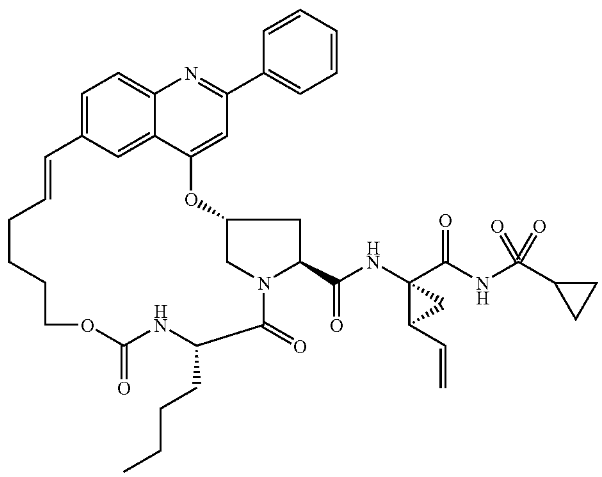 | (2R,4S,7S)-7-butyl-N-((1R,2S)-2-{[(Cyclopropyl sulfonyl)amino]carbonyl}-2-vinylcyclopropyl)-6,9-dioxo-21-phenyl-3,4,6,7,8,9,11,12,13,14-decahydro-2H-17,19-ethanediylidene-2,5-methano pyrido[4,3-k][1,10,3,6]dioxa diazacycloicosine-4-carboxamide | 784.4 | See Example 22 | A3 |
| 35/ III-38 | 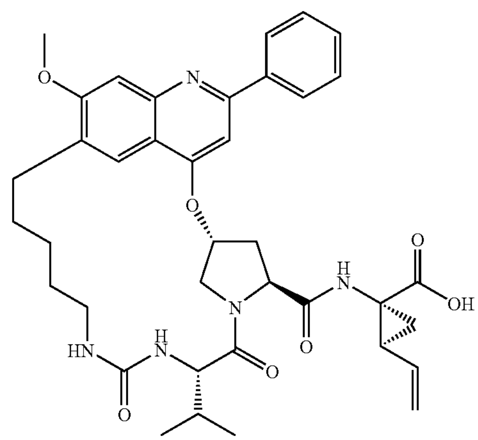 | (1R,2S)-1-({[(2R,4S,7S)-7-Isopropyl-23-methoxy-6,9-dioxo-20-phenyl-3,4,6,7,8,9,10,11,12,13,14,15-dodeca hydro-2H-16,18-ethane diylidene-2,5-methanopyrido[3,4-r][1,5,8,10]oxatriaza cyclononadecin-4-yl]carbonyl}amino)-2-vinyl cyclopropanecarboxylic acid | 684.3 | See Example 21; for MeO-quinoline, see Example 8, step 3 | A20 |
| 36/ III-39 | 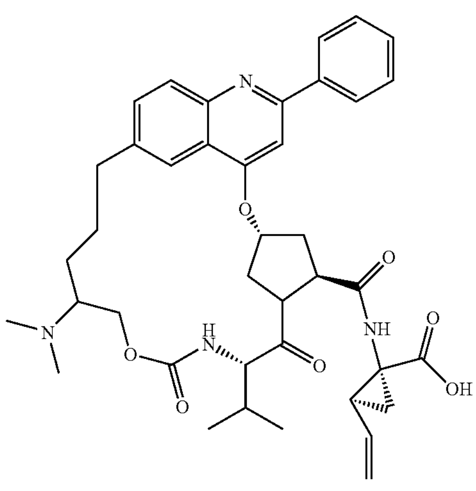 | (1R,2S)-1-({[(2R,4S,7S)-12-(Dimethylamino)-7-isopropyl-6,9-dioxo-20-phenyl-3,4,6,7,8,9,12,13,14,15-decahydro-2H,11H-16,18-ethanediylidene-2,5-methano pyrido[4,3-k][1,10,3,6] dioxadiazacyclononadecin-4-yl]carbonyl}amino)-2-vinylcyclopropane carboxylic acid | 698.4 | See Example 21 | A14 |

-continued

| Ex/Cpd | Structure | Name | LRMS M+H)+ | Prepared using the apropriate Linker according to the procedure below | Linker |
|---|---|---|---|---|---|
| 37/III-40 | 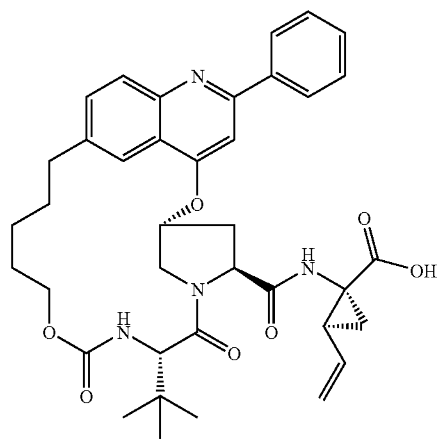 | (1R,2S)-1-({[(2R,4S,7S)-7-tert-Butyl-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecin-4-yl]carbonyl}amino)-2-vinylcyclopropanecarboxylic acid | 669.3 | See Example 21 | A10 |
| 38/III-41 | 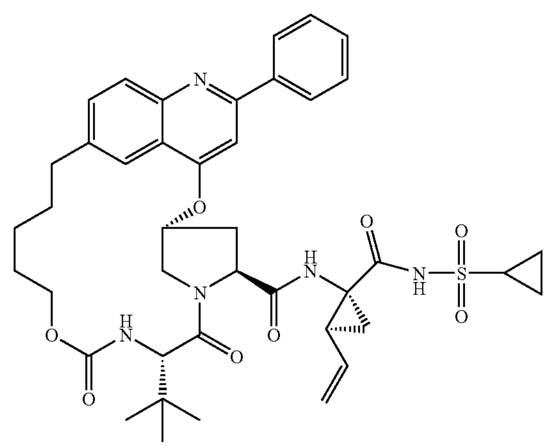 | (2R,4S,7S)-7-tert-Butyl-N-((1R,2S)-1-{[(cyclopropylsulfonyl)amino]carbonyl}-2-vinylcyclopropyl)-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecine-4-carboxamide | 772.3 | See Example 23 | A10 |
| 39/III-42 | 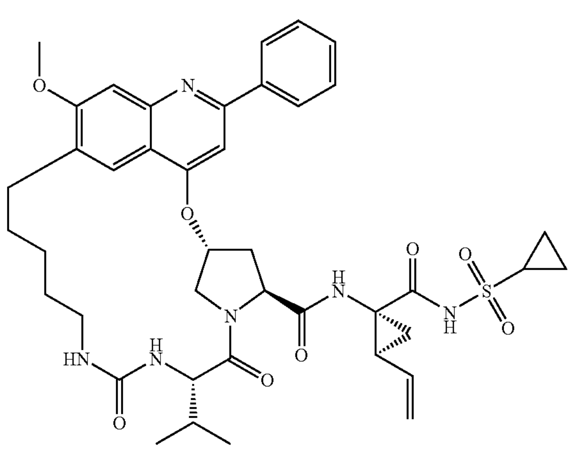 | (2R,4S,7S)-N-((1R,2S)-1-{[(Cyclopropylsulfonyl)amino]carbonyl}-2-vinylcyclopropyl)-7-isopropyl-23-methoxy-6,9-dioxo-20-phenyl-3,4,6,7,8,9,10,11,12,13,14,15-dodecahydro-2H-16,18-ethanediylidene-2,5-methanopyrido[3,4-r][1,5,8,10]oxatriazacyclononadecine-4-carboxamide | 787.3 | See Example 23; for MeO-quinoline, see Example 8, step 3 | A20 |

-continued

| Ex/Cpd | Structure | Name | LRMS M + H)+ | Prepared using the apropriate Linker according to the procedure below | Linker |
|---|---|---|---|---|---|
| 40/ III-43 | 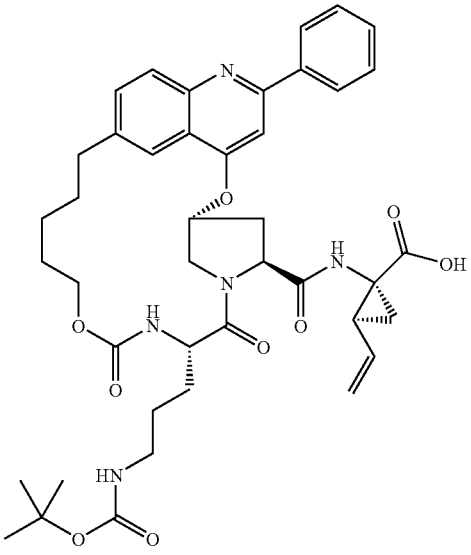 | (1R,2S)-1-{[((2R,4S,7S)-7-{3-[(tert-Butoxycarbonyl)amino]propyl}-6,9-dioxo-20-phenyl-3,4,6,7,8,9,12,13,14,15-decahydro-2H,11H-16,18-ethanediylidene-2,5-methano pyrido[4,3-k][1,10,3,6]dioxadiaza cyclononadecin-4-yl)carbonyl]amino}-2-vinyl cyclopropanecarboxylic acid | 770.4 | See Example 21 | A11 |
| 41/ III-44 | 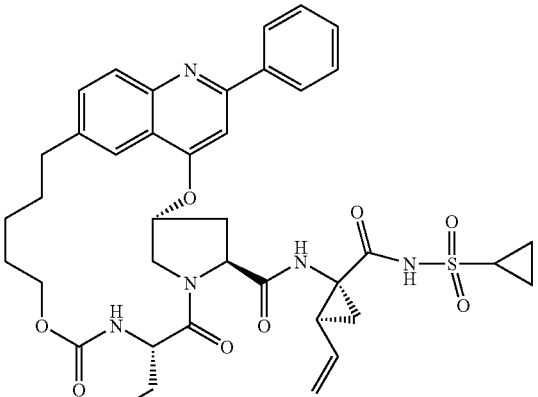 | tert-Butyl 3-((2R,4S,7S)-4-{[((1R,2S)-1-{[(cyclopropyl sulfonyl)amino]carbonyl}-2-vinylcyclopropyl)amino]carbonyl}-6,9-dioxo-20-phenyl-3,4,6,7,8,9,12,13,14,15-decahydro-2H,11H-16,18-ethanediylidene-2,5-methano pyrido[4,3-k][1,10,3,6]dioxadiazacyclononadecin-7-yl)propylcarbamate | 873.4 | See Example 23 | A11 |

-continued

| Ex/Cpd | Name | LRMS M+H)+ | Prepared using the apropriate Linker according to the procedure below | Linker |
|---|---|---|---|---|
| 42/III-45 | (2R,4S,7S)-N-((1R,2S)-1-{[(Cyclopropylsulfonyl)amino]carbonyl}-2-vinyl cyclopropyl)-7-isopropyl-23-methoxy-10-methyl-6,9-dioxo-20-phenyl-3,4,6,7,8,9,10,11,12,13,14,15-dodecahydro-2H-16,18-ethanediylidene-2,5-methano pyrido[3,4-r][1,5,8,10]oxa triazacyclononadecine-4-carboxamide | 801.3 | See Example 23; for MeO-quinoline, see Example 8, step 3 | A18 |
| 43/III-46 | (2R,4S,7S)-N-((1R,2S)-1-{[(Cyclopropylsulfonyl)amino]carbonyl}-2-vinylcyclo propyl)-7-isopropyl-23-methoxy-10-methyl-6,9-dioxo-20-phenyl-3,4,6,7,8,9,10,11,12,13-decahydro-2H-16,18-ethanediylidene-2,5-methanopyrido[3,4-r][1,5,8,10]oxatriazacyclo nonadecine-4-carboxamide | 799.4 | See Example 22; for MeO-quinoline, see Example 8, step 3 | A18 |
| 44/III-47 | (2R,4S,7S)-7-Butyl-N-((1R,2S)-1-{[(cyclopropyl sulfonyl)amino]carbonyl}-2-vinyl cyclopropyl)-6,9-dioxo-20-phenyl-3,4,6,7,8,9,10,11,12,13-decahydro-2H-16,18-ethanediylidene-2,5-methanopyrido[3,4-r][1,5,8,10]oxatriazacyclonona decine-4-carboxamide | 769.5 | See Example 22 | A19 |

-continued

| Ex/Cpd | Structure | Name | LRMS M + H)+ | Prepared using the apropriate Linker according to the procedure below | Linker |
|---|---|---|---|---|---|
| 45/III-48 | 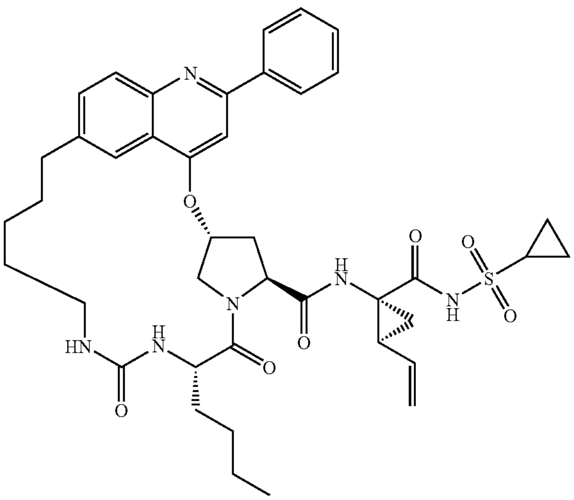 | (2R,4S,7S)-7-Butyl-N-((1R,2S)-1-{[(cyclopropylsulfonyl)amino]carbonyl}-2-vinylcyclopropyl)-6,9-dioxo-20-phenyl-3,4,6,7,8,9,10,11,12,13,14,15-dodecahydro-2H-16,18-ethanediylidene-2,5-methanopyrido[3,4-r][1,5,8,10]oxatriazacyclononadecine-4-carboxamide | 771.5 | See Example 23 | A19 |
| 46/III-49 | 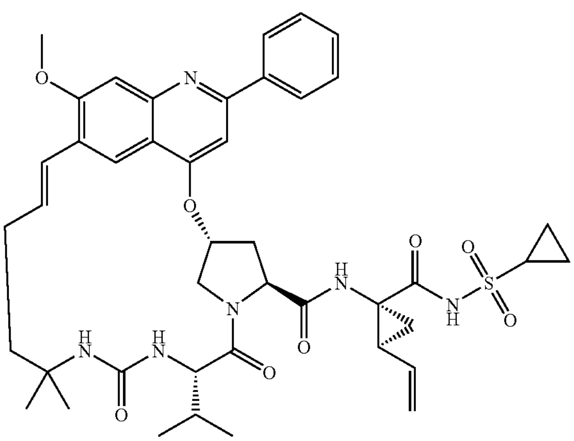 | (2R,4S,7S)-N-((1R,2S)-1-{[(Cyclopropylsulfonyl)amino]carbonyl}-2-vinylcyclopropyl)-7-isopropyl-23-methoxy-11,11-dimethyl-6,9-dioxo-20-phenyl-3,4,6,7,8,9,10,11,12,13-decahydro-2H-16,18-ethanediylidene-2,5-methanopyrido[3,4-r][1,5,8,10]oxatriazacyclononadecine-4-carboxamide | 813.6 | See Example 22; for MeO-quinoline, see Example 8, step 3 | A21 |
| 47/III-50 | 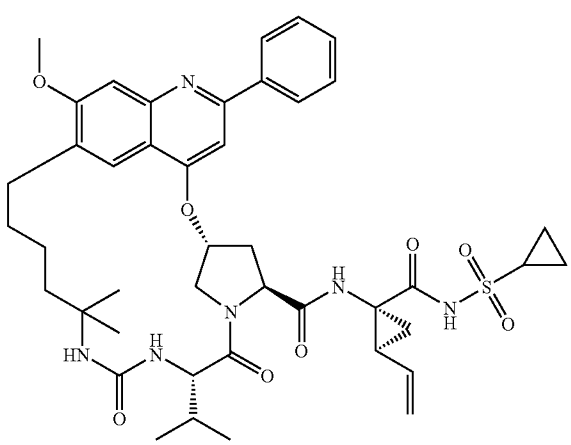 | (2R,4S,7S)-N-((1R,2S)-1-{[(Cyclopropylsulfonyl)amino]carbonyl}-2-vinylcyclopropyl)-7-isopropyl-23-methoxy-11,11-dimethyl-6,9-dioxo-20-phenyl-3,4,6,7,8,9,10,11,12,13,14,15-dodecahydro-2H-16,18-ethanediylidene-2,5-methano pyrido[3,4-r][1,5,8,10]oxatriazacyclononadecine-4-carboxamide | 815.5 | See Example 23; for MeO-quinoline, see Example 8, step 3 | A21 |

-continued

| Ex/Cpd | Structure | Name | LRMS M + H)+ | Prepared using the apropriate Linker according to the procedure below | Linker |
|---|---|---|---|---|---|
| 48/ III-51 | 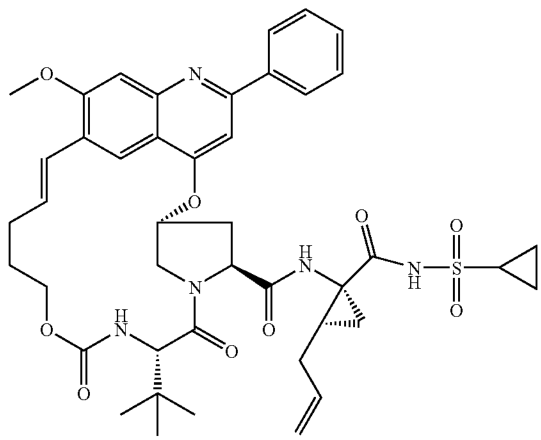 | (2R,4S,7S)-7-tert-Butyl-N-((1R,2S)-1-{[(cyclopropyl sulfonyl)amino]carbonyl}-2-vinylcyclopropyl)-23-methoxy-6,9-dioxo-20-phenyl-3,4,6,7,8,9,12,13-octahydro-2H,11H-16,18-ethanediylidene-2,5-methano pyrido[4,3-k][1,10,3,6]dioxadiazacyclononadecine-4-carboxamide | 800.2 | See Example 22; for MeO-quinoline, see Example 8, step 3 | A10 |
| 49/ III-52 | 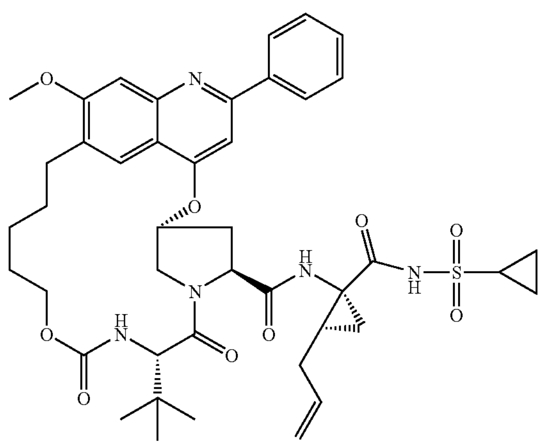 | (2R,4S,7S)-7-tert-Butyl-N-((1R,2S)-1-{[(cyclopropyl sulfonyl)amino]carbonyl}-2-vinylcyclopropyl)-23-methoxy-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecine-4-carboxamide | 802.3 | See Example 23; for MeO-quinoline, see Example 8, step 3 | A10 |
| 50/ III-53 | 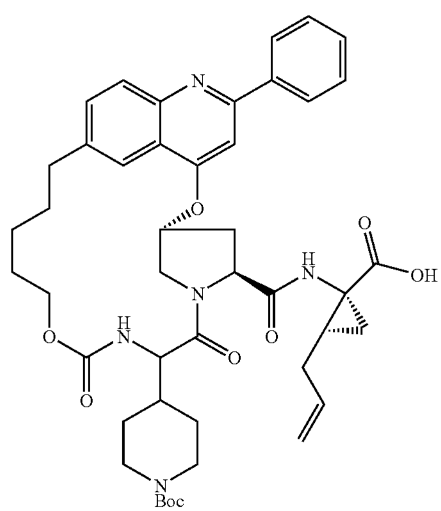 | (1R,2S)-1-[({(2R,4S)-7-[1-(tert-Butoxycarbonyl)piperidin-4-yl]-6,9-dioxo-20-phenyl-3,4,6,7,8,9,11,12,13,14-decahydro-2H,11H-16,18-ethanediylidene-2,5-methanopyrido[4,3-k][1,10,3,6]dioxadiazacyclononadecin-4-yl}carbonyl)amino]-2-vinylcyclopropanecarboxylic acid | 796.2 | See Example 21 | A15 |

EXAMPLE 51

(2R,4S,7S)-7-Cyclohexyl-N-((1R,2S)-1-{[(cyclopropylsulfonyl)amino]carbonyl}-2-vinylcyclopropyl)-23-methoxy-12,12-dimethyl-6,9-dioxo-20-phenyl-3,4,6,7,8,9,12,13-octahydro-2H,11H-16,18-ethanediylidene-2,5-methanopyrido[4,3-k][1,10,3,6]dioxadiazacyclononadecine-4-carboxamide (III-54)

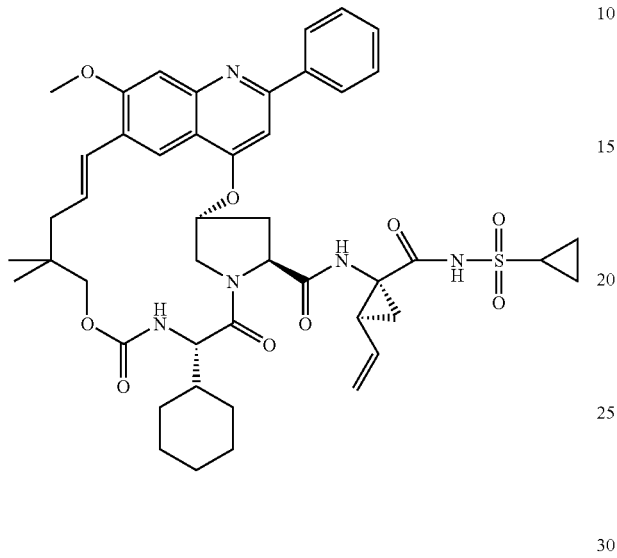

EXAMPLE 51 was prepared using the procedure described for EXAMPLE 22 with the following modifications: 1) Methoxy-quinoline, see EXAMPLE 8, Step 3; 2) Linker A13; and 3) for EXAMPLE 20, Step 6, the olefin metathesis catalyst employed was the Zhan ruthenium metathesis catalyst RC-303 (Zhan catalyst 1B, RC-303, Zannan Pharma Ltd.). $^1$H NMR (CDCl$_3$, 400 MHz, ppm) δ 8.17 (s, 1H); 8.03 (d, J=6.7 Hz, 2H); 7.44 (m, 3H); 7.37 (s, 1H); 6.96 (s, 1H); 6.78 (d, J=16 Hz, 1H); 6.30 (m, 1H); 5.72 (m, 1H); 5.41 (m, 2H); 5.17 (d, J=17.0 Hz, 1H); 5.09 (d, J=11.2 Hz, 1H); 4.41 (m, 1H); 4.38 (m, 1H); 4.23 (m, 1H); 3.99 (s, 3H); 3.34 (d, J=9.8 Hz, 1H); 2.91 (m, 1H); 2.64 (m, 1H); 2.36 (m, 2H); 1.94 (m, 6H); 1.79-1.60 (m, 8H); 1.37 (m, 6H); 1.11 (s, 3H); 1.05 (m, 3H); and 0.88 (s, 3H); 0.86 (m, 2H). LRMS (M+H)$^+$ calcd=854.4. found=854.3.

Zhan ruthenium metathesis catalyst RC-303 (Zhan catalyst 1B RC-303 Zannan Pharma Ltd.)

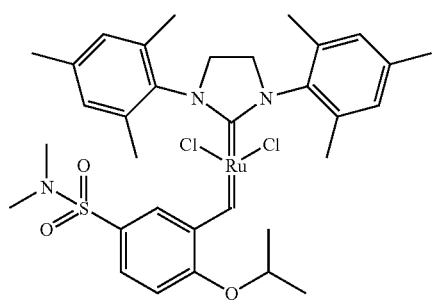

EXAMPLE 52

(1R,2S)-1-({[(2R,4S)-6,9-Dioxo-20-phenyl-7-piperidin-4-yl-3,4,6,7,8,9,12,13,14,15-decahydro-2H,11H-16,18-ethanediylidene-2,5-methanopyrido[4,3-k][1,10,3,6]dioxadiazacyclononadecin-4-yl]carbonyl}amino)-2-vinylcyclopropanecarboxylic acid (III-55)

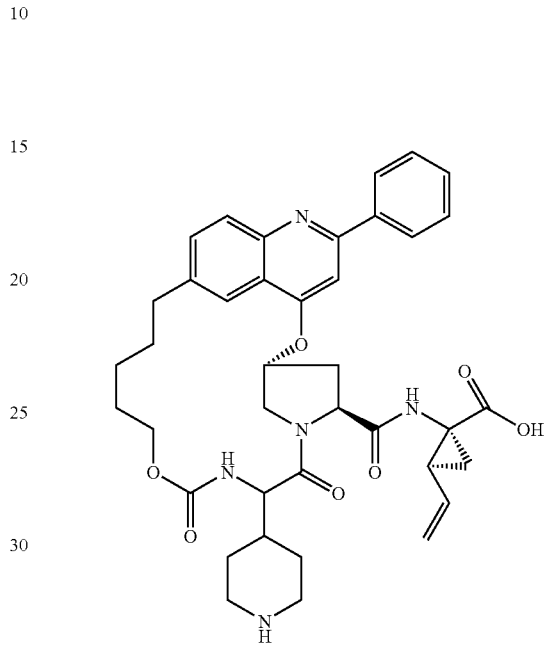

To a solution of (1R,2S)-1-[({(2R,4S)-7-[1-(tert-butoxycarbonyl)piperidin-4-yl]-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecin-4-yl}carbonyl)amino]-2-vinylcyclopropanecarboxylic acid (EXAMPLE 50) (39 mg, 0.05 mmol) in dichloromethane (1 mL) was added trifluoroacetic acid (1 mL) and the reaction mixture stirred at RT for 2 h. The reaction mixture was concentrated and purified by reverse phase HPLC to give (1R,2S)-1-({[(2R,4S)-6,9-dioxo-20-phenyl-7-piperidin-4-yl-3,4,6,7,8,9,12,13,14,15-decahydro-2H,11H-16,18-ethanediylidene-2,5-methanopyrido[4,3-k][1,10,3,6]dioxadiazacyclononadecin-4-yl]carbonyl}amino)-2-vinylcyclopropanecarboxylic acid (EXAMPLE 52) (27 mg, 68% yield). $^1$H NMR (DMSO-d$_6$, 500 MHz, ppm) δ 8.90 (s, 1H), 8.48 (d, J=11.7 Hz, 1H), 8.24 (d, J=7.1 Hz, 1H), 7.98 (m, 1H), 7.70 (m, 2H), 7.59 (m, 2H), 7.52 (d, J=9.5 Hz, 1H), 5.75 (m, 1H), 5.59 (m, 1H), 5.31 (d, J=19.0 Hz, 1H), 5.13 (d, J=12.0 Hz, 1H), 4.94 (m, 1H), 4.42 (m, 1H), 4.3 (d, J=13.7 Hz, 1H), 3.94 (t, 1H, J=9.27 Hz), 3.25 (m, 2H), 2.89-2.73 (m, 5H), 2.34 (m, 1H), 2.21 (q, 1H), 1.94 (m, 1H), 1.79 (m, 2H), 1.65 (m, 3H), 1.53 (m, 1H), and 1.33-1.22 (m, 4H). LRMS (M+H)$^+$ calcd=696.3. found 696.2.

EXAMPLE 53

(2R,4S,7S)-7-(3-Aminopropyl)-N-((1R,2S)-1-{[(cyclopropylsulfonyl)amino]carbonyl}-2-vinylcyclopropyl)-6,9-dioxo-20-phenyl-3,4,6,7,8,9,12,13,14,15-decahydro-2H,11H-16,18-ethanediylidene-2,5-methanopyrido[4,3-k][1,10,3,6]dioxadiazacyclononadecine-4-carboxamide (III-56)

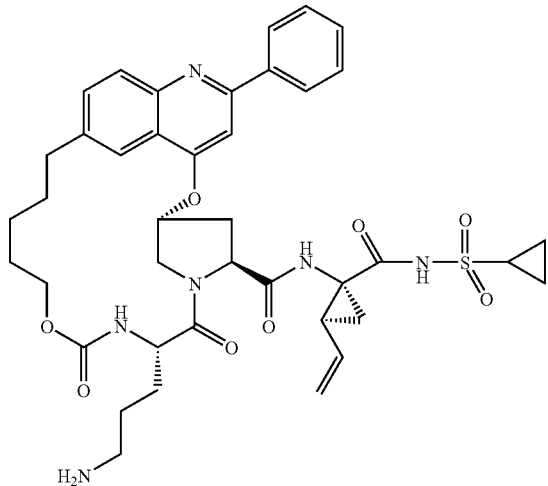

EXAMPLE 53 was prepared using the procedure described for EXAMPLE 52 by using EXAMPLE 41 as starting material instead of EXAMPLE 51. $^1$H NMR (CD$_3$OD, 500 MHz, ppm) δ 8.18 (s, 1H), 8.14 (d, J=8.5 Hz, 1H), 8.08 (m, 2H), 7.98 (dd, J=8.8 and 1.7 Hz, 1H), 7.82 (s, 1H), 7.79-7.71 (m, 3H), 6.05 (m, 1H), 5.73 (m, 1H), 5.31 (dd, J=17.2 and 1.3 Hz, 1H), 5.14 (dd, J=10.2 and 1.5 Hz, 1H), 4.93 (d, J=11.7 Hz, 1H), 4.61 (dd, J=10.5 and 6.8 Hz, 1H), 4.45 (dd, J=9.6 and 5.2 Hz, 1H), 4.3 (m, 1H), 4.13 (dd, J=12.1 and 3.1 Hz, 1H), 3.77 (m, 1H), 3.02 (m, 3H), 2.91 (m, 1H), 2.83 (m, 1H), 2.71 (m, 1H), 2.44 (m, 1H), 2.24 (m, 1H), 2.04 (m, 1H), 1.93-1.57 (m, 8H), 1.41-1.25 (m, 5H), 1.15 (m, 3H), and 1.05 (s, 1H). LRMS (M+H)$^+$ calcd=773.3. found 774.

EXAMPLE 54

(2R,4S,7S)-7-Butyl-N-((1R,2S)-1-{[(cyclopropylsulfonyl)amino]carbonyl}-2-vinylcyclopropyl)-6,9-dioxo-20-phenyl-3,4,6,7,8,9,12,13-octahydro-2H,11H-16,18-etheno-2,5-methanopyrido[4,3-k][1,10,3,6]dioxadiazacyclononadecine-4-carboxamide (III-57)

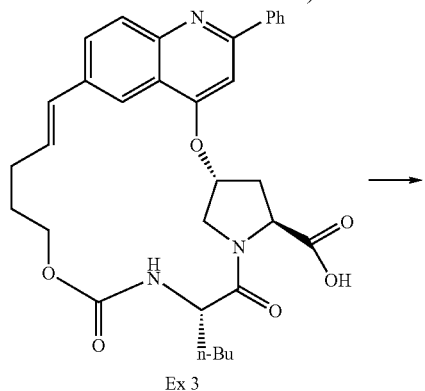

Ex 3

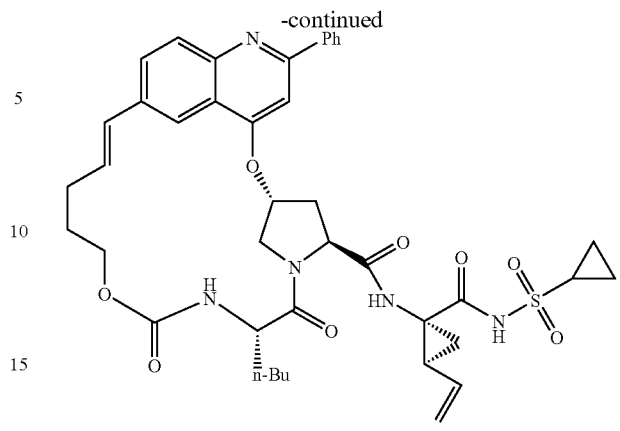

Ex 54

To a solution of (2R,4S,7S)-7-butyl-6,9-dioxo-20-phenyl-3,4,6,7,8,9,12,13-octahydro-2H,11H-16,18-etheno-2,5-methanopyrido[4,3-k][1,10,3,6]dioxadiazacyclononadecine-4-carboxylic acid EXAMPLE 3 (200 mg, 0.36 mmol) in DMF (3 mL) was added (1R,2S)-1-{[(cyclopropylsulfonyl)amino]carbonyl}-2-vinylcyclopropanaminium chloride (Wang et al., U.S. Pat. No. 6,995,174) (195 mg, 0.73 mmol), TBTU (235 mg, 0.73 mmol) and DIPEA (0.20 mL, 1.13 mmol) and the reaction mixture was stirred at RT for 18 h. The reaction mixture was partitioned between EtOAc and saturated aqueous NaHCO$_3$. The layers were separated and the organic was washed with water and brine, dried over Na$_2$SO$_4$, filtered and concentrated. The crude product was purified on silica gel (gradient elution, 50% to 100% EtOAc in hexane) to yield (2R,4S,7S)-7-butyl-N-((1R,2S)-1-{[(cyclopropylsulfonyl)amino]carbonyl}-2-vinylcyclopropyl)-6,9-dioxo-20-phenyl-3,4,6,7,8,9,12,13-octahydro-2H,1H-16,18-etheno-2,5-methanopyrido[4,3-k][1,10,3,6]dioxadiazacyclononadecine-4-carboxamide EXAMPLE 54 (120 mg, 45%) as a white foam. $^1$HNMR (CDCl$_3$, 400 MHz, ppm) δ 8.14 (d, J=1.6 Hz, 1H); 8.04 (m, 2H); 7.97 (d, J=8.6 Hz, 1H); 7.43 (m, 6H); 7.07 (s, 1H); 6.46 (d, J=16.0 Hz, 1H); 6.36 (m, 1H); 5.84 (d, J=8.1 Hz, 1H); 5.69 (m, 1H); 5.27 (s, 1H); 5.17 (d, J=16 Hz, 1H); 5.07 (dd, J=11.5, 1.4 Hz, 1 H); 4.65 (d, J=11.5 Hz, 1H); 4.49 (m, 2H); 4.41 (m, 1H); 3.95 (m, 2H); 2.83 (m, 1H), 2.68 (m, 1H); 2.41-2.30 (m, 4H); 2.09 (m, 2H); 1.97 (m, 1H); 1.79 (m, 1H); 1.84 (m, 1H); 1.34 (m, 6H); 1.13 (m, 1H); 0.94 (m, 2H); and 0.83 (m, 3H). LRMS (M+H)$^+$ calcd=770.3. found 770.3.

SCHEME 6

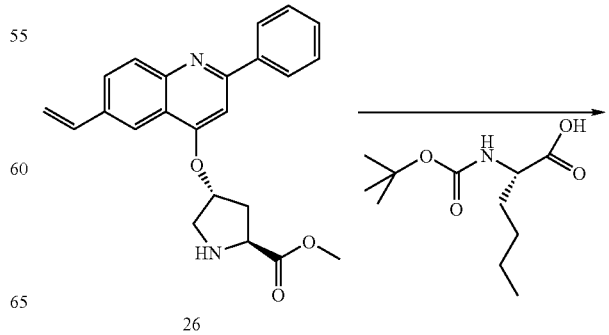

26

EXAMPLE 55

(1R,2S)-1-({[(2R,4S,7S)-7-Butyl-9,9-dioxido-6-oxo-19-phenyl-3,4,7,8,11,12,13,14-octahydro-2H,6H,10H-15,17-ethanediylidene-2,5-methanopyrido[3,4-q][1,9,5,8]oxathiadiazacyclooctadecin-4-yl]carbonyl}amino)-2-vinylcyclopropanecarboxylic acid (III-58)

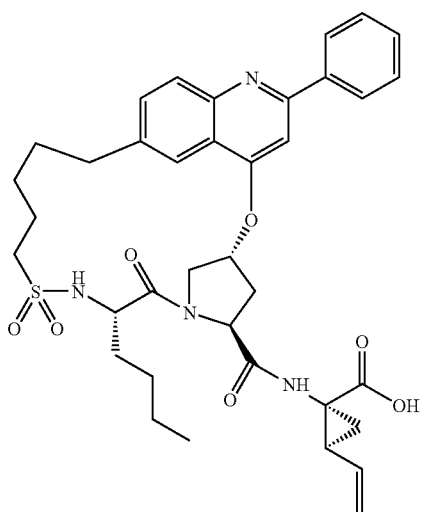

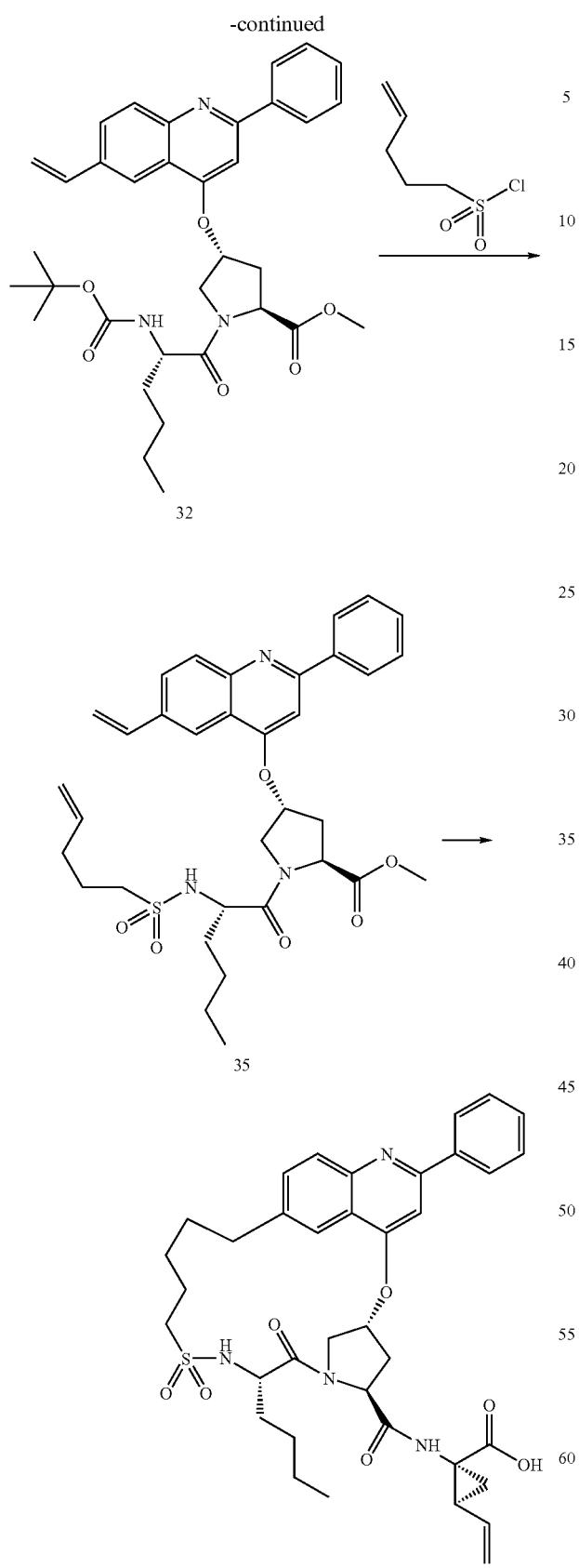

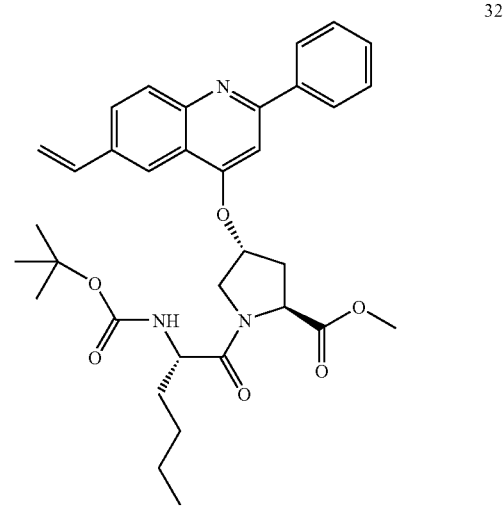

Step 1: Methyl N-(tert-butoxycarbonyl)-L-norleucyl-(4R)-4-[(2-phenyl-6-vinylquinolin-4-yl)oxy]-L-prolinate (32)

Compound 32 was prepared by coupling 26 and Boc-L-norleucine according to the procedure described in EXAMPLE 20, Step 5. LRMS (M+H)⁺=588.

Step 2: Methyl N-(pent-4-enylsulfonyl)-L-norleucyl-(4R)-4-[(2-phenyl-6-vinylquinolin-4-yl)oxy]-L-prolinate (33)

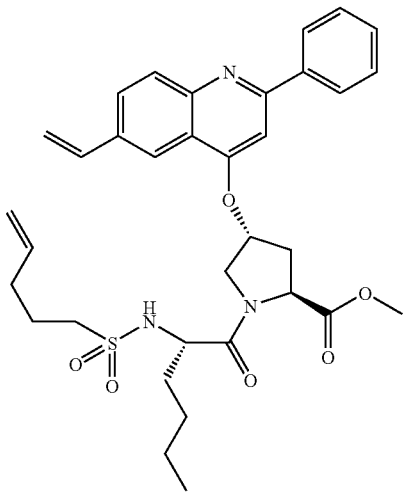

Compound 32 (115 mg, 0.196 mmol) was dissolved in EtOAc (5 mL) cooled to 0° C. and treated with anhydrous HCl gas for 10 min. The reaction mixture was then concentrated to give a solid. The solid was dissolved in DMF (2 mL) and DIPEA (0.1 mL, 0.57 mmol) was added. The reaction was cooled to 10° C. and 4-pentenesulfonyl chloride (35 mg, 0.20 mmol) (Culshaw, P. N.; Walton, J. C., *J. Chem. Soc., Perkin Trans.* 2 (1991), 8, p 1201) was then added. The mixture was stirred at RT for 30 min, quenched with aqueous NaHCO$_3$ and extracted with EtOAc. The EtOAc extract was dried over NaSO$_4$, filtered, concentrated to an oil and chromatographed on silica to give 33 (94 mg, 78% yield) as a foam. LRMS (M+1)$^+$=620.

Steps 3-7: (1R,2S)-1-({[(2R,4S,7S)-7-Butyl-9,9-dioxido-6-oxo-[9-phenyl-3,4,7,8,11,12,13,14-octahydro-2H,6H,10H-15,17-ethanediylidene-2,5-methanopyrido[3,4-q][1,9,5,8]oxathiadiazacyclooctadecin-4-yl]carbonyl}amino)-2-vinylcyclopropanecarboxylic acid (EXAMPLE 55)

EXAMPLE 55 was prepared from 33 according to the procedures described in EXAMPLE 20, Step 6 followed by EXAMPLE 21, Steps 1-4. $^1$H NMR (500 MHz, CD$_3$OD, ppm) δ 8.71 (s, 1H), 8.03-8.17 (m, 4H), 7.96 (m, 1H), 7.79 (s, 1H), 7.70-7.77 (m, 4H), 5.83 (br s, 1H), 5.83 (m, 1H), 5.27 (d, 1H, J=15.6 Hz), 5.10 (dd, 1H, J=1.7 and 10.3 Hz), 4.72 (t, 1H, J=7.6 Hz), 4.42 (br d, 1H, J=11.5 Hz), 4.24 (t, 1H, J=6.1 Hz), 4.05 (dd, 1H, J=2.5 and 12.5 Hz), 2.7-3.0 (m, 5H), 2.55 (m, 1H), 2.19 (q, 1H, J=8.7 Hz), 1.2-2.0 (m, 15H), and 0.95 (t, 3H, J=7.3 Hz). LRMS (M+H)$^+$ calcd=689.3. found 689.3.

EXAMPLE 56

(2R,4S,7S)-7-Butyl-N-((1R,2S)-1-{[(cyclopropylsulfonyl)amino]carbonyl}-2-vinylcyclopropyl)-6-oxo-19-phenyl-3,4,7,8,11,12,13,14-octahydro-2H,6H,10H-15,17-ethanediylidene-2,5-methanopyrido[3,4-q][1,9,5,8]oxathiadiazacyclooctadecine-4-carboxamide 9,9-dioxide (III-59)

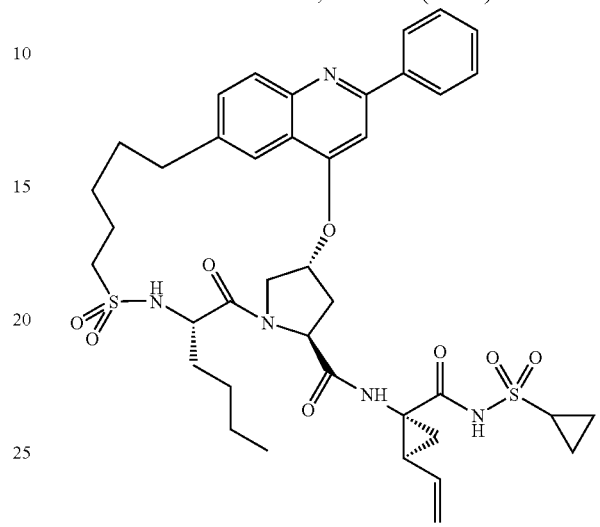

EXAMPLE 56 was prepared from EXAMPLE 55 using the procedure described for EXAMPLE 22. $^1$H NMR (500 MHz, CD$_3$OD, ppm) δ 8.15 (m, 2H), 8.09 (m, 2H), 7.97 (dd, 1H, J=1.9 and 9.2 Hz), 7.80 (s, 1H), 7.70-7.78 (m, 4H), 5.88 (br s, 1H), 5.75 (m, 1H), 5.31 (dd, 1H, J=1.5 and 18.2 Hz), 5.14 (dd, 1H, J=1.5 and 12.2 Hz), 4.64 (m, 1H), 4.46 (br d, 1H, J=13.0 Hz), 4.22 (t, 1H, J=7.8 Hz), 4.08 (dd, 1H, J=2.5 and 13.0 Hz), 2.98 (m, 4H), 2.80 (m, 2H), 2.46 (m, 1H), 2.24 (q, 1H, J=10.5 Hz), 1.0-2.0 (m, 20H), and 0.92 (t, 3H, J=7.3 Hz). LRMS (M+H)$^+$ calcd=792.3. found 792.4.

EXAMPLE 57

(1R,2S)-1-({[(2R,4S,7S)-7-Butyl-9,9-dioxido-6-oxo-20-phenyl-3,4,7,10,11,12,13,14,15-decahydro-2H,6H-16,18-ethanediylidene-2,5-methanopyrido[3,4-r][1,9,5,8]oxathiadiazacyclononadecin-4-yl]carbonyl}amino)-2-vinylcyclopropanecarboxylic acid (III-60)

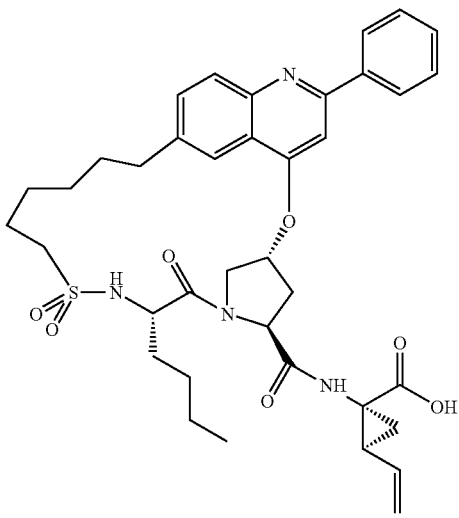

EXAMPLE 57 was prepared according to the procedure described for EXAMPLE 55 using 5-hexenesulfonyl chloride (Culshaw, P. N.; Walton, J. C., *J. Chem. Soc., Perkin Trans.* 2 (1991), 8, p 1201) instead of 4-pentenesulfonyl chloride. ¹H NMR (500 MHz, CD₃OD, ppm) δ 8.77 (s, 1H), 8.19 (brs, 1H), 8.17 (d, 1H, J=8.6 Hz), 8.09 (d, 1H, J=6.8 Hz), 7.99 (dd, 1H, J=1.7 and 8.8 Hz), 7.82 (s, 1H), 7.70-7.78 (m, 4H), 5.98 (brs, 1H), 5.84 (m, 1H), 5.28 (dd, 1H, J=1.2 and 17.1 Hz), 5.14 (dd, 1H, J=1.4 and 10.5 Hz), 4.75 (m, 1H), 4.38 (brd, 1H, J=11.2 Hz), 4.19 (m, 1H), 4.07 (dd, 1H, J=2.7 and 12.3 Hz), 3.04 (m, 1H), 2.80-2.95 (m, 2H), 2.60 (m, 3H), 2.21 (q, 1H, J=8.8 Hz), 1.0-1.9 (m, 18H), and 0.92 (t, 3H, J=7.2 Hz). LRMS (M+H)⁺ calcd=703.3. found 703.5.

EXAMPLE 58

(2R,4S,7S)-7-Butyl-N-((1R,2S)-1-{[(cyclopropylsulfonyl)amino]carbonyl}-2-vinylcyclopropyl)-6-oxo-20-phenyl-3,4,7,8,10,11,12,13,14,15-decahydro-2H,6H-16,18-ethanediylidene-2,5-methanopyrido[3,4-r][1,9,5,8]oxathiadiazacyclononadecine-4-carboxamide 9,9-dioxide (III-61)

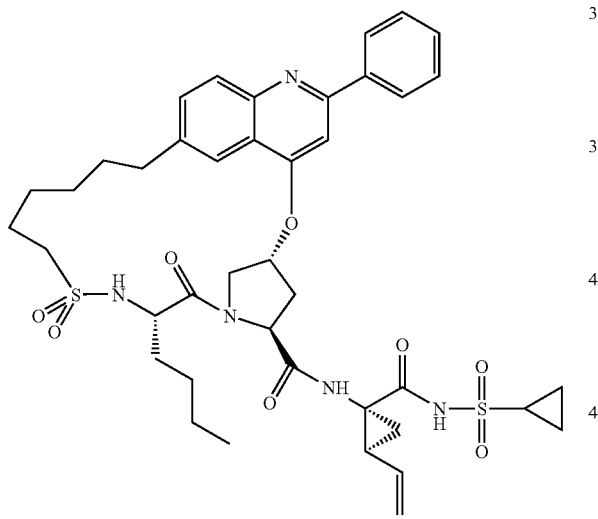

EXAMPLE 58 was prepared from EXAMPLE 57 using the procedure described for EXAMPLE 22. ¹H NMR (500 MHz, CD₃OD, ppm) δ 8.16 (s, 1H), 8.15 (d, 1H, J=8.8 Hz), 8.09 (dd, 2H, J=1.2 and 7.8 Hz), 7.96 (dd, 1H, J=1.7 and 8.8 Hz), 7.80 (s, 1H), 7.68-7.76 (m, 3H), 6.00 (brs, 1H), 5.78 (m, 1H), 5.35 (dd, 1H, J=1.0 and 17.1 Hz), 5.15 (dd, 1H, J=1.4 and 10.2 Hz), 4.78 (m, 1H), 4.35 (brd, 1H, J=12.7 Hz), 4.18 (m, 1H), 4.08 (dd, 1H, J=2.7 and 12.5 Hz), 3.08 (m, 1H), 2.94 (m, 2H), 2.78 (m, 1H), 2.62 (m, 2H), 2.48 (m, 1H), 2.27 (q, 1H, J=8.8 Hz), 1.92 (m, 1H), 1.0-1.8 (m, 21H), and 0.93 (t, 3H, J=7.3 Hz). LRMS (M+H)⁺=806.3. found 806.5.

SCHEME 7

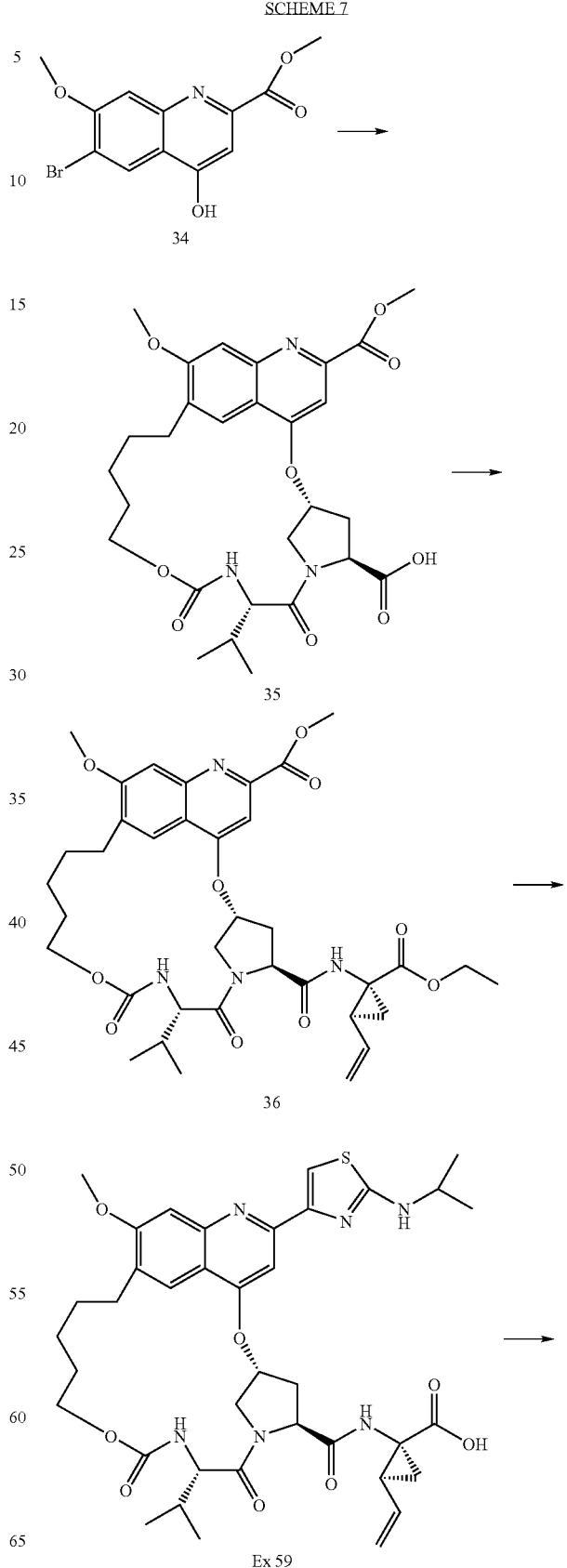

-continued

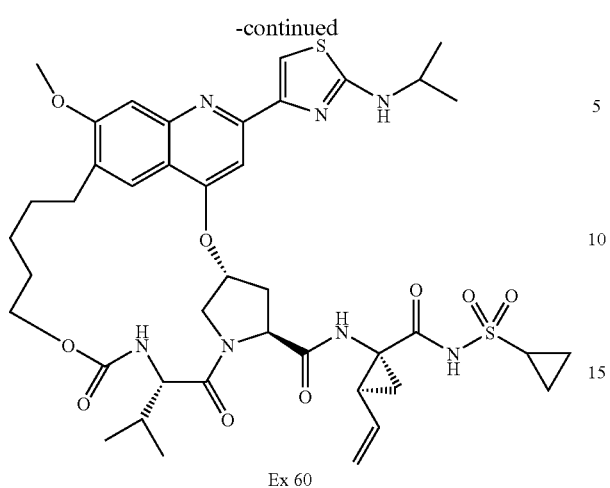

Ex 60

EXAMPLE 59

(1R,2S)-1-[({(2R,4S,7S)-7-Isopropyl-20-[2-(isopropylamino)-1,3-thiazol-4-yl]-23-methoxy-6,9-dioxo-3,4,6,7,8,9,12,13,14,15-decahydro-2H,11H-16,18-ethanediylidene-2,5-methanopyrido[4,3-k][1,10,3,6]dioxadiazacyclononadecin-4-yl}carbonyl)amino]-2-vinylcyclopropanecarboxylic acid (III-62)

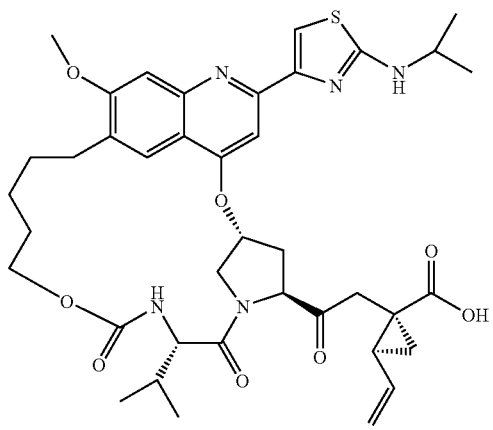

Step 1: Methyl 6-bromo-4-hydroxy-7-methoxyquinoline-2-carboxylate

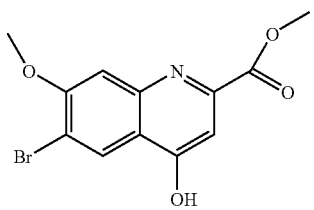

34

3-Methoxy-4-bromoaniline (10.0 g, 0.0494 mol) and dimethylacetylene dicarboxylate (7.46 g, 0.0525 mol) were combined in MeOH (71 mL) and DOWTHERM (140 mL) and refluxed under nitrogen for 18 hrs. The reaction was cooled and concentrated to give an oily residue and additional DOWTHERM (20 mL) was added. This solution was added dropwise via syringe to DOWTHERM (120 mL) at 250° C. and allowed to stir at 250° C. for an additional 15 min (precipitate observed). The reaction mixture was cooled to RT, solids filtered and washed with hexanes to give 14.4 g solid. The solid was resuspended in dichloromethane (200 mL) and stirred for 30 min. The solid was filtered to give to give 34 (13.8 g, 90% yield). LRMS (M+H)$^+$=312.

Step 2-7: (2R,4S,7S)-7-Isopropyl-23-methoxy-20-(methoxycarbonyl)-6,9-dioxo-3,4,6,7,8,9,12,13,14,15-decahydro-2H,11H-16,18-ethanediylidene-2,5-methanopyrido[4,3-k][1,10,3,6]dioxadiazacyclononadecine-4-carboxylic acid

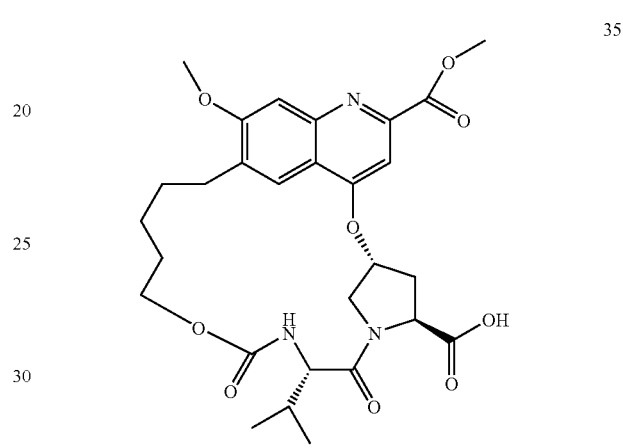

35

Compound 35 was prepared from compound 34 and linker A9 according to the procedures described in EXAMPLE 20, Steps 2-7. LRMS (M+H)$^+$=558.

Step 8: Methyl (2R,4S,7S)-4-({[(1R,2S)-1-(ethoxycarbonyl)-2-vinylcyclopropyl]amino}carbonyl)-7-isopropyl-23-methoxy-6,9-dioxo-3,4,6,7,8,9,12,13,14,15-decahydro-2H,11H-16,18-ethanediylidene-2,5-methanopyrido[4,3-k][1,10,3,6]dioxadiazacyclononadecine-20-carboxylate

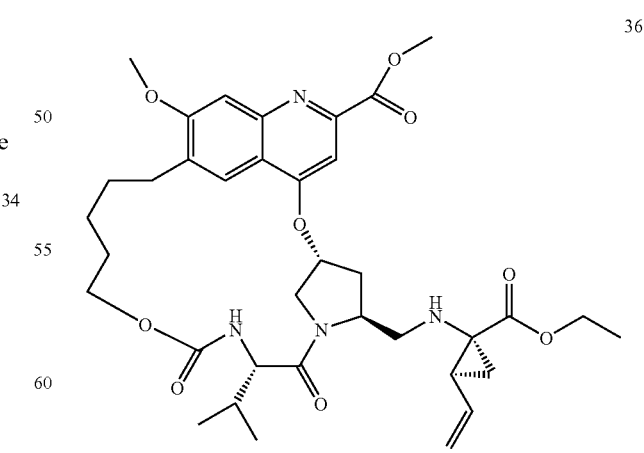

36

Compound 36 was prepared from compound 35 according to the procedures described in EXAMPLE 20, Step 8. LRMS (M+H)$^+$=695.

127

Step 9: (1R,2S)-1-[({(2R,4S,7S)-7-Isopropyl-20-[2-(isopropylamino)-1,3-thiazol-4-yl]-23-methoxy-6,9-dioxo-3,4,6,7,8,9,12,13,14,15-decahydro-2H,11H-16,18-ethanediylidene-2,5-methanopyrido[4,3-k][1,10,3,6]dioxadiazacyclononadecin-4-yl}carbonyl)amino]-2-vinylcyclopropanecarboxylic acid (EXAMPLE 59)

Compound 36 (200 mg, 0.288 mmol) was dissolved in THF (1.9 mL), MeOH (1.0 mL) and water (1.0 mL), treated with 1N NaOH (0.288 mL, 0.288 mmol) and stirred at RT for 3 h. The reaction was concentrated in vacuo to give a foam. The foam was dissolved in THF (3.0 mL) and $Et_3N$ was added (60 uL, 0.432 mmol). The reaction mixture was cooled to 0° C. and treated with isobutylchloroformate (57 uL, 0.432 mmol) and the mixture was stirred at 0° C. for 1.5 hrs. A solution of diazomethane in diethyl ether (4.3 mmol) prepared from 1-methyl-3-nitro-1-nitrosoquanidine (MNNG, 0.635 g, Aldrichimica Acta (1983) 16, 3) was then added and mixture stirred at 0° C. for 30 min and at RT for 30 min. The resulting solution was concentrated to give a solid which was dissolved in EtOAc, washed with 10% aq. $NaHCO_3$, water and brine. The organic extract was dried over magnesium sulfate, filtered and concentrated to give a yellow foam.

The foam was dissolved in THF (4 mL) cooled to 0° C. and 48% aq. hydrobromic acid (0.21 mL) was added dropwise. The reaction mixture was stirred at 0° C. for 1 h, diluted with EtOAc and washed with 10% aq. $NaHCO_3$, water and brine then dried over magnesium sulfate, filtered and concentrated to give a foam.

The foam was dissolved in isopropanol (9 mL) and isopropylthiourea (68 mg) was added. The mixture was then placed in a 70° C. oil bath and stirred for 30 minutes. The reaction mixture was concentrated in vacuo, dissolved in EtOAc and washed with 10% aq. $NaHCO_3$, water and brine. The organic extract was dried over magnesium sulfate, filtered and concentrated to give a yellow foam (250 mg). The foam was chromatographed on silica using EtOAc to 10% MeOH/EtOAc/1% $Et_3N$ to give a foam. The foam (180 mg, 0.232 mmol) was dissolved in THF/EtOH/water (6 mL, 2/1/1), treated with LiOH (43 mg) and stirred for 2 h. Dilution with 3 N HCl (0.6 mL) and concentrated to a foam, followed by purification by reverse phase HPLC gave EXAMPLE 59. $^1H$ NMR (500 MHz, $CD_3OD$, ppm) δ 8.69 (s, 1H), 8.10 (s, 1H), 8.02 (s, 1H), 7.78 (s, 1H), 7.71 (s, 1H), 5.88 (m, 1H), 5.62 (m, 1H), 5.26 (dd, 1H, J=1.7 and 17.1 Hz), 5.09 (dd, 1H, J=2.0 and 10.5 Hz), 4.90 (d, 1H, J=12.2 Hz), 4.62 (m, 1H), 4.30 (m, 1H), 4.17 (m, 1H), 4.10 (m, 2H), 4.07 (s, 3H), 3.79 (m, 1H), 3.09 (m, 1H), 2.68 (m, 1H), 2.55 (m, 2H), 2.20 (q, 1H, J=8.8 Hz), 2.02 (m, 1H), 1.75 (m, 4H), 1.68 (m, 1H), 1.59 (m, 1H), 1.42 (m, 1H), 1.33 (d, 6H, J=6.6 Hz), 1.30 (m, 2H), and 1.05 (t, 6H, J=7.1 Hz). LRMS $(M+H)^+$ calcd=749.3. found 749.6.

128

EXAMPLE 60

(2R,4S,7S)—N-((1R,2S)-1-{[(Cyclopropylsulfonyl)amino]carbonyl}-2-vinylcyclopropyl)-7-isopropyl-20-[2-(isopropylamino)-1,3-thiazol-4-yl]-23-methoxy-6,9-dioxo-3,4,6,7,8,9,12,13,14,15-decahydro-2H,11H-16,18-ethanediylidene-2,5-methanopyrido[4,3-k][1,10,3,6]dioxadiazacyclononadecine-4-carboxamide (III-63)

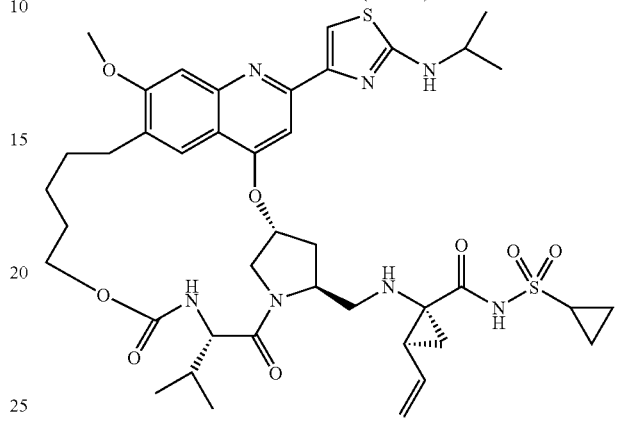

EXAMPLE 60 was prepared from EXAMPLE 59 according to the procedure described for EXAMPLE 22. $^1H$ NMR (500 MHz, $CD_3OD$, ppm) δ 9.35 (s, 1H), 8.08 (s, 1H), 8.00 (s, 1H), 7.81 (s, 1H), 7.73 (s, 1H), 5.95 (m, 1H), 5.75 (m, 1H), 5.28 (dd, 1H, J=1.3 and 17.1 Hz), 5.12 (dd, 1H, J=1.4 and 10.5 Hz), 4.80 (m, 1H), 4.55 (m, 1H), 4.32 (m, 1H), 4.18 (m, 1H), 4.11 (m, 1H), 4.08 (s, 3H), 4.02 (d, 1H, J=10.3 Hz), 3.75 (m, 1H), 3.12 (m, 1H), 2.97 (m, 1H), 2.60 (m, 2H), 2.42 (m, 1H), 2.20 (q, 1H, J=8.8 Hz), 2.12 (m, 1H), 1.89 (m, 1H), 1.75 (m, 3H), 1.55 (m, 1H), 1.39 (m, 1H), 1.33 (d, 6H, J=6.4 Hz), 1.25 (m, 4H), 1.10 (m, 2H), and 1.01 (m, 6H). LRMS $(M+H)^+$ calcd=852.3. found 852.7.

EXAMPLE 61

Methyl (2R,4S,7S)-4-{[((1R,2S)-1-{[(cyclopropylsulfonyl)amino]carbonyl}-2-vinylcyclopropyl)amino]carbonyl}-7-isopropyl-23-methoxy-6,9-dioxo-3,4,6,7,8,9,12,13,14,15-decahydro-2H,11H-16,18-ethanediylidene-2,5-methanopyrido[4,3-k][1,10,3,6]dioxadiazacyclononadecine-20-carboxylate (III-64)

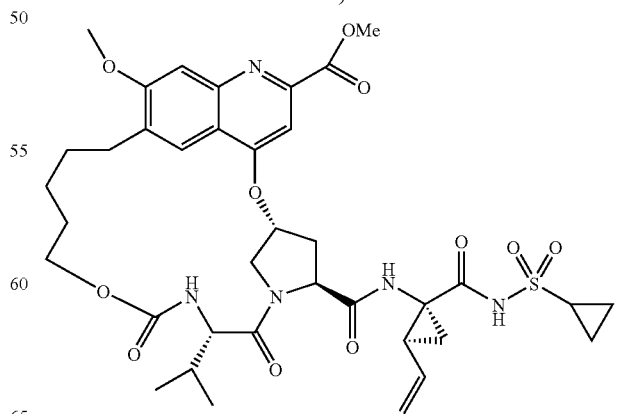

EXAMPLE 61 was prepared from compound 35 using the procedure described in EXAMPLE 54. $^1H$ NMR (500 MHz, CD$_3$OD, ppm) δ 7.91 (s, 1H), 7.61 (s, 1H), 7.45 (s, 1H), 7.31 (brd, 1H, J=8.5 Hz), 5.75 (m, 1H), 5.68 (brs, 1H), 5.26 (d, 1H, J=17.6 Hz), 5.10 (d, 1H, J=11.5 Hz), 4.72 (d, 1H, J=11.6 Hz), 4.50 (m, 1H), 4.39 (m, 1H), 4.08 (m, 1H), 4.03 (s, 3H), 3.99 (s, 3H), 3.77 (m, 1H), 3.10 (m, 1H), 2.98 (m, 1H), 2.54 (m, 2H), 2.32 (m, 1H), 2.18 (m, 1H), 2.15 (s, 3H), 1.88 (m, 1H), 1.76 (m, 3H), 1.56 (m, 1H), 1.38 (m, 1H), 1.08-1.35 (m, 7H), and 1.01 (m, 6H). LRMS (M+H)$^+$ calcd=770.3. found 770.6.

EXAMPLE 62

(2R,4S,7S)-4-{[((1R,2S)-1-{[(Cyclopropylsulfonyl)amino]carbonyl}-2-vinylcyclopropyl)amino]carbonyl}-7-isopropyl-23-methoxy-6,9-dioxo-3,4,6,7,8,9,12,13,14,15-decahydro-2H,11H-16,18-ethanediylidene-2,5-methanopyrido[4,3-k][1,10,3,6]dioxadiazacyclononadecine-20-carboxylic acid (III-65)

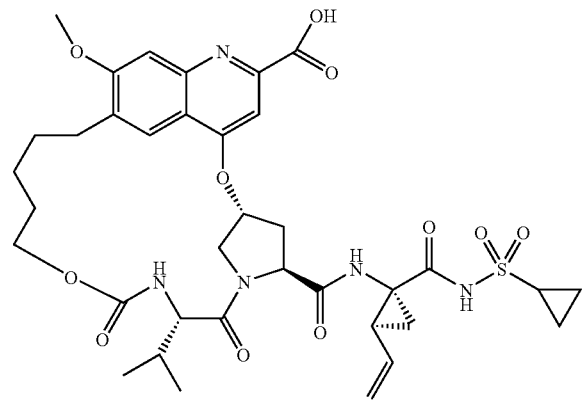

EXAMPLE 61 (25 mg, 0.033 mmol) was dissolved in THF (2 mL) and MeOH (1 mL), treated with 1N sodium hydroxide (0.065 mL) and stirred for 2 h. The reaction mixture was neutralized with 1 N HCl (0.065 mL) and concentrated. Purification by reverse phase HPLC gave EXAMPLE 62 (17 mg). $^1$H NMR (500 MHz, CD$_3$OD, ppm) δ 9.31 (s, 1H), 8.08 (s, 1H), 7.88 (s, 1H), 7.65 (s, 1H), 5.94 (m, 1H), 5.75 (m, 1H), 5.28 (dd, 1H, J=1.2 and 17.0 Hz), 5.12 (dd, 1H, J=1.7 and 10.3 Hz), 4.80 (m, 1H), 4.54 (m, 1H), 4.30 (m, 1H), 4.11 (dd, 1H, J=3.2 and 12.2 Hz), 4.08 (s, 3H), 4.02 (d, 1H, J=10.2 Hz), 3.75 (m, 1H), 3.15 (m, 1H), 2.96 (m, 1H), 2.62 (m, 2H), 2.44 (m, 1H), 2.20 (m, 1H), 2.12 (m, 1H), 1.88 (m, 1H), 1.76 (m, 3H), 1.58 (m, 1H), 1.40 (m, 1H), 1.28 (m, 3H), 1.21 (m, 1H), 1.10 (m, 2H), and 1.05 (m, 6H). LRMS (M+H)$^+$ calcd=756.3. found 756.6.

What is claimed is:

1. A compound of formula III:

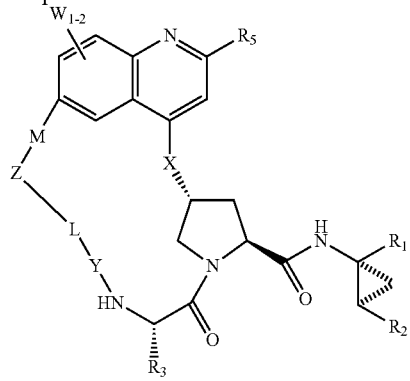

or a pharmaceutically acceptable salt thereof, wherein:

$R_1$ is selected from the group consisting of $CO_2R_{10}$ and $CONHSO_2R_6$;

$R_2$ is selected from the group consisting of $C_1$-$C_4$ alkyl and $C_2$-$C_4$ alkenyl;

$R_3$ is selected from the group consisting of $C_1$-$C_8$ alkyl and $C_3$-$C_8$ cycloalkyl wherein each alkyl or cycloalkyl is optionally substituted with 1 to 3 substituents selected from the group consisting of halo, $OR_{10}$, $SR_{10}$, $N(R_{10})_2$, $C_1$-$C_6$ alkyl, $C_1$-$C_6$ haloalkyl, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

$R_4$ is selected from the group consisting of H, $C_1$-$C_8$ alkyl, $C_3$-$C_8$ cycloalkyl($C_1$-$C_8$)alkyl, and aryl($C_1$-$C_8$)alkyl; wherein aryl is phenyl or naphthyl and said alkyl, cycloalkyl, or aryl is optionally substituted with 1 to 3 substituents selected from the group consisting of halo, $OR_{10}$, $SR_{10}$, $N(R_{10})_2$, $C_1$-$C_6$ alkyl, $C_1$-$C_6$ haloalkyl, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

$R_5$ is selected from the group consisting of $CO_2R_4$, aryl, and heteroaryl, wherein said aryl or heteroaryl is optionally substituted with 1 to 4 substituents selected from the group consisting of halo, $OR_{10}$, $SR_{10}$, $N(R_7)_2$, $C_1$-$C_6$ alkyl, $C_1$-$C_6$ haloalkyl, $C_3$-$C_6$ cycloalkyl, $C_3$-$C_6$ cycloalkoxy, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

each $R_6$ is independently selected from the group consisting of $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, and heterocyclyl ($C_1$-$C_8$ alkyl), wherein said alkyl, cycloalkyl, aryl, heteroaryl, or heterocyclyl is optionally substituted with 1 to 2 W substituents or $P(O)R_{11}R_{12}$, and wherein each aryl is independently phenyl or naphthyl, each heteroaryl is independently a 5- or 6-membered aromatic ring having 1, 2 or 3 heteroatoms selected from the group consisting of N, O and S, attached through a ring carbon or nitrogen, and each heterocyclyl is independently a 5- to 7-membered saturated or unsaturated non-aromatic ring having 1, 2, 3 or 4 heteroatoms selected from the group consisting of N, O and S, attached through a ring carbon or nitrogen;

W is selected from the group consisting of H and $C_1$-$C_6$ alkoxyl;

X is O;

Y is selected from the group consisting of C=O and $SO_2$;

Z is selected from the group consisting of O, $CH_2$ and $N(R_4)$, and wherein $R_4$ is H or methyl;

M is selected from the group consisting of unsubstituted $C_1$-$C_5$ alkylene and unsubstituted $C_2$-$C_5$ alkenylene;

L is a direct bond;

each $R_7$ is independently selected from the group consisting of H, $C_1$-$C_6$ alkyl and $C_3$-$C_6$ cycloalkyl; and each $R_{10}$ is independently selected from the group consisting of H and $C_1$-$C_6$ alkyl.

2. A compound is selected from the group consisting of compounds III-1 to 111-98:
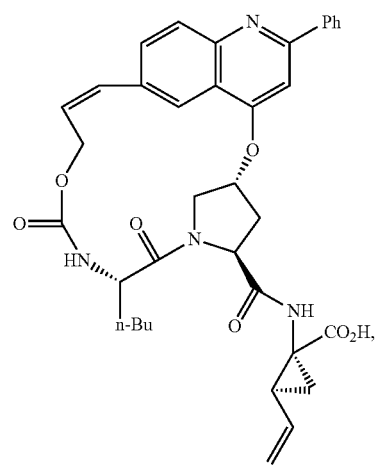
III-1
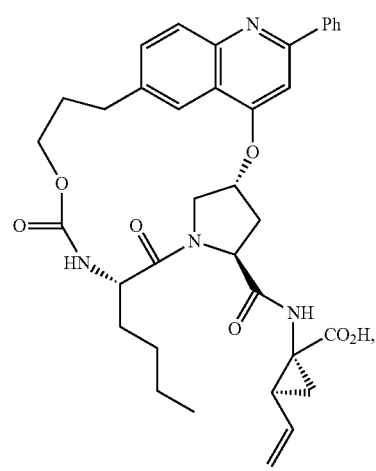
III-2
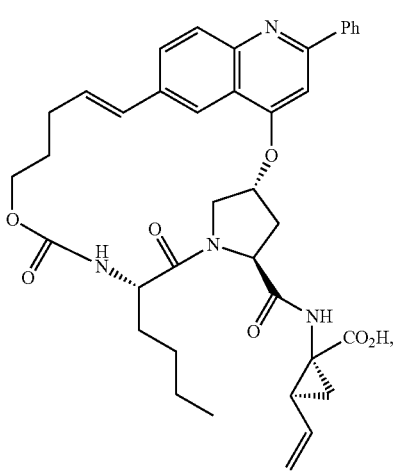
III-3
-continued
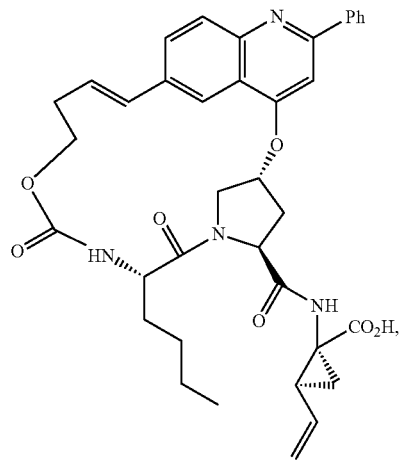
III-4
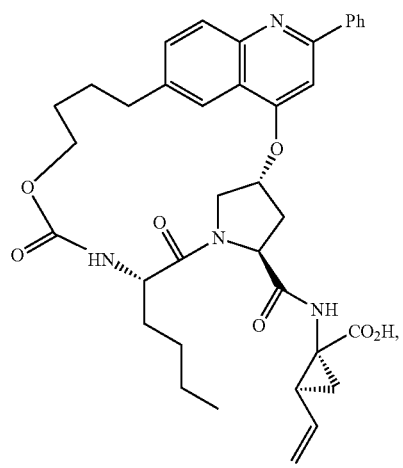
III-5
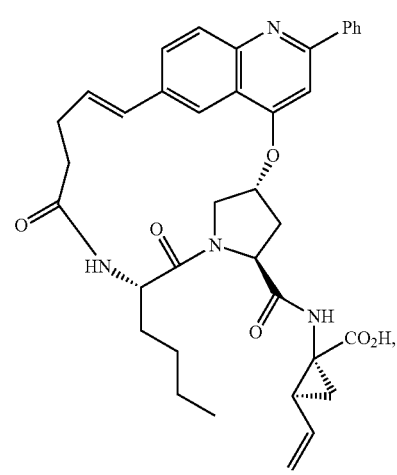
III-6

-continued
III-7
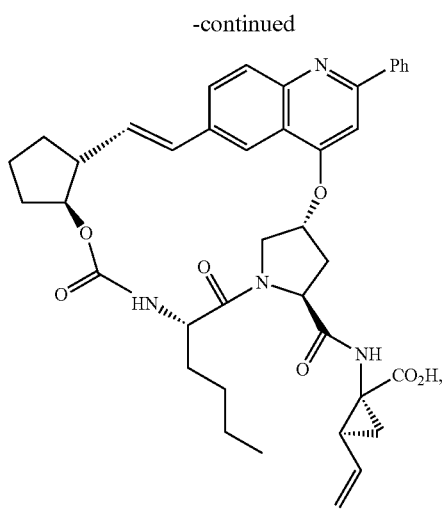
III-8
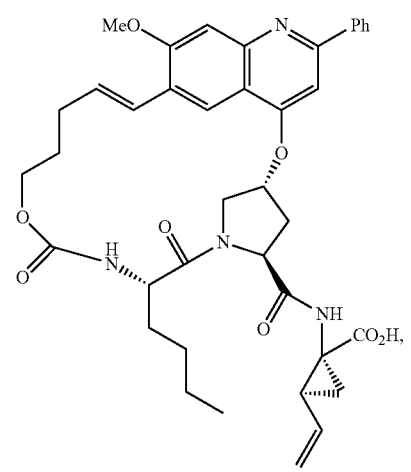
III-13
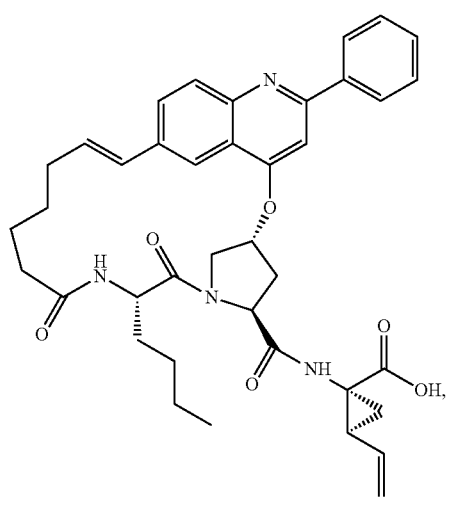
-continued
III-9
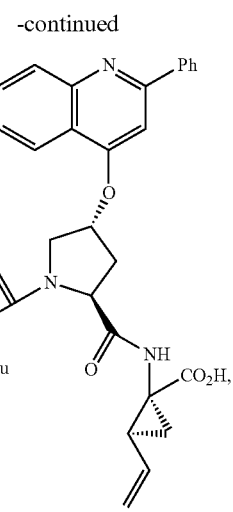
III-10
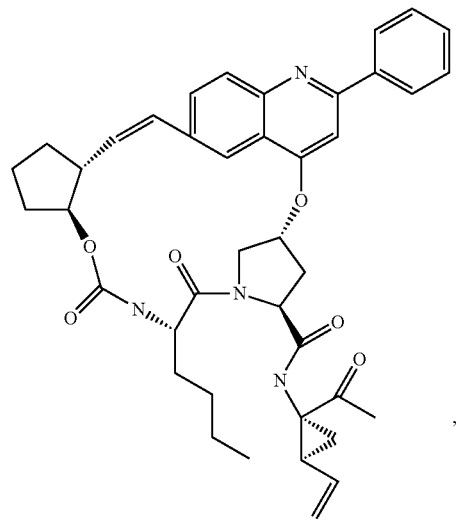
III-11
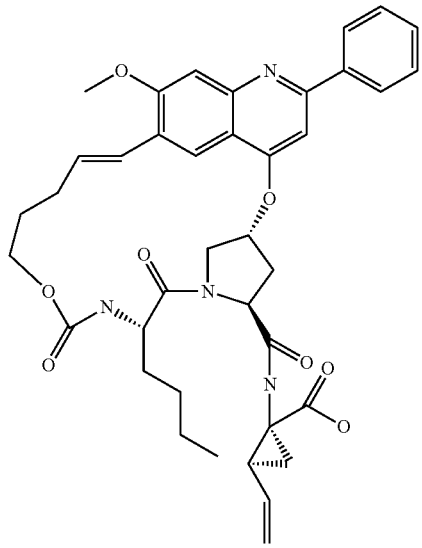

-continued
III-12
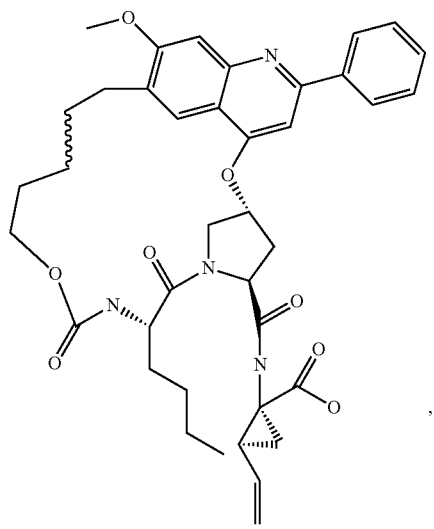
III-14
III-15
III-16
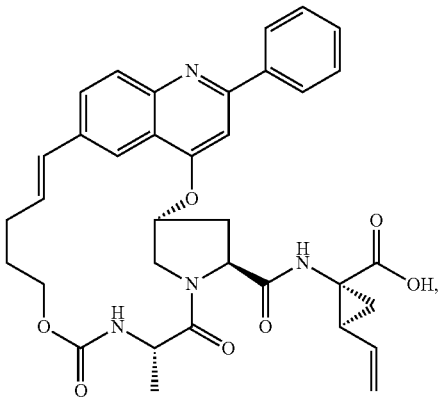
III-17
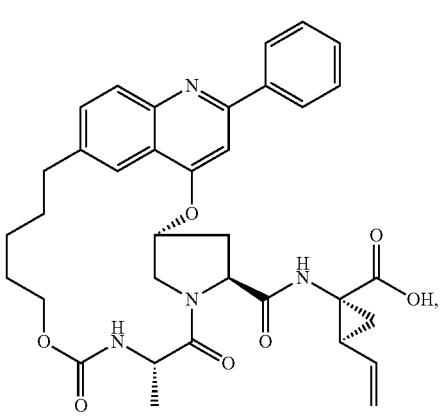
III-18
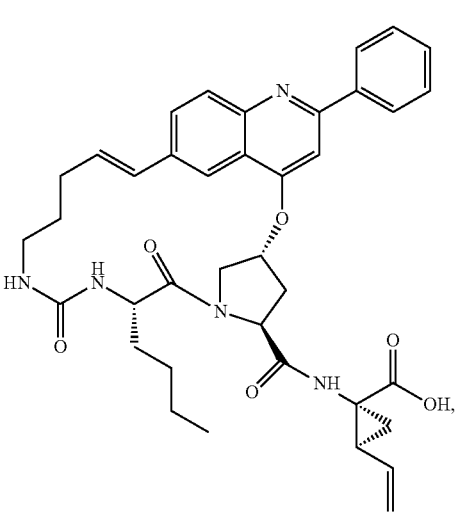

-continued
III-19
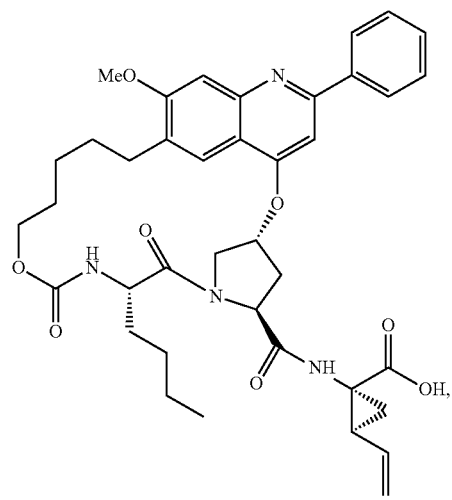
III-20
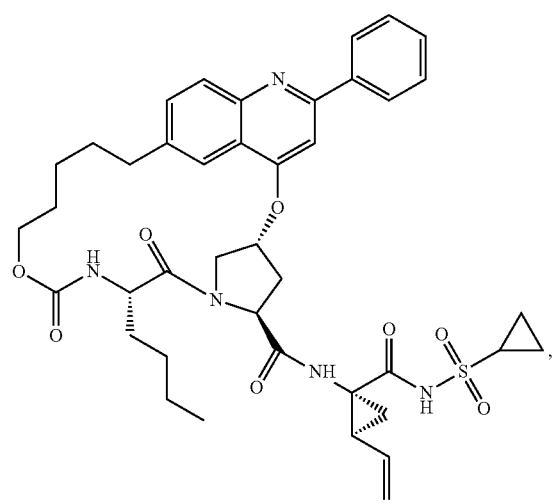
III-21
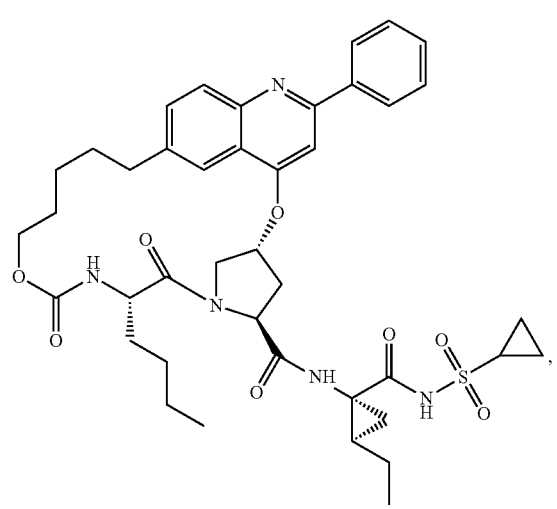
-continued
III-22
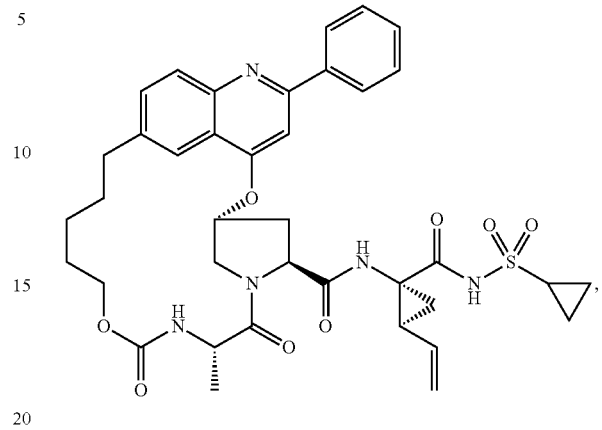
III-23
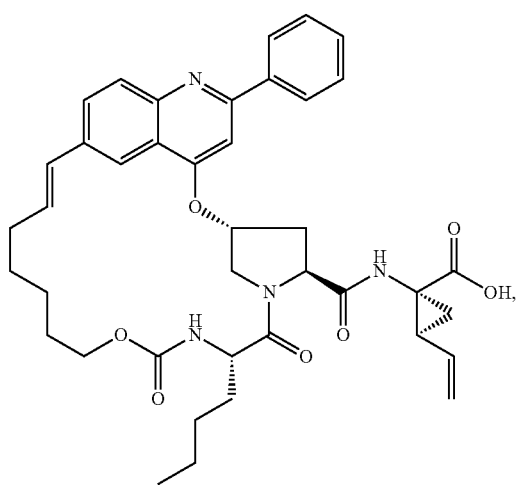
III-24
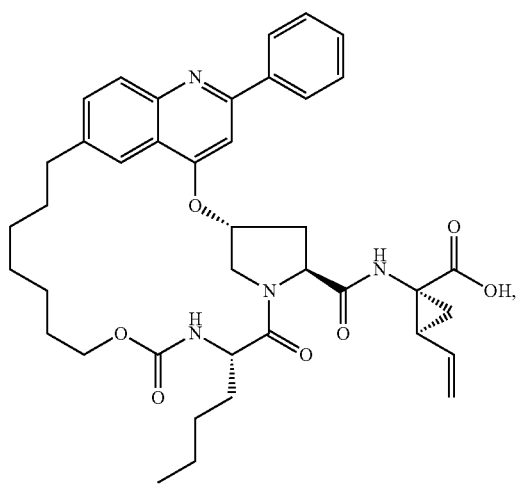

III-25

III-26

III-27

III-28

III-29

III-30

III-31
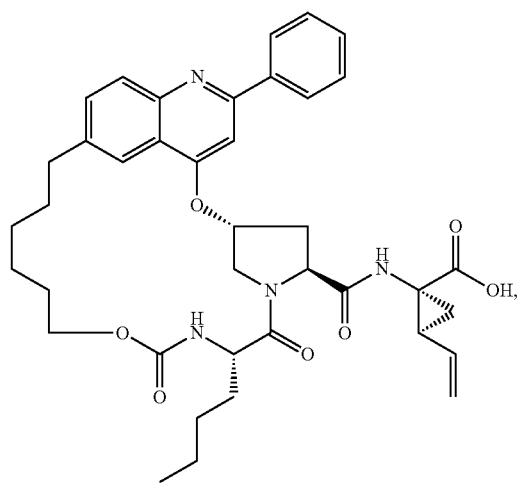
III-32
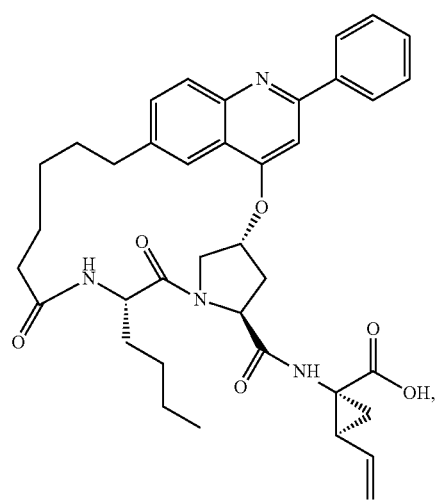
III-33
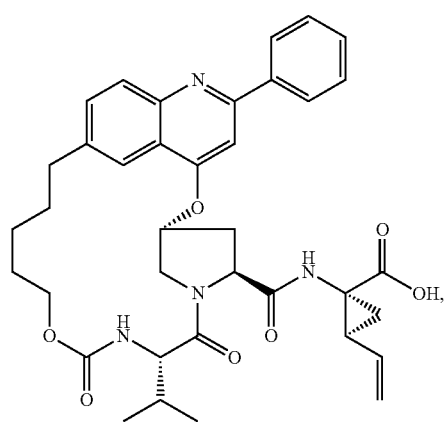
III-34
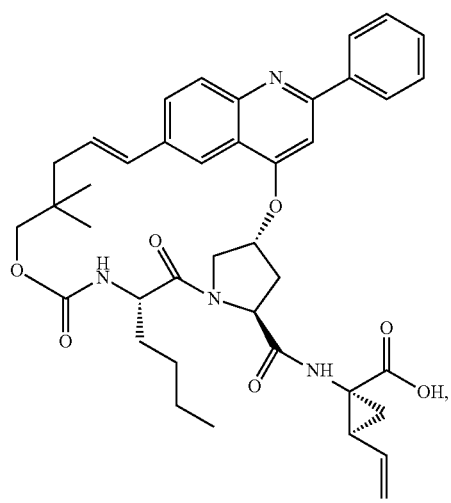
III-35
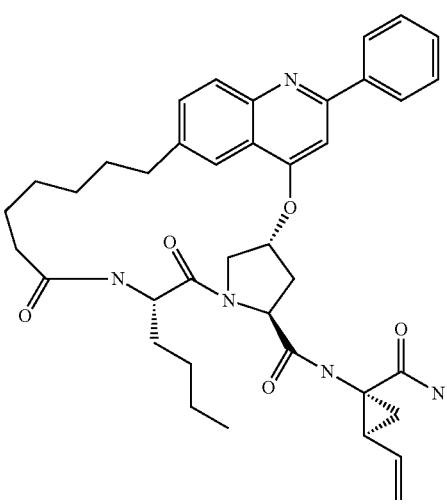
III-36
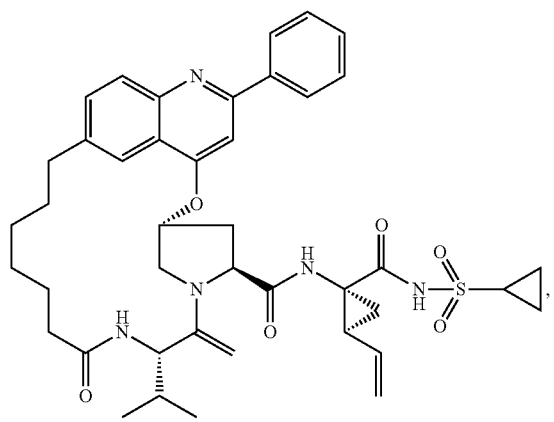

III-37
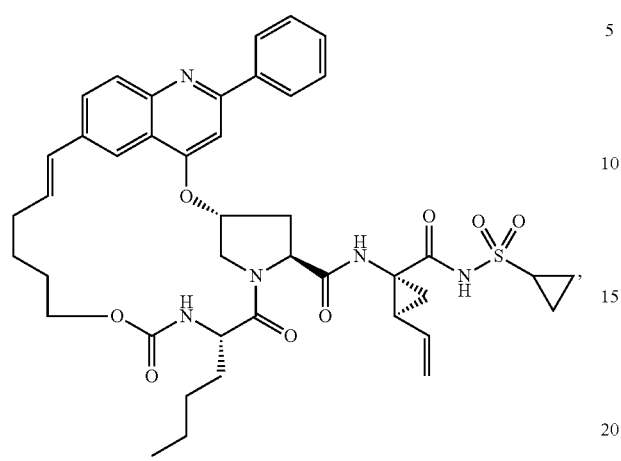
III-40
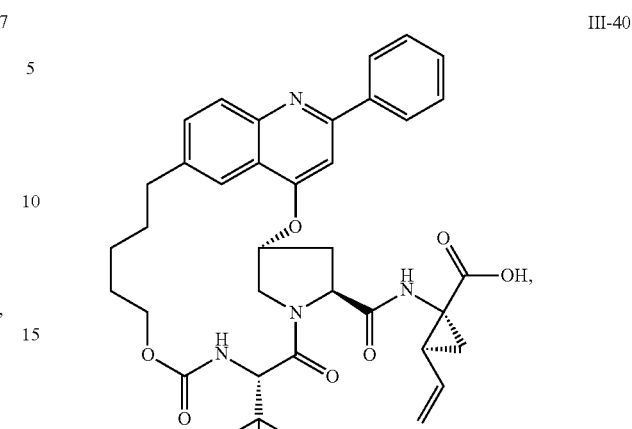
III-38
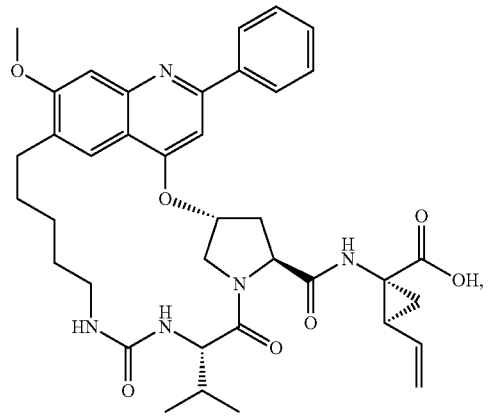
III-41
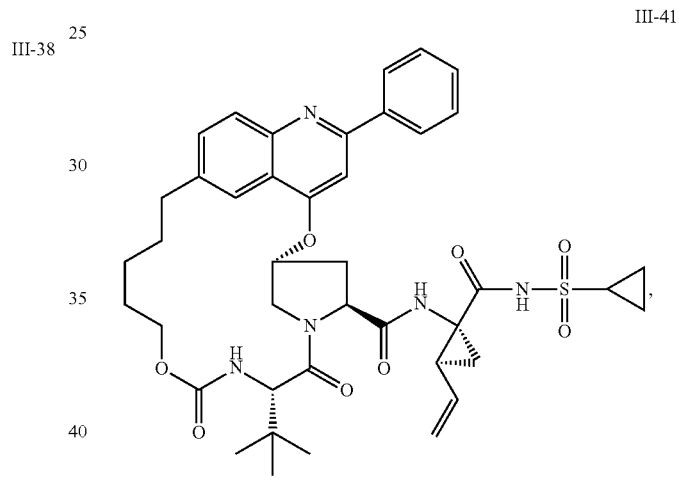
III-39
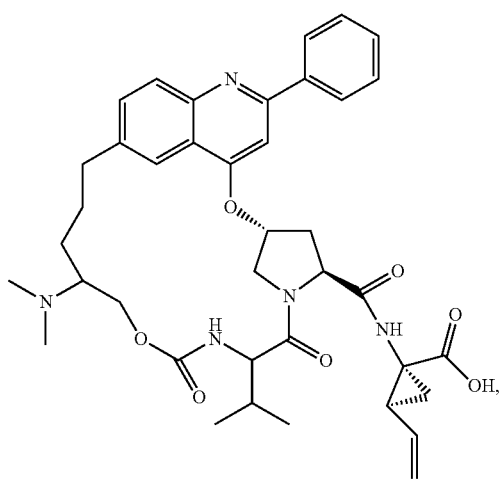
III-42
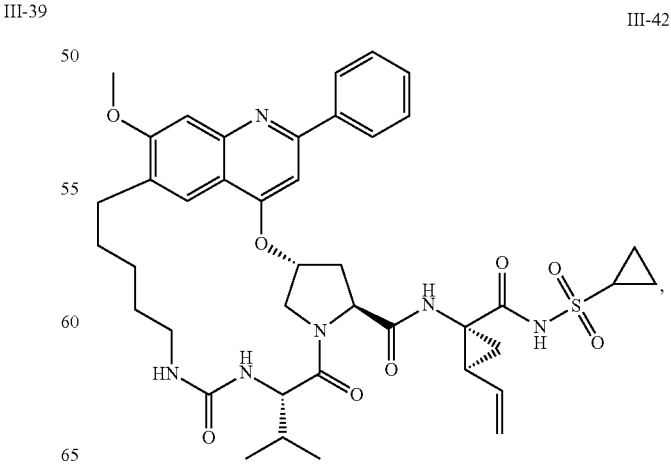

III-43
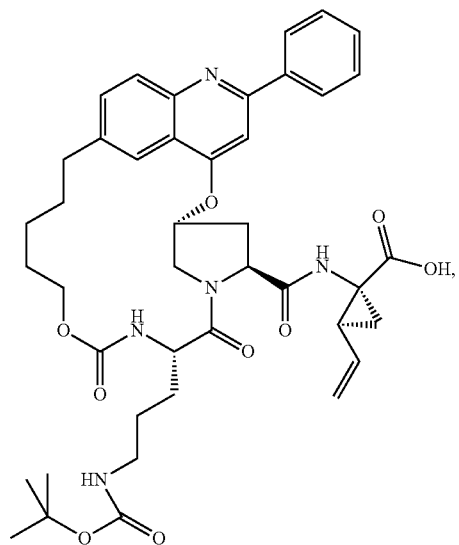
III-46
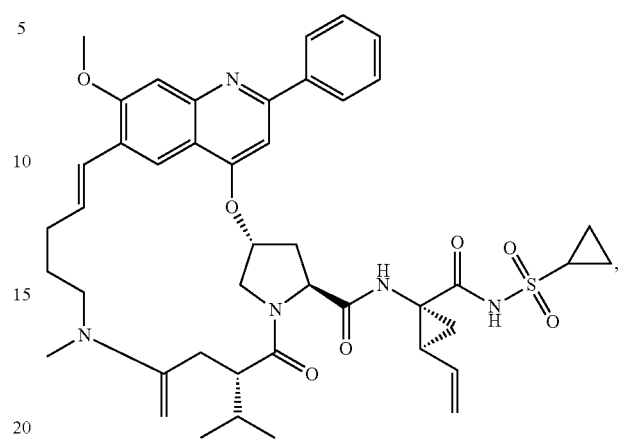
III-44
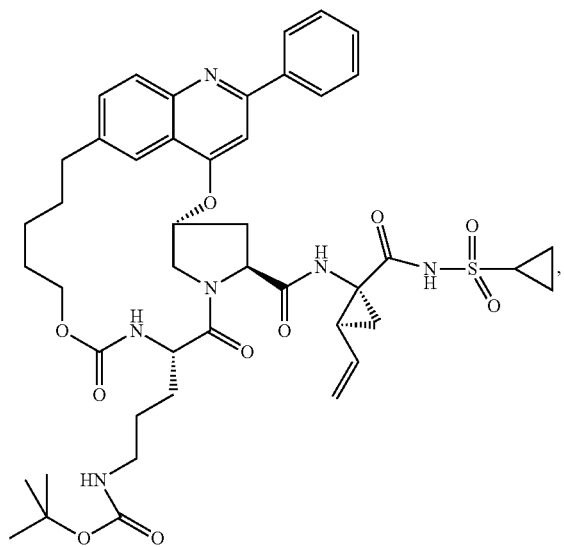
III-47
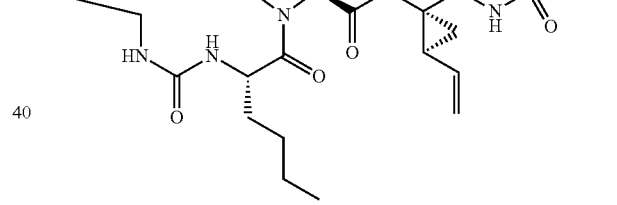
III-45
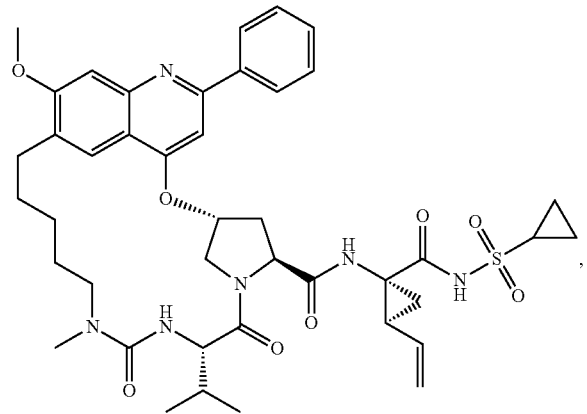
III-48
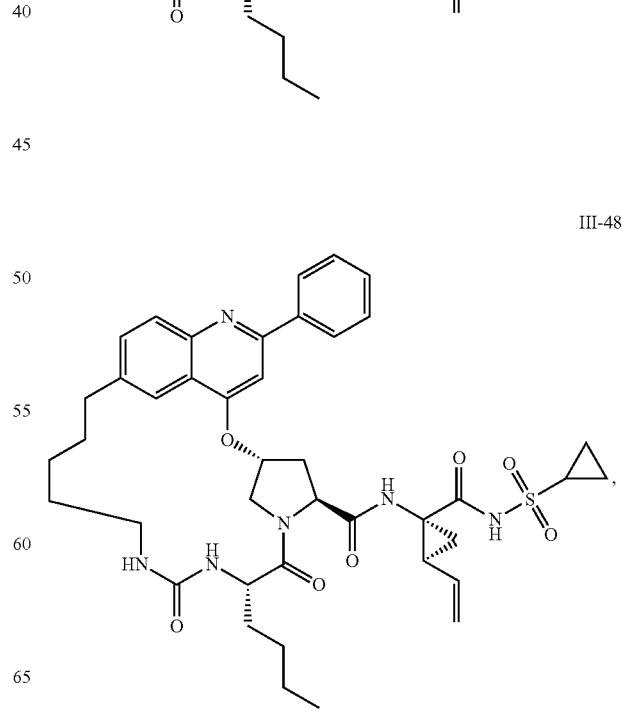

III-49
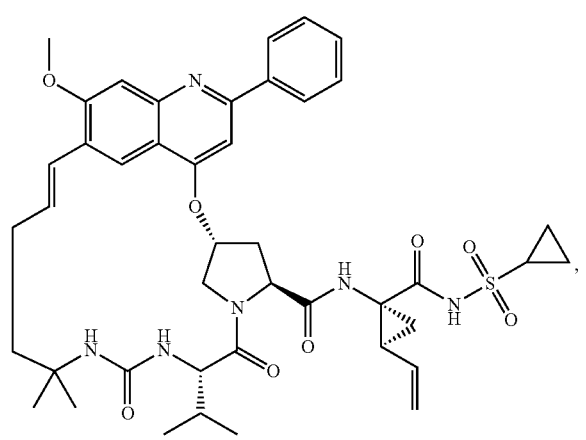
III-50
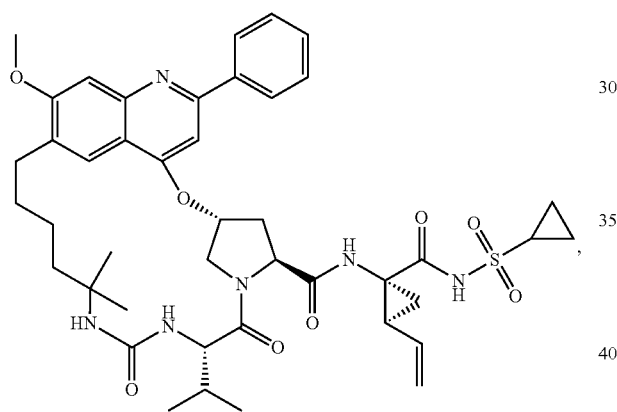
III-51
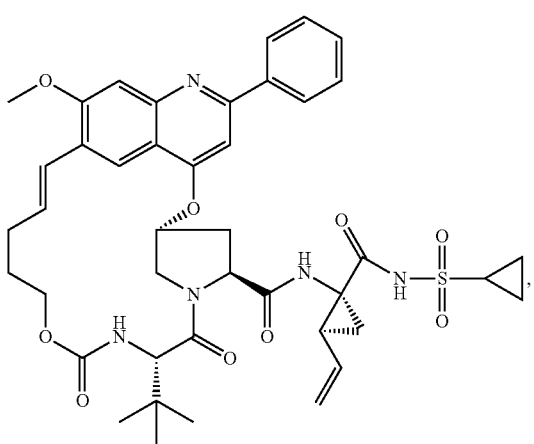
III-52
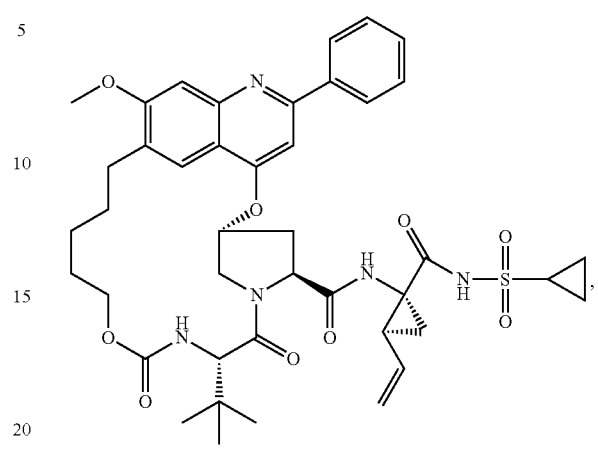
III-53
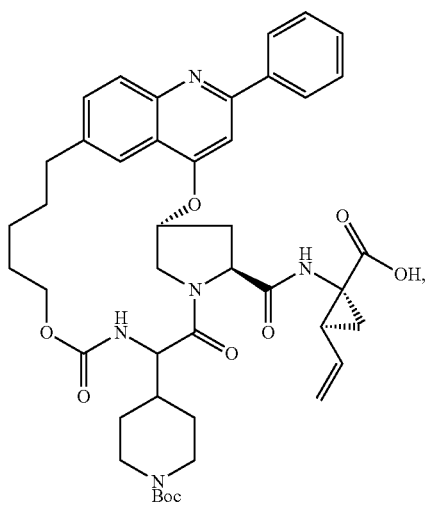
III-54
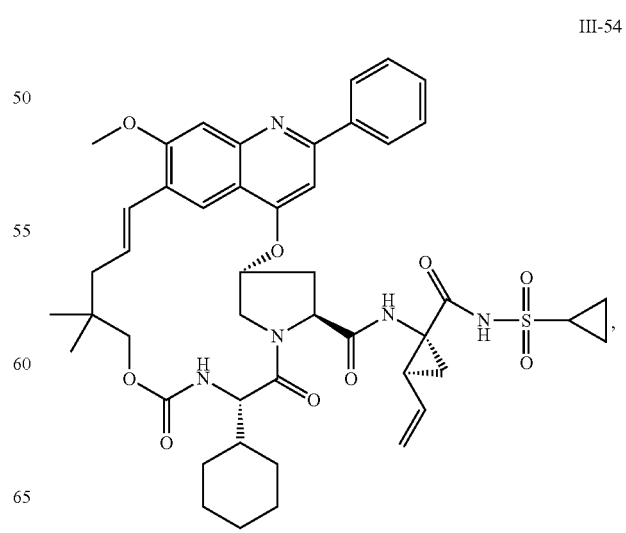

III-55
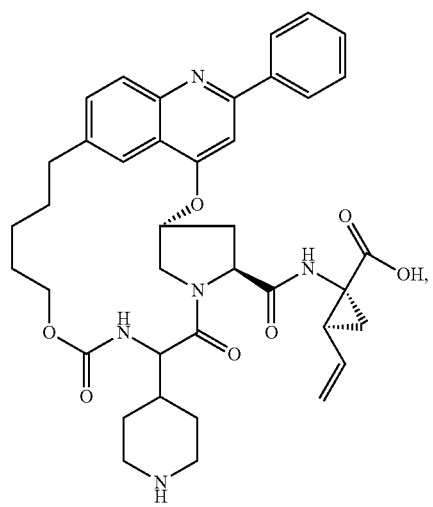
III-58
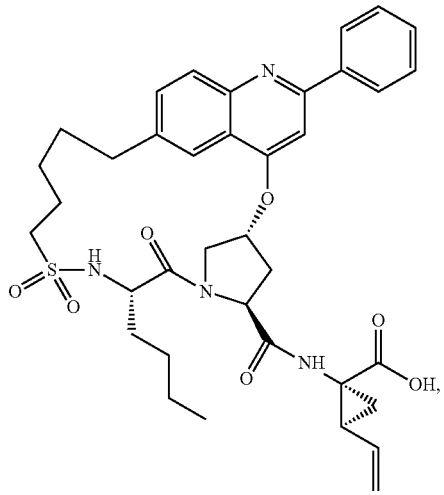
III-56
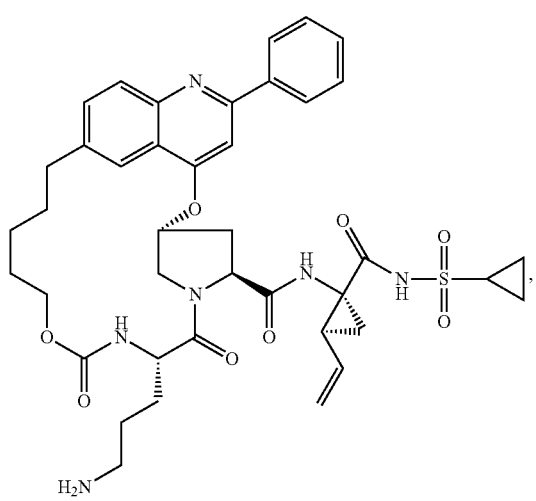
III-59
III-57
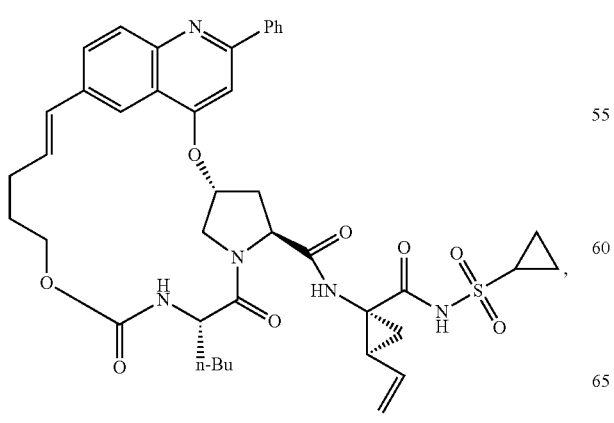
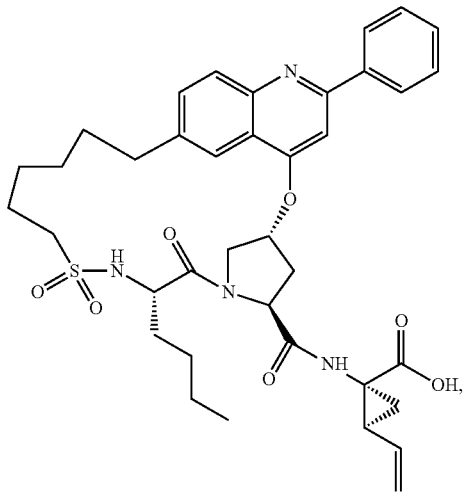
III-60

-continued
III-61
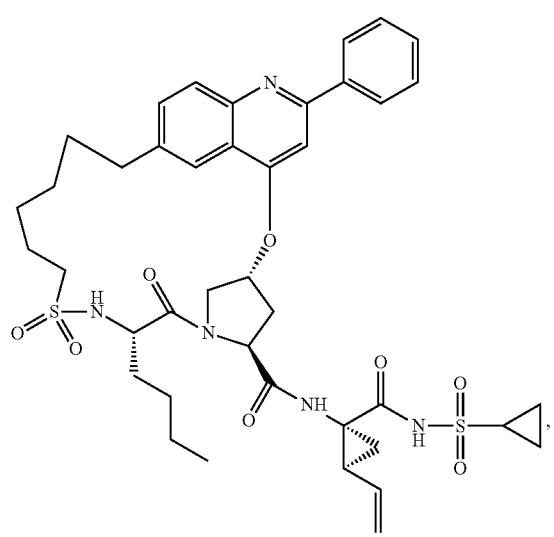
III-62
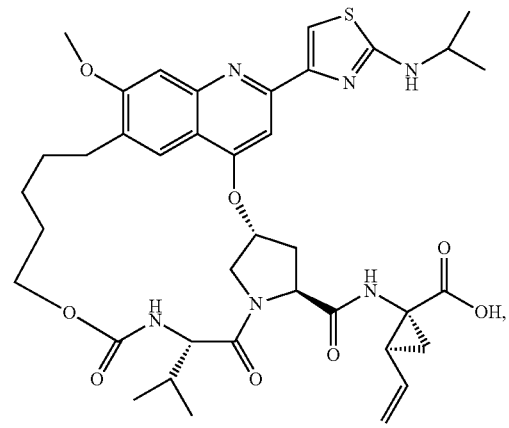
III-63
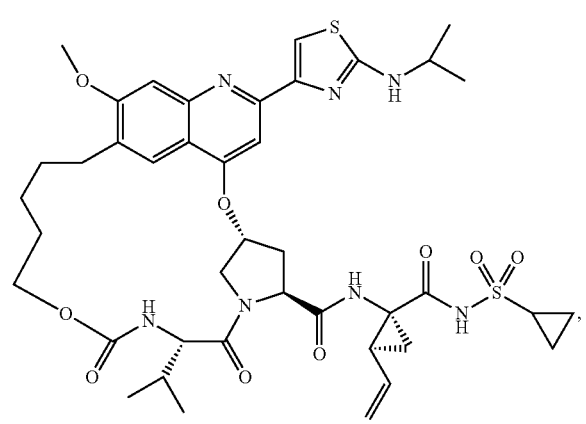
-continued
III-64
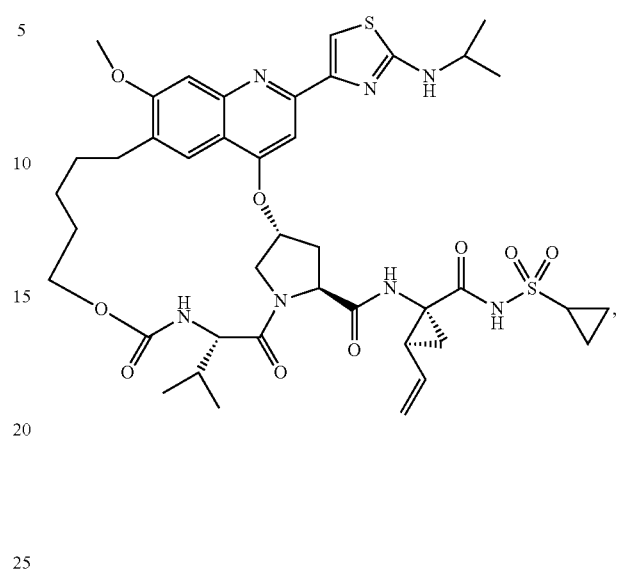
III-65
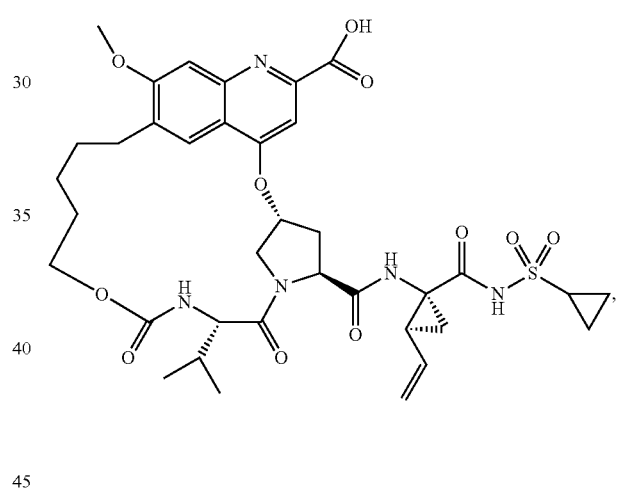
III-66
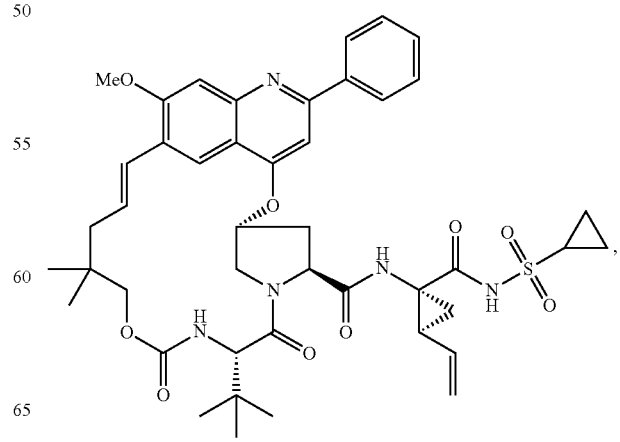

-continued
III-67
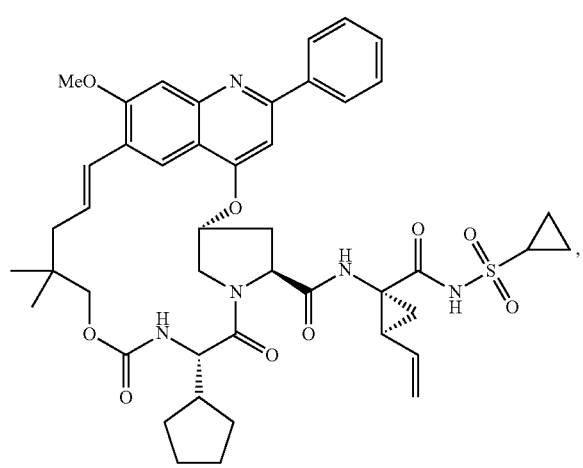
III-68
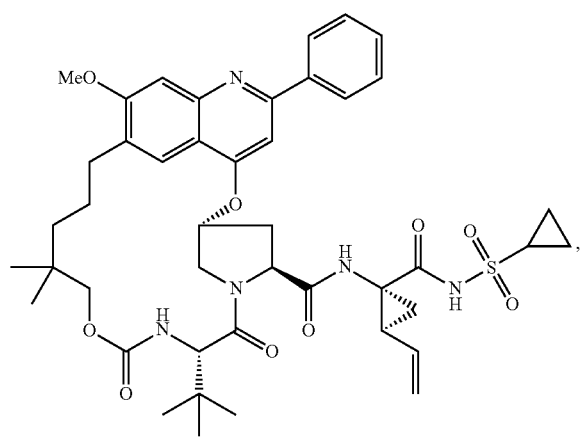
III-69
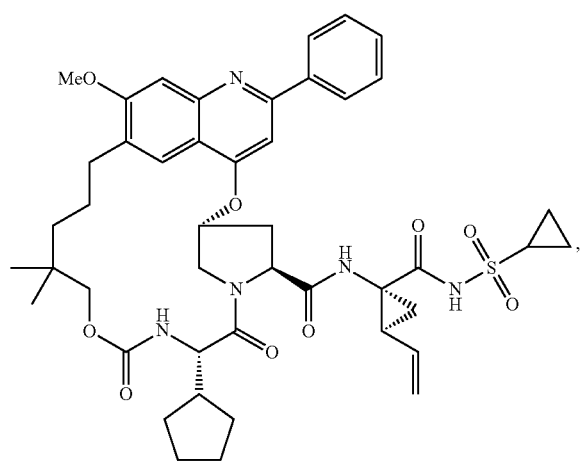
-continued
III-70
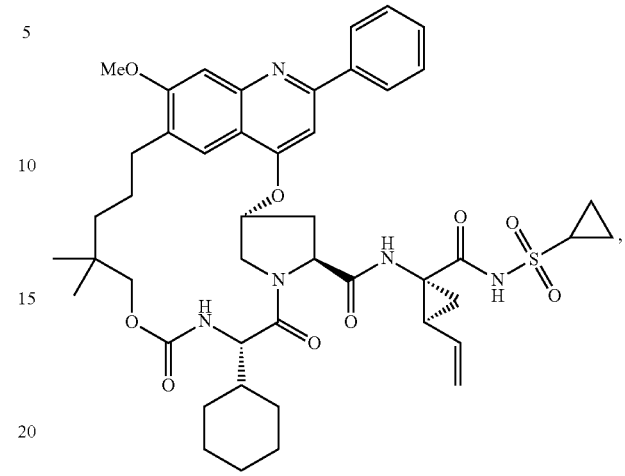
III-71
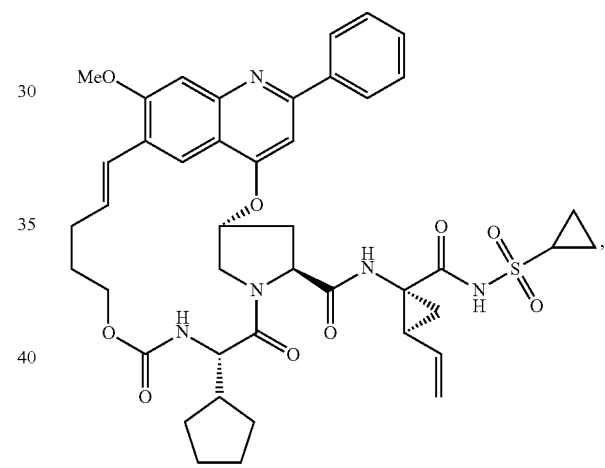
III-72
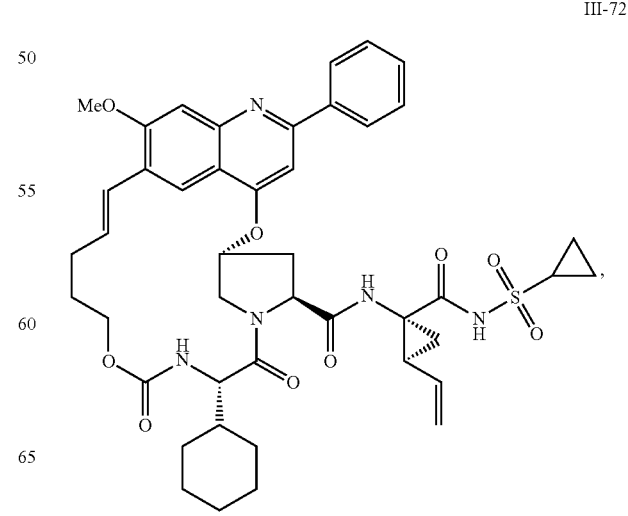

III-73
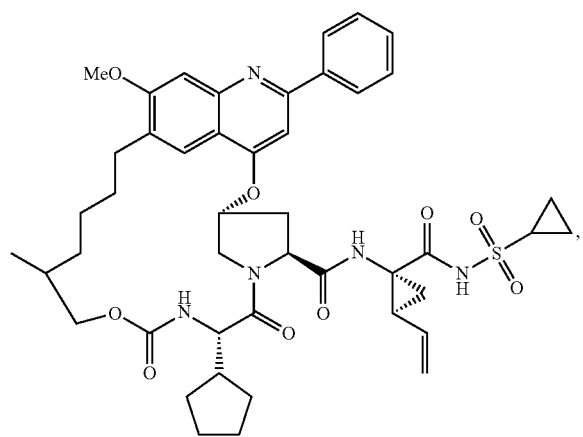
III-76
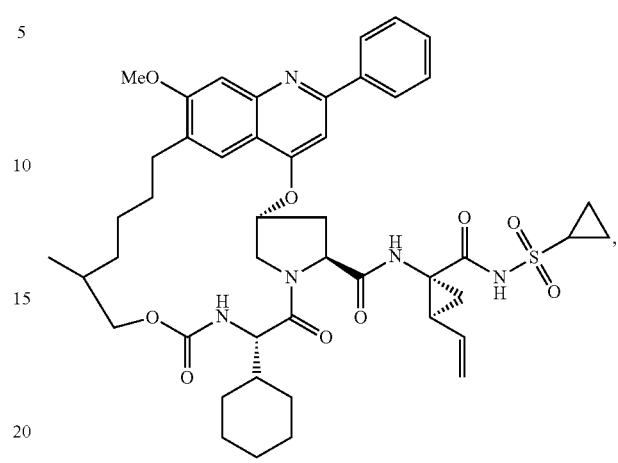
III-74
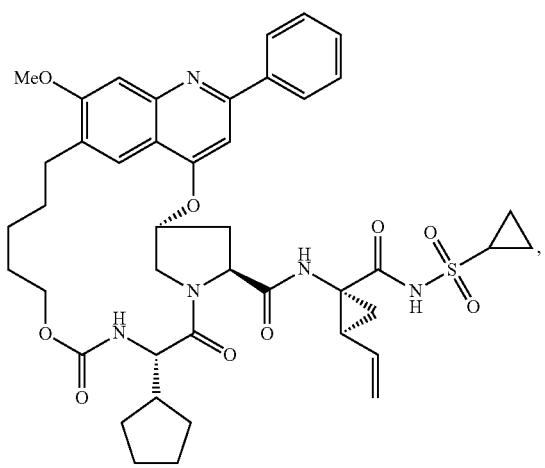
III-77
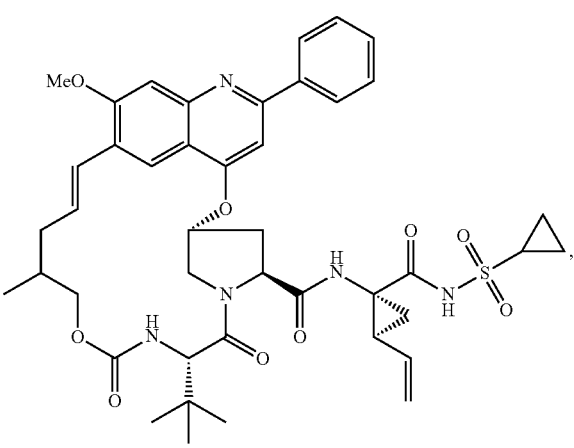
III-75
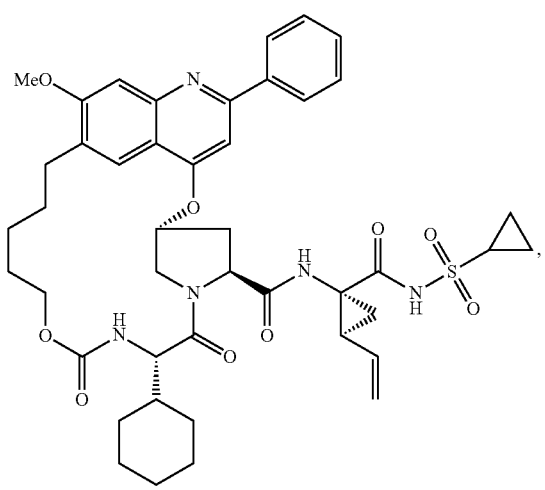
III-78
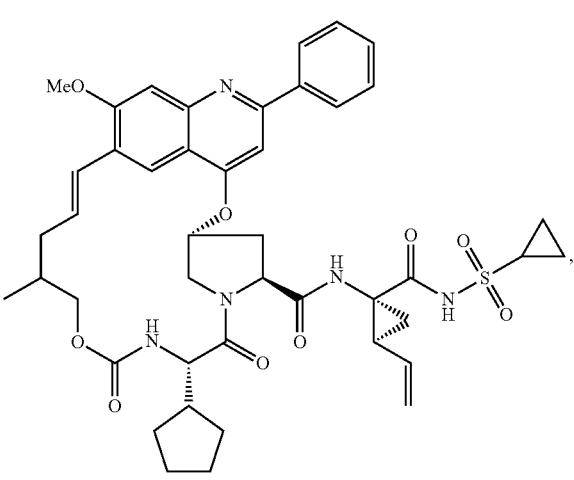

-continued
III-79
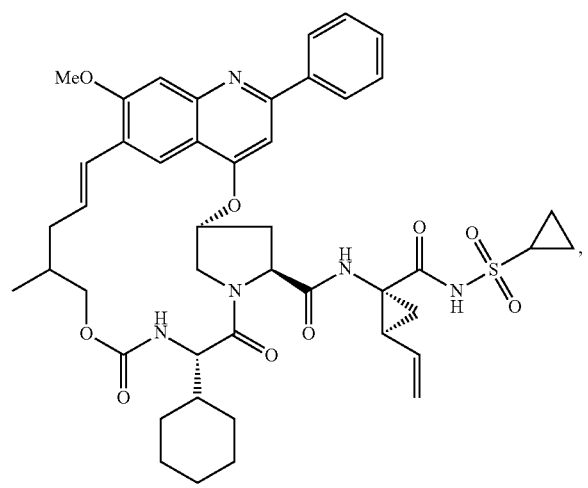
III-80
III-81
-continued
III-82
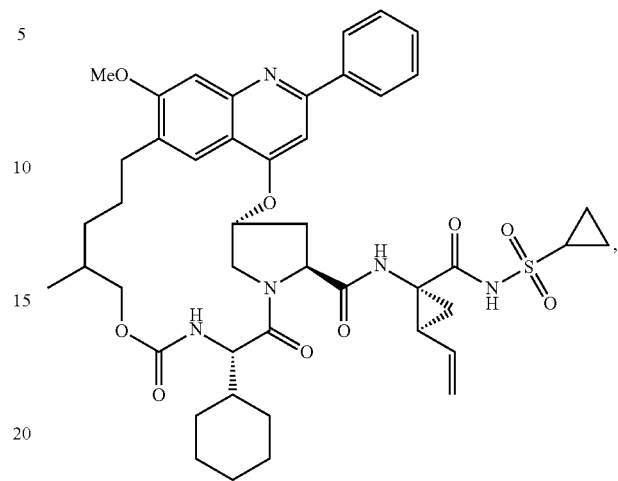
III-83
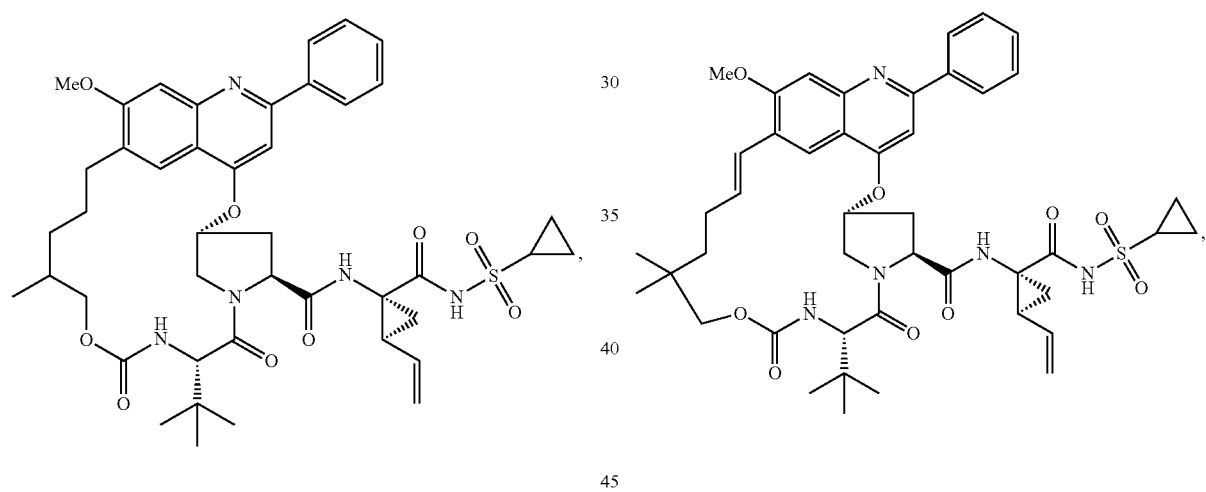
III-84
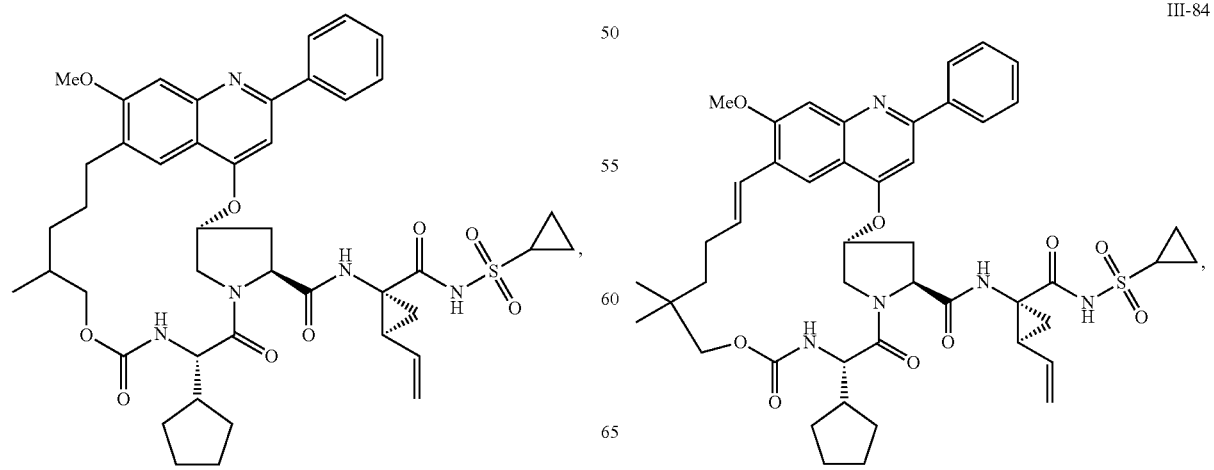

-continued
III-85
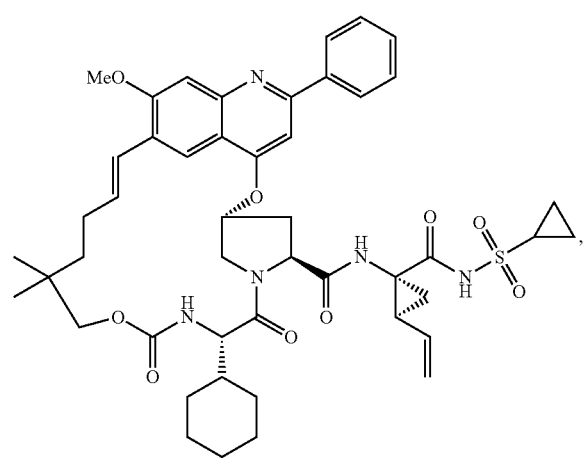
III-86
III-87
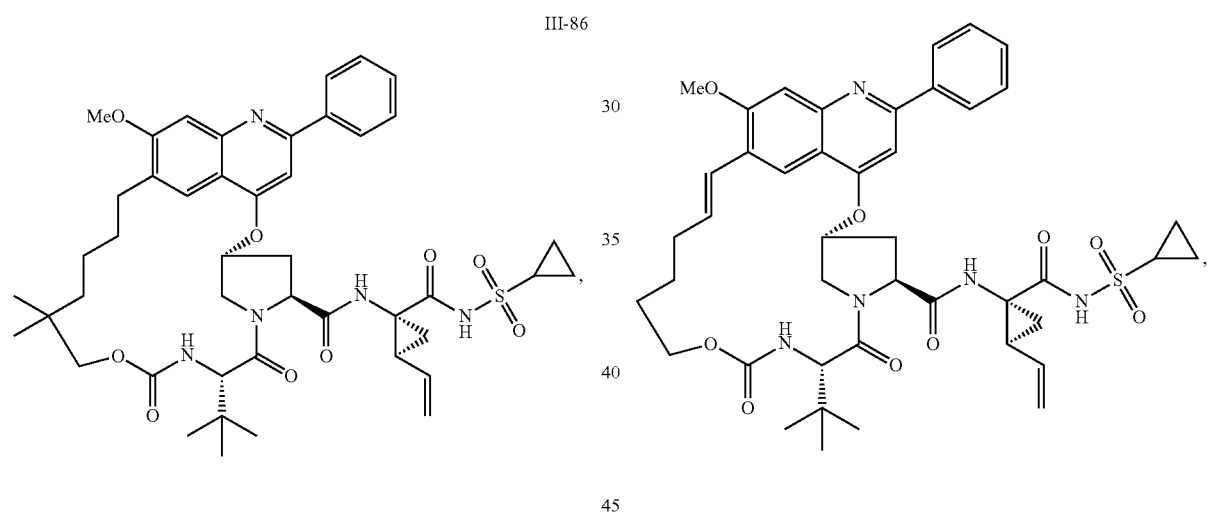
-continued
III-88
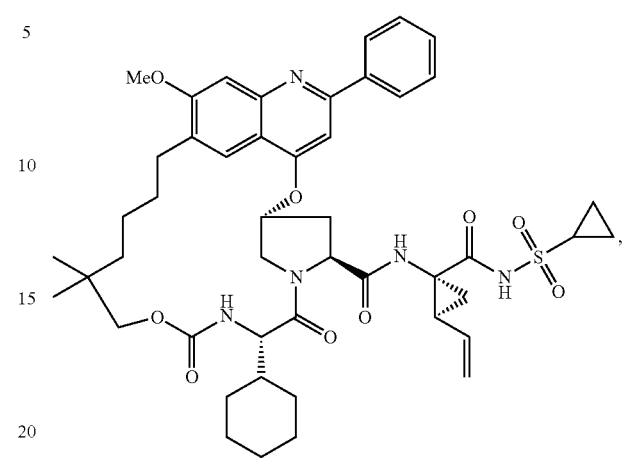
III-89
III-90
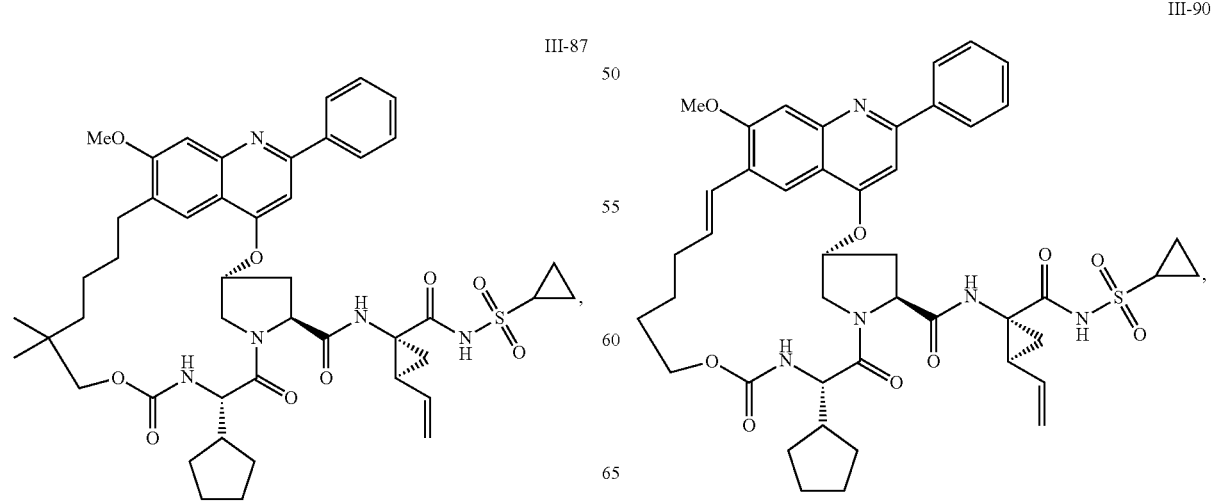

III-91
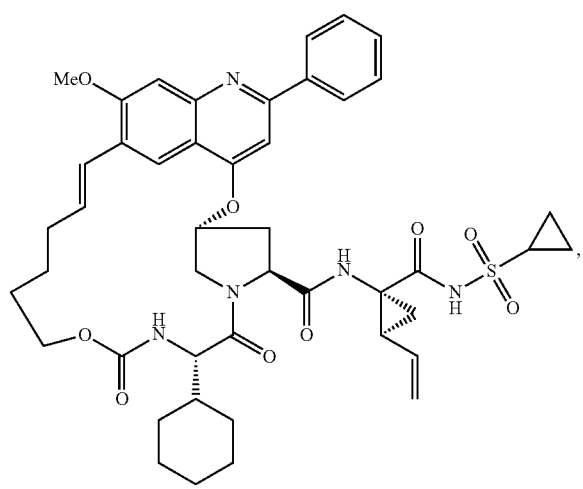
III-94
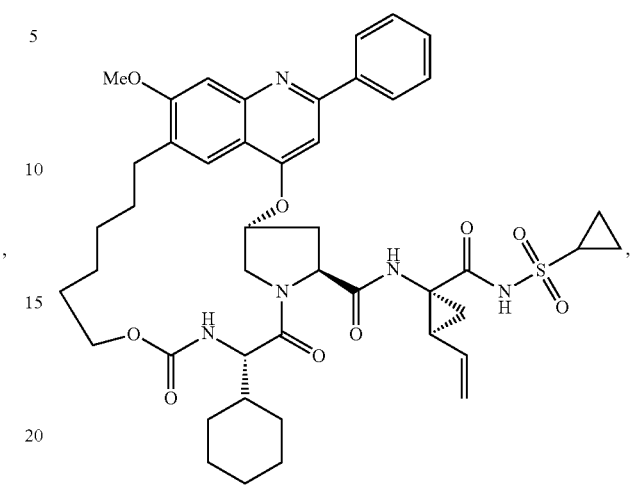
III-92
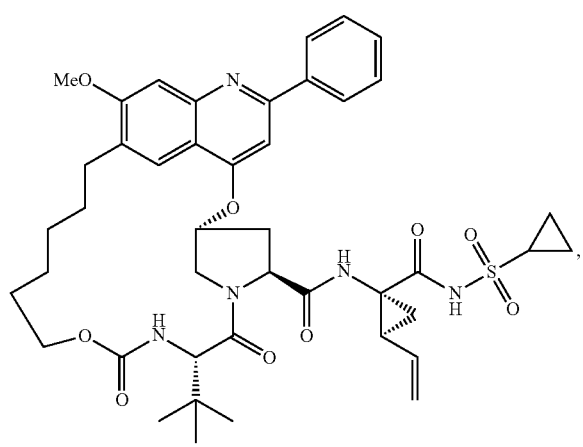
III-95
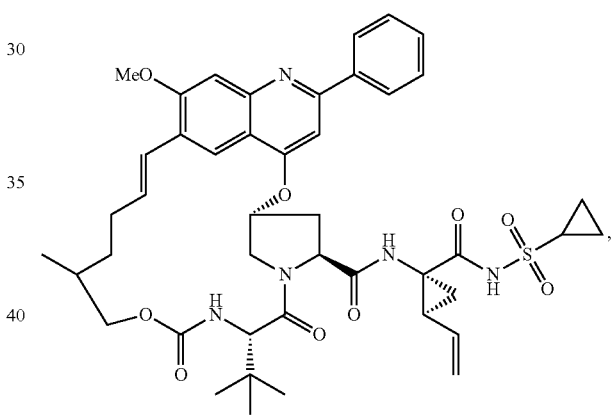
III-93
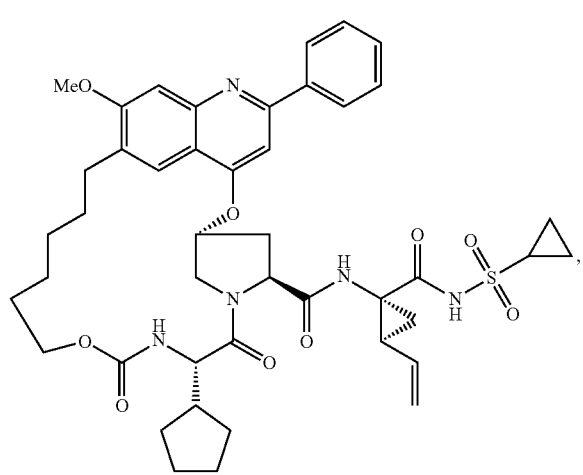
III-96
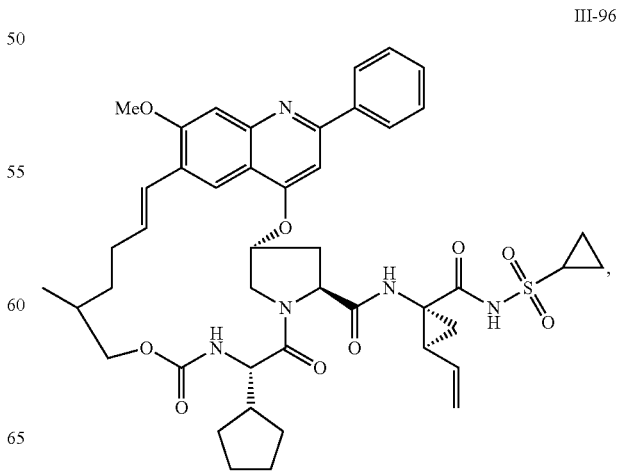

-continued

III-97

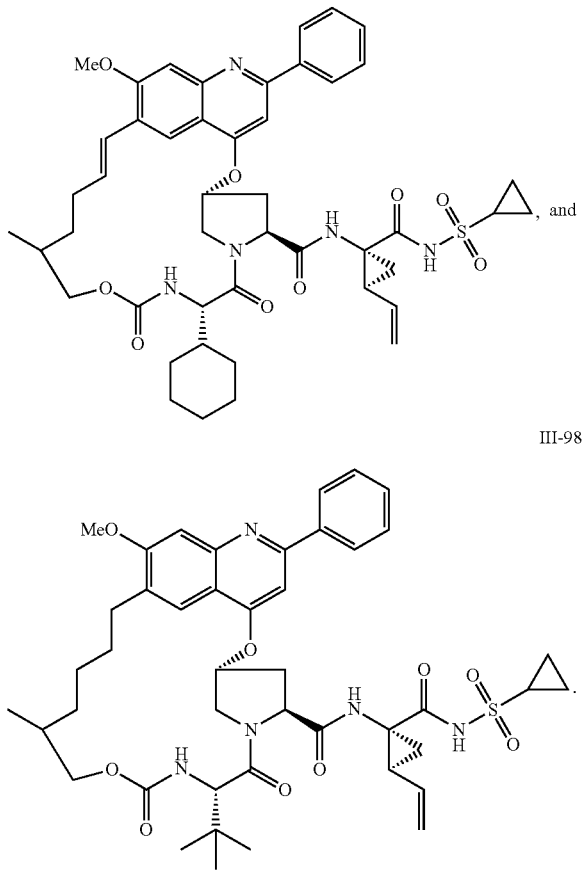

, and

III-98

3. A pharmaceutical composition comprising an effective amount of a compound of claim 1, and a pharmaceutically acceptable carrier.

4. The pharmaceutical composition of claim 3, further comprising a second therapeutic agent selected from the group consisting of a hepatitis C virus (HCV) antiviral agent, an immunomodulator, and an anti-infective agent.

5. The pharmaceutical composition of claim 4, wherein the HCV antiviral agent is an antiviral selected from the group consisting of a HCV protease inhibitor and a HCV NS5B polymerase inhibitor.

6. A method of inhibiting HCV NS3 protease activity in a subject in need thereof, said method comprising administering to said subject a medicament comprising a compound of formula III:

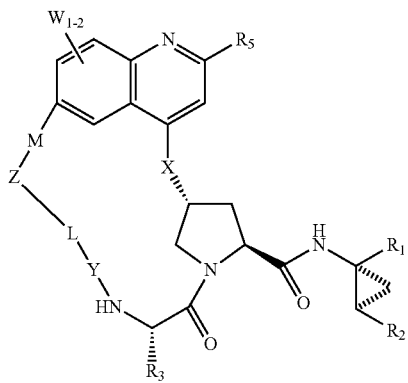

III or a pharmaceutically acceptable salt thereof, wherein:

$R_1$ is selected from the group consisting of $CO_2R_{10}$ and $CONHSO_2R_6$;

$R_2$ is selected from the group consisting of $C_1$-$C_4$ alkyl and $C_2$-$C_4$ alkenyl;

$R_3$ is selected from the group consisting of $C_1$-$C_8$ alkyl and $C_3$-$C_8$ cycloalkyl wherein each alkyl or cycloalkyl is optionally substituted with 1 to 3 substituents selected from the group consisting of halo, $OR_{10}$, $SR_{10}$, $N(R_{10})$, $C_1$-$C_6$ alkyl, $C_1$-$C_6$ haloalkyl, $NO_2$, $CN$, $CF_3$, $SO_2(C_1$-$C_6$ alkyl), $NR_{10}SO_7R_6$, $SO_2N(R_6)_2$, $NHCOOR_6$, $NHCOR_6$, $NHCONHR_6$, $CO_2R_{10}$, and $CON(R_{10})_2$;

$R_4$ is selected from the group consisting of H, $C_1$-$C_8$ alkyl, $C_3$-$C_8$ cycloalkyl($C_1$-$C_8$)alkyl, and aryl($C_1$-$C_8$)alkyl; wherein aryl is phenyl or naphthyl and said alkyl, cycloalkyl, or aryl is optionally substituted with 1 to 3 substituents selected from the group consisting of halo, $OR_{10}SR_{10}$, $N(R_{10})_2$, $C_1$-$C_6$ alkyl, $C_1$-$C_6$ haloalkyl, $NO_2$ $CN$ $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

$R_5$ is selected from the group consisting of $CO_2R_4$, aryl, and heteroaryl, wherein said aryl or heteroaryl is optionally substituted with 1 to 4 substituents selected from the group consisting of halo, $OR_{10}$, $SR_{10}$, $N(R_7)_2$, $C_1$-$C_6$ alkyl, $C_1$-$C_6$ haloalkyl, $C_3$-$C_6$ cycloalkyl, $C_3$-$C6$ cycloalkoxy, $NO_2$, $CN$, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

each $R_6$ is independently selected from the group consisting of $C_1$-$C_6$ alkyl, $C_3$-$C_6$ cycloalkyl, $C_3$-$C_6$ cycloalkyl ($C_1$-$C_5$)alkl, aryl, aryl ($C_1$-$C_4$)alkyl, heteroaryl, heteroaryl($C_1$-$C_4$ alkyl), heterocyclyl, and heterocyclyl ($C_1$-$C_8$ alkyl), wherein said alkyl, cycloalkyl, aryl, heteroaryl, or heterocyclyl is optionally substituted with 1 to 2 W substituents or $P(O)R_{11}R_{12}$, and wherein each aryl is independently phenyl or naphthyl, each heteroaryl is independently a 5- or 6-membered aromatic ring having 1, 2 or 3 heteroatoms selected from the group consisting of N, O and S, attached through a ring carbon or nitrogen, and each heterocyclyl is independently a 5- to 7-membered saturated or unsaturated non-aromatic ring having 1, 2, 3 or 4 heteroatoms selected from the group consisting of N, O and S, attached through a ring carbon or nitrogen;

W is selected from the group consisting of H and $C_1$-$C_6$ alkoxy;

X is O;

Y is selected from the group consisting of C=O and $SO_2$;

Z is selected from the group consisting of O, $CH_2$ and $N(R_4)$, and wherein $R_4$ is H or methyl;

M is selected from the group consisting of unsubstituted $C_1$-$C_5$ alkylene and unsubstituted $C_2$-$C_5$ alkenylene;

L is a direct bond;

each $R_7$ is independently selected from the group consisting of H, $C_1$-$C_6$ alkyl and $C_3$-$C_6$ cycloalkyl; and each $R_{10}$ is independently selected from the group consisting of H and $C_1$-$C_6$ alkyl.

7. A method of or treating infection by HCV in a subject in need thereof, said method comprising administering to said subject a medicament comprising a compound of formula III:

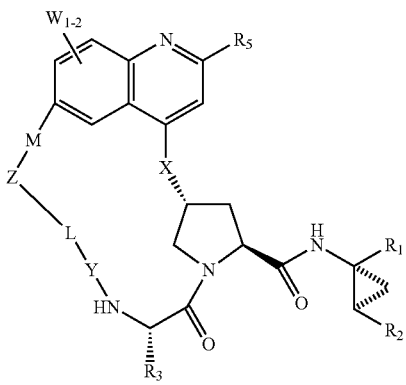

III or a pharmaceutically acceptable salt thereof, wherein:

$R$ is selected from the group consisting of $CO_2R_{10}$ and $CONHSO_2R_6$;

$R_2$ is selected from the group consisting of $C_1$-$C_4$ alkyl and $C_2$-$C_4$ alkenyl;

$R_3$ is selected from the group consisting of $C_1$-$C_8$ alkyl and $C_3$-$C_8$ cycloalkyl wherein each alkyl or cycloalkyl is optionally substituted with 1 to 3 substituents selected from the group consisting of halo, $OR_{10}$, $SR_{10}$, $N(R_{10})_2$, $C_1$-$C_6$ alkyl, $C_1$-$C_6$ haloalkyl, $NO_2$, $CN$, $CF_3$ $SO_2(C_1$-$C_6$ alkyl), $NR_{10}SO_2R_6$ $SO_2N(R_6$ $NHCOOR_6$ $NHCOR_6$, $NHCONHR_5$ $CO_2R_{10}$, and $CON(R_{10})_2$;

$R_4$ is selected from the group consisting of H, $C_1$-$C_8$ alkyl, $C_3$-$C_8$ cycloalkyl($C_1$-$C_8$)alkyl, and aryl($C_1$-$C_8$)alkyl; wherein aryl is phenyl or naphthyl and said alkyl, cycloalkyl, or aryl is optionally substituted with 1 to 3 substituents selected from the group consisting of halo, $OR_{10}$, $SR_{10}$, $N(R_{10})_2 C_1$-$C_6$ alkyl, $C_1$-$C_6$ haloalkyl, $NO_2$, $CN$, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

$R_5$ is selected from the group consisting of $CO_2R_4$, aryl, and heteroaryl, wherein said aryl or heteroaryl is optionally substituted with 1 to 4 substituents selected from the group consisting of halo, $OR_{10}$, $SR_{10}$, $N(R_7)_2C_1$-$C_6$ alkyl, $C_1$-$C_6$ haloalkyl, $C_3$-$C_6$ cycloalkyl, $C_3$-$C6$ cycloalkoxy, $NO_2$, $CN$, $CF_3$, $SO_2C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

each $R_6$ is independently selected from the group consisting of $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, and heterocyclyl ($C_1$-$C_8$ alkyl), wherein said alkyl, cycloalkyl, aryl, heteroaryl, or heterocyclyl is optionally substituted with 1 to 2 W substituents or $P(O)R_{11}R_{12}$, and wherein each aryl is independently phenyl or naphthyl, each heteroaryl is independently a 5- or 6-membered aromatic ring having 1, 2 or 3 heteroatoms selected from the group consisting of N, O and S, attached through a ring carbon or nitrogen, and each heterocyclyl is independently a 5- to 7-membered saturated or unsaturated non-aromatic ring having 1, 2, 3 or 4 heteroatoms selected from the group consisting of N, O and S, attached through a ring carbon or nitrogen;

W is selected from the group consisting of H and $C_1$-$C_6$ alkoxy;

X is O;

Y is selected from the group consisting of C=O and $SO_2$;

Z is selected from the group consisting of O, $CH_2$ and $N(R_4)$, and wherein $R_4$ is H or methyl;

M is selected from the group consisting of unsubstituted $C_1$-$C_5$ alkylene and unsubstituted $C_2$-$C_5$ alkenylene;

L is a direct bond;

each $R_7$ is independently selected from the group consisting of H, $C_1$-$C_6$ alkyl and $C_3$-$C_6$ cycloalkyl; and each $R_{10}$ is independently selected from the group consisting of H and $C_1$-$C_6$ alkyl.

8. The method of claim 7, wherein said medicament further comprises at least one second therapeutic agent selected from the group consisting of a HCV antiviral agent, an immunomodulator, and an anti-infective agent.

9. The method of claim 8, wherein the HCV antiviral agent is an antiviral selected from the group consisting of a HCV protease inhibitor and a HCV NS5B polymerase inhibitor.

10. A pharmaceutical composition comprising an effective amount of a compound of claim 2, and a pharmaceutically acceptable carrier.

11. The pharmaceutical composition of claim 10, further comprising a second therapeutic agent selected from the group consisting of a hepatitis C virus (HCV) antiviral agent, an immunomodulator, and an anti-infective agent.

12. The pharmaceutical composition of claim 10, wherein the HCV antiviral agent is an antiviral selected from the group consisting of a HCV protease inhibitor and a HCV NS5B polymerase inhibitor.

13. A method of inhibiting HCV NS3 protease activity in a subject in need thereof, said method comprising administering to said subject a medicament comprising a compound of claim 2.

14. A method of or treating infection by HCV in a subject in need thereof, said method comprising administering to said subject a medicament comprising a compound of claim 2.

15. The method of claim 14, wherein said medicament further comprises at least one second therapeutic agent selected from the group consisting of a HCV antiviral agent, an immunomodulator, and an anti-infective agent.

16. The method of claim 15, wherein the HCV antiviral agent is an antiviral selected from the group consisting of a HCV protease inhibitor and a HCV NS5B polymerase inhibitor.

* * * * *